(12) United States Patent
Shinohata et al.

(10) Patent No.: US 11,046,645 B2
(45) Date of Patent: Jun. 29, 2021

(54) ISOTHIOCYANATE PRODUCTION METHOD, COMPOSITION FOR TRANSPORTING AND STORING N-SUBSTITUTED O-SUBSTITUTED THIOCARBAMATE, AND ISOTHIOCYANATE COMPOSITION

(71) Applicant: Asahi Kasei Kabushiki Kaisha, Tokyo (JP)

(72) Inventors: Masaaki Shinohata, Tokyo (JP); Yuji Kosugi, Tokyo (JP); Nobuhisa Miyake, Tokyo (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 114 days.

(21) Appl. No.: 16/382,738

(22) Filed: Apr. 12, 2019

(65) Prior Publication Data
US 2019/0233371 A1 Aug. 1, 2019

Related U.S. Application Data

(62) Division of application No. 14/772,943, filed as application No. PCT/JP2014/055144 on Feb. 28, 2014, now Pat. No. 10,308,601.

(30) Foreign Application Priority Data

Mar. 5, 2013 (JP) .............................. JP2013-042863
Mar. 5, 2013 (JP) .............................. JP2013-042867

(51) Int. Cl.
*C07C 331/20* (2006.01)
*C07C 331/30* (2006.01)
(Continued)

(52) U.S. Cl.
CPC .......... *C07C 331/30* (2013.01); *C07C 329/04* (2013.01); *C07C 331/20* (2013.01);
(Continued)

(58) Field of Classification Search
CPC .... C07C 331/30; C07C 331/20; C07C 331/22
See application file for complete search history.

(56) References Cited

U.S. PATENT DOCUMENTS 2,824,887 A 2/1958 Klopping
2,983,747 A 5/1961 Campbell et al.
(Continued)

FOREIGN PATENT DOCUMENTS

CN 1849301 A 10/2006
CN 103140473 A 6/2013
(Continued)

OTHER PUBLICATIONS

FR-2693106_Jan. 1994_English Translation.*
(Continued)

*Primary Examiner* — Michael L Leonard
(74) *Attorney, Agent, or Firm* — Morgan, Lewis &. Bockius LLP

(57) ABSTRACT

The present invention relates to an isothiocyanate production method using an organic primary amine and thiourea as starting materials; to a composition for transporting and storing an N-substituted O-substituted thiocarbamate that includes an N-substituted O-substituted thiocarbamate and a hydroxy compound, the equivalent weight ratio of hydroxy groups of the hydroxy compound with respect to the carbamate groups of the N-substituted O-substituted thiocarbamate being in the range of 1 to 100; to a composition for transporting and storing a compound with a thioureido group that includes a compound with a thioureido group and a hydroxy compound, the equivalent weight ratio of hydroxy (Continued)

groups of the hydroxy compound with respect to the thioureido groups of the compound with a thioureido group being in the range of 1 to 100; and to an isothiocyanate composition containing an isothiocyanate and a compound with a specific functional group.

18 Claims, 5 Drawing Sheets

(51) Int. Cl.
| | |
|---|---|
| C07C 333/04 | (2006.01) |
| C07C 333/06 | (2006.01) |
| C07C 333/08 | (2006.01) |
| C07C 335/08 | (2006.01) |
| C07C 335/14 | (2006.01) |
| C07C 329/04 | (2006.01) |
| C07C 335/10 | (2006.01) |
| C07C 335/16 | (2006.01) |
| C07C 331/22 | (2006.01) |
| C07C 333/20 | (2006.01) |
| C07C 333/22 | (2006.01) |
| C07C 333/24 | (2006.01) |

(52) U.S. Cl.
CPC .......... *C07C 331/22* (2013.01); *C07C 333/04* (2013.01); *C07C 333/06* (2013.01); *C07C 333/08* (2013.01); *C07C 333/20* (2013.01); *C07C 333/22* (2013.01); *C07C 333/24* (2013.01); *C07C 335/08* (2013.01); *C07C 335/10* (2013.01); *C07C 335/14* (2013.01); *C07C 335/16* (2013.01); *C07C 2601/14* (2017.05)

(56) References Cited

U.S. PATENT DOCUMENTS

| | | | |
|---|---|---|---|
| 3,111,536 A | | 11/1963 | Tarlton et al. |
| 3,712,158 A | | 1/1973 | Kalopissis et al. |
| 3,836,524 A | | 9/1974 | Pitt |
| 4,328,247 A | | 5/1982 | Drabek et al. |
| 4,897,424 A | | 1/1990 | Boger et al. |
| 4,939,257 A | | 7/1990 | Drabek et al. |
| 4,997,967 A | * | 3/1991 | Hassig ................. C07C 331/28 558/19 |
| 5,250,717 A | | 10/1993 | Knapp |
| 5,326,903 A | | 7/1994 | Shimasaki et al. |
| 2005/0032849 A1 | | 2/2005 | Phadke et al. |
| 2005/0192347 A1 | | 9/2005 | Dasseux et al. |
| 2013/0184488 A1 | * | 7/2013 | Shinohata ............. C07C 263/20 560/345 |

FOREIGN PATENT DOCUMENTS

| | | | |
|---|---|---|---|
| EP | 2626345 A1 | 8/2013 | |
| FR | 2693106 A | * 1/1994 | ............ A61K 31/26 |
| FR | 2693106 A1 | 1/1994 | |
| FR | 2988000 A1 | 9/2013 | |
| JP | S44-013139 B | 6/1969 | |
| JP | S56-158758 A | 12/1981 | |
| JP | S64-019061 A | 1/1989 | |
| JP | H04-210959 A | 8/1992 | |
| JP | H04-270260 A | 9/1992 | |
| JP | H05-186415 A | 7/1993 | |
| JP | H09-202767 A | 8/1997 | |
| TW | 201219346 A1 | 5/2012 | |
| WO | 2005/007601 A2 | 1/2005 | |
| WO | 2011/021258 A1 | 2/2011 | |
| WO | 2012/046734 A1 | 4/2012 | |

OTHER PUBLICATIONS

Katritzky et al., "Synthesis of Mono- and N,N-Disubstituted Thioureas and N-Acylthioureas," Synthesis, 11: 1799-1805 (2004).
Erickson, "Reactions of Long-Chain Amines. VI. Preparation of Thioureas," Journal of Organic Chemistry, 21: 483-484 (1956).
Moore et al. "Methyl Isothiocyanate (Isothiocyanic acid, methyl ester)," Organic Synthesis Collective, 3: 599-600 (1955).
Volynkin, "Method for Synthesizing Arylthioureas and the Corresponding Mustard Oils," Zhurmal Obshchei Khimii, 27: 549-551 (1957).
Takeda et al., "Bile Acids and Steroids. XII. Thiosteroids(1). The Fission of Epoxide in the C-Ring of Steroids by Thiocyanic Acid," Chemical and Pharmaceutical Bulletin (Tokyo), 8: 468-474 (1960).
International Preliminary Report on Patentability and Written Opinion issued in corresponding International Patent Application No. PCT/JP2014/055144 dated Sep. 17, 2015.
International Search Report issued in corresponding International Patent Application No. PCT/JP2014/055144 dated May 27, 2014.
Extended European Search Report issued in corresponding European Patent Application No. 18162365.3 dated May 23, 2018.
Extended European Search Report issued in counterpart European Patent Application No. 17159930.1 dated Jul. 17, 2017.
Erickson, "Notes-Reactions of Long-Chain AMINES.VI. Preparation of Thioureas," Journal of Organic Chemistry, 21: 483-484 (1956).
Partial Supplementary Search Report issued in counterpart European Patent Application No. 14760523.2 dated Mar. 11, 2016.
Derume et al., "Ethanolysis of Thioureas," Scientia Pharmaceutica, 64: 327-333 (1996).
European Search Report issued in counterpart European Patent Application No. 14760523.2 dated Jul. 5, 2016.
Lomba et al., "Anodic oxidation of thioureido derivatives of biogenic amines at a glassy carbon electrode in an aqueous medium," Journal of Electroanalytical Chemistry, 410: 87-92 (1996).
Perveen et al., "Effect of successive increase in alcohol chains on reaction with isocyanates and isothiocyanates," Natural Product Research, 24 (1): 18-23 (2010).

* cited by examiner

ISOTHIOCYANATE PRODUCTION METHOD, COMPOSITION FOR TRANSPORTING AND STORING N-SUBSTITUTED O-SUBSTITUTED THIOCARBAMATE, AND ISOTHIOCYANATE COMPOSITION

TECHNICAL FIELD

The present invention relates to an isothiocyanate production method, to a composition for transporting and storing an N-substituted O-substituted thiocarbamate, and to an isothiocyanate composition.

BACKGROUND ART

Compounds with isothiocyanate groups are known as activating agents with antimicrobial effects. For example, Brassicaceae Brassica plants such as Yamato-mana (*Brassica rapa L. oleifera*), komatsuna (*Brassica chinensis*) and nozawana (*Brassica rapa* var. *hakabura*) contain abundant amounts of various isothiocyanate glycosides (glucosinolates) such as arylalkyl isothiocyanates, alkenylalkyl isothiocyanates and methylsulfinylalkyl isothiocyanates, which by myrosinase activity are converted to their respective isothiocyanates, and these are of increasing interest because they exhibit a variety of physiologically active effects including antimicrobial activity, cancer-preventing effects and anti-inflammatory effects.

Isothiocyanates are usually utilized by means such as extraction of the components in plants as mentioned above, but several isothiocyanate production methods have also been proposed to date. For example, PTL 1 and NPL 1 each disclose a production method by reaction between an olefin, an epoxy compound, a halide and thiocyanic acid, while NPL 2 discloses reaction between a dithiocarbamic acid salt and a chlorformic acid ester. In addition, PTL 2 discloses a production method by reaction between an amino compound and thiophosgene, while PTL 3 discloses an isothiocyanate production method by reacting an amine compound with an ammonium salt or alkali metal salt of thiocyanic acid to produce a thiourea group, and heating the product.

CITATION LIST

Patent Literature

[PTL 1] U.S. Pat. No. 3,111,536
[PTL 2] U.S. Pat. No. 2,824,887
[PTL 3] JP H4-270260 A

Non-Patent Literature

[NPL 1] Chem. Pharm. Bull. (Tokyo), 8, 486, 1960
[NPL 2] Org. Synth., III, 599, 1955

SUMMARY OF INVENTION

Technical Problem

As mentioned above, various different methods for production of isothiocyanates are being investigated. With methods using thiocyanic acid, however, owing to the instability of thiocyanic acid itself it is difficult to handle during procedures such as production of thiocyanic acid in the reaction system and its direct use for production of isothiocyanate. In addition, in methods using an ammonium salt or alkali metal salt of thiocyanic acid, the reaction produces the salt in an equimolar amount with isothiocyanate groups, and much effort and cost are required to deal with it. Methods with thiophosgene generate poisonous hydrogen sulfide from the reaction, such that the treatment required for its detoxification becomes a major burden. Furthermore, because it is difficult to separate and purify the compounds that are produced as by-products of these methods from the isothiocyanate, they often mix in trace amounts with the isothiocyanate, resulting in reduction in the storage stability of the isothiocyanate.

One object of the invention is to provide an isothiocyanate production method that utilizes easily handleable compounds and can be easily accomplished without by-production of poisonous compounds. It is another object of the invention to provide a composition containing a compound having a thioureido group, that is suitable for production of an N-substituted O-substituted thiocarbamate, and a composition containing an N-substituted O-substituted thiocarbamate, that is suitable for production of an isothiocyanate by thermal decomposition of the N-substituted O-substituted thiocarbamate, as well as an isothiocyanate production method using the composition, and an isothiocyanate composition with satisfactory storage stability.

Solution to Problem

As a result of much diligent research on this issue, the present inventors have found an isothiocyanate production method using an organic primary amine and thiourea as starting materials, and have found that it is easy to produce an N-substituted O-substituted thiocarbamate by recovering the gas component by-product of the method as a gas phase component with a specific composition, and have further found a specific composition containing a compound with a thioureido group that is suited for this method, a specific composition containing an N-substituted O-substituted thiocarbamate, and an isothiocyanate composition containing a specific compound, thereby completing the present invention.

Specifically, the invention provides the following.

The following are provided as a first aspect of the invention.

[1] A method for producing an isothiocyanate using an organic primary amine and thiourea as starting materials.

[2] The method according to [1], comprising: a step (1) of producing a compound with a thioureido group and ammonia by reacting the organic primary amine and the thiourea; and a step (2) of thermally decomposing the compound with a thioureido group and then separating an isothiocyanate and ammonia generated.

[3] The method according to [1], comprising a step (I) of reacting the organic primary amine and the thiourea and then separating an isothiocyanate and ammonia generated.

[4] The method according to [1], comprising: a step (A) of producing a compound with a thioureido group and ammonia by reacting the organic primary amine and the thiourea; a step (B) of separating ammonia after producing an N-substituted O-substituted thiocarbamate and ammonia by reacting the compound with a thioureido group and a hydroxy compound; and a step (C) of producing an isothiocyanate by thermally decomposing the N-substituted O-substituted thiocarbamate.

[5] The method according to [1], comprising: a step (a) of separating ammonia after producing an N-substituted O-substituted thiocarbamate and ammonia by reacting the organic primary amine, the thiourea and a hydroxy compound; and a step (b) of producing an isothiocyanate by thermally decomposing the N-substituted O-substituted thiocarbamate.

[6] The method according to [2], including a step (X) of separating the compound with a thioureido group and the ammonia, further performed simultaneously with the step (1) and/or after the step (1).

[7] The method according to [4], including a step (X) of separating the compound with a thioureido group and the ammonia, further performed simultaneously with the step (A) and/or after the step (A).

[8] The method according to [4], wherein a step (Y) is performed in the step (B), the step (Y) comprising: separating as a gas phase component all or a portion of the hydroxy compound and all or a portion of the compound with a thiocarbonyl group excluding the N-substituted O-substituted thiocarbamate, along with the ammonia; and condensing the hydroxy compound and the compound with a thiocarbonyl group by introducing the gas phase component including the ammonia, the hydroxy compound and the compound with a thiocarbonyl group is introduced into a condenser, using the gas phase component.

[9] The method according to [5], wherein a step (Y) is performed in the step (a), the step (Y) comprising: separating as a gas phase component all or a portion of the hydroxy compound and all or a portion of the compound with a thiocarbonyl group excluding the N-substituted O-substituted thiocarbamate, along with the ammonia; and condensing the hydroxy compound and the compound with a thiocarbonyl group by introducing the gas phase component including the ammonia, the hydroxy compound and the compound with a thiocarbonyl group into a condenser, using the gas phase component.

[10] The method according to [8] or [9], wherein a ratio (H/T) of an amount (H) of the hydroxy compound to be condensed with respect to an amount (T) of the compound with a thiocarbonyl group to be condensed in the step (Y), is 1 or greater.

[11] The method according to [10], wherein a ratio of the number of thiocarbonyl groups with respect to the number of ammonia molecules in the gaseous mixture that has not been condensed in the step (Y) is 1 or smaller.

The following are provided as a second aspect of the invention.

[12] A composition for transporting and storing an N-substituted O-substituted thiocarbamate, comprising an N-substituted O-substituted thiocarbamate and a hydroxy compound, wherein an equivalent weight ratio of hydroxy groups of the hydroxy compound with respect to carbamate groups of the N-substituted O-substituted thiocarbamate is in the range of 1 to 100.

[13] The composition according to [12], wherein the N-substituted O-substituted thiocarbamate is an N-substituted O-substituted thiocarbamate obtained by reacting an organic primary amine, thiourea and a hydroxy compound.

[14] The composition according to [12] or [13], further comprising at least one type of compound selected from the group consisting of thiourea, N-unsubstituted O-substituted thiocarbamates, thiocarbonic acid esters, compounds with thioureido groups, dithiobiuret and dithiobiuret derivatives.

The following is provided as a third aspect of the invention.

[15] A method for producing an isothiocyanate comprising a step of obtaining an isothiocyanate by thermally decomposing the N-substituted O-substituted thiocarbamate included in the composition for transporting and storing according to any one of [12] to [14].

The following are provided as a fourth aspect of the invention.

[16] A composition for transporting and storing a compound with a thioureido group, comprising a compound with a thioureido group and a hydroxy compound, wherein an equivalent weight ratio of hydroxy groups of the hydroxy compound with respect to thioureido groups of the compound with a thioureido group is in the range of 1 to 100.

[17] The composition according to [16], further comprising at least one type of compound selected from the group consisting of thiourea, N-unsubstituted O-substituted thiocarbamates, thiocarbonic acid esters, dithiobiuret and dithiobiuret derivatives.

[18] An isothiocyanate composition containing an isothiocyanate and a compound having at least one type of functional group selected from the group consisting of groups represented by the following formula (1) and formula (2).

[Chemical Formula 1]

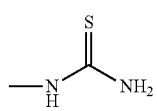

(1)

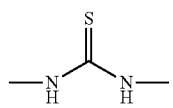

(2)

Advantageous Effects of Invention

According to the invention it is possible to produce an N-substituted O-substituted thiocarbamate using easily handleable compounds, and there is provided an isothiocyanate production method by thermal decomposition of the N-substituted O-substituted thiocarbamate. According to the invention there is also provided a composition including a compound with a thioureido group that is suitable for production of an N-substituted O-substituted thiocarbamate in the aforementioned production method, a composition including an N-substituted O-substituted thiocarbamate that is suitable for production of an isothiocyanate by thermal decomposition of the N-substituted O-substituted thiocarbamate, and an isothiocyanate composition with minimal coloration.

DESCRIPTION OF EMBODIMENTS

Figure 1:
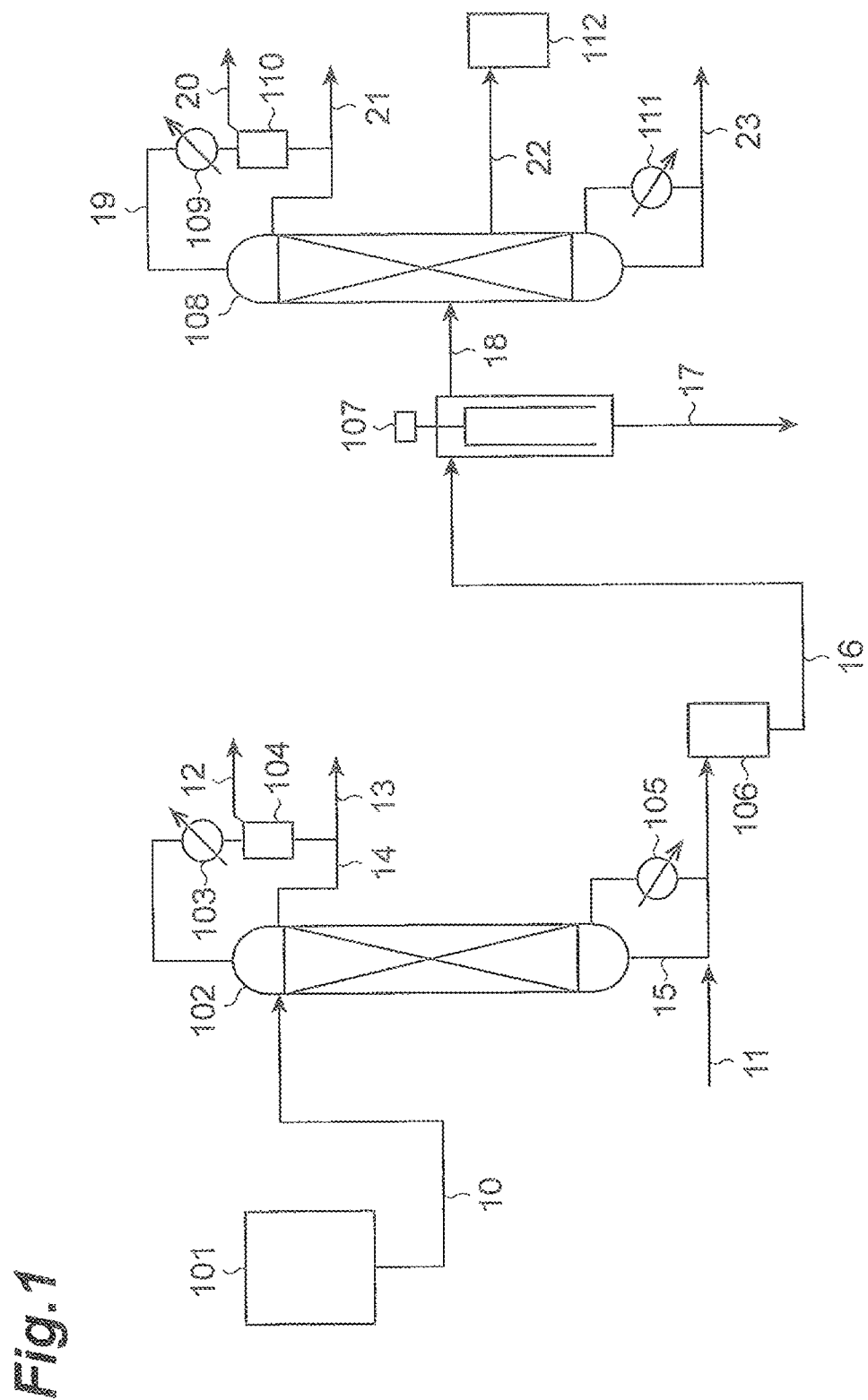
FIG. 1 is a conceptual drawing showing an example of a production apparatus for an N-substituted O-substituted thiocarbamate.

Preferred modes for carrying out the invention (hereunder, "embodiments") will now be described in detail. The invention is not limited to the described embodiments, and may be carried out with various modifications such as are within the scope of the gist thereof.

The compounds to be used for this embodiment will be described first.

<Organic Primary Amine>

The organic primary amine used is preferably an organic primary amine as represented by the following formula (3).

[Chemical Formula 2]

$$R^1\text{-}(NH_2)_n \quad (3)$$

In the formula, $R^1$ represents one group selected from the group consisting of C1 to 22 saturated aliphatic groups or C6 to 22 aromatic groups, the group optionally including an oxygen atom and/or nitrogen atom, and n representing an integer of 1 to 10.

In formula (3), groups preferred for $R^1$ include straight-chain hydrocarbon groups such as methylene, dimethylene, trimethylene, tetramethylene, pentamethylene, hexamethylene and octamethylene; unsubstituted alicyclic hydrocarbon-derived groups such as cyclopentane, cyclohexane, cycloheptane, cyclooctane and bis(cyclohexyl)alkanes; alkyl-substituted cyclohexane-derived groups such as methylcyclopentane, ethylcyclopentane, methylcyclohexane (and its various isomers), ethylcyclohexane (and its various isomers), propylcyclohexane (and its various isomers), butylcyclohexane (and its various isomers), pentylcyclohexane (and its various isomers) and hexylcyclohexane (and its various isomers); dialkyl-substituted cyclohexane-derived groups such as dimethylcyclohexane (and its various isomers), diethylcyclohexane (and its various isomers) and dibutylcyclohexane (and its various isomers); trialkyl-substituted cyclohexane-derived groups such as 1,5,5-trimethylcyclohexane, 1,5,5-triethylcyclohexane, 1,5,5-tripropylcyclohexane (and its various isomers) and 1,5,5-tributylcyclohexane (and its various isomers); monoalkyl-substituted benzenes such as toluene, ethylbenzene and propylbenzene; dialkyl-substituted benzenes such as xylene, diethylbenzene and dipropylbenzene; and aromatic hydrocarbon-derived groups such as diphenylalkanes and benzene.

Preferred among these are hexane, benzene, diphenylmethane, toluene, cyclohexane, xylenyl, methylcyclohexane, isophorone and dicyclohexylmethane-derived groups. The term "derived group" refers to a group having a structure in which n number of hydrogens have been removed from the compound (where n has the same definition as n in formula (3)).

As organic primary amines represented by formula (3) there may be used, preferably, organic primary polyamines wherein n is 2 or greater, and even more preferably organic primary diamines wherein n is 2 or 3.

Examples of organic primary amines include aliphatic amines such as butylamine, octylamine and allylamine, aromatic amines such as aniline, methylaniline and vinylaniline, aliphatic diamines such as hexamethylenediamine, 4,4'-methylenebis(cyclohexylamine) (and its various isomers), cyclohexanediamine (and its various isomers) and 3-aminomethyl-3,5,5-trimethylcyclohexylamine (and its various isomers), aromatic diamines such as phenylenediamine (and its various isomers), toluenediamine (and its various isomers) and 4,4'-methylenedianiline, and polyamines such as polyvinylamine, polyallylamine and polyvinylaniline. Preferred among these are aliphatic diamines such as hexamethylenediamine, 4,4'-methylenebis(cyclohexylamine) (and its various isomers), cyclohexanediamine (and its various isomers) and 3-aminomethyl-3,5,5-trimethylcyclohexylamine, aliphatic triamines such as tris(aminoethyl)amine (and its various isomers) and alcohol amines such as aminoethyl alcohol (and its various isomers), and more preferred among these are hexamethylenediamine, 4,4'-methylenebis(cyclohexylamine) and 3-aminomethyl-3,5,5-trimethylcyclohexylamine.

<Hydroxy Compound: Alcohol>

The hydroxy compound is an alcohol or aromatic hydroxy compound, and when it is an alcohol it is a compound represented by the following formula (4).

[Chemical Formula 3]

$$R^2\text{-}(OH)_a \quad (4)$$

In the formula, $R^2$ represents a C1 to 50 aliphatic group substituted with (a) number of hydroxy groups, or a C7 to 50 aliphatic group substituted with (a) number of hydroxy groups and aromatic groups, where (a) represents an integer of 1 to 3.

$R^2$ may be methyl, ethyl, propyl, butyl, pentyl, hexyl, heptyl, octyl, nonyl, decyl, dodecyl, octadecyl, cyclopentane, cyclohexane, cycloheptane, cyclooctane, methylcyclopentane, ethylcyclopentane, methylcyclohexane, ethylcyclohexane, propylcyclohexane, butylcyclohexane, pentylcyclohexane, hexylcyclohexane, dimethylcyclohexane, diethylcyclohexane, dibutylcyclohexane or the like.

Specific examples of alcohols having such $R^2$ groups include methanol, ethanol, propanol, butanol, pentanol, hexanol, heptanol, octanol, nonanol, decanol, dodecanol, octadecanol, cyclopentanol, cyclohexanol, cycloheptanol, cyclooctanol, methylcyclopentanol, ethylcyclopentanol, methylcyclohexanol, ethylcyclohexanol, propylcyclohexanol, butylcyclohexanol, pentylcyclohexanol, hexylcyclohexanol, dimethylcyclohexanol, diethylcyclohexanol, dibutylcyclohexanol, ethylene glycol, propylene glycol, trimethylene glycol, butanediol, pinacol, glycerol, pentaglycerol, pentaerythritol, methoxyethanol, butylcellosolve and the like.

$R^2$ may yet also be phenylmethyl, phenylethyl, phenylpropyl, phenylbutyl, phenylpentyl, phenylhexyl, phenylheptyl, phenyloctyl, phenylnonyl or the like.

Specific examples of alcohols having such $R^2$ groups include phenylmethanol, phenylethanol, phenylpropanol, phenylbutanol, phenylpentanol, phenylhexanol, phenylheptanol, phenyloctanol, phenylnonanol and the like.

Of these alcohols, in consideration of industrial use, alcohols having 1 or 2 alcoholic hydroxy groups (hydroxy groups composing the hydroxy compound and directly added to a carbon atom other than those of the aromatic ring) are preferred because they generally have low viscosity, and monoalcohols having one alcoholic hydroxy group are more preferred.

Of these, C1 to 20 alkyl alcohols are preferred from the viewpoint of ready availability, solubility of the starting materials and products, and the like.

<Hydroxy Compound: Aromatic Hydroxy Compound>

When the hydroxy compound is an aromatic hydroxy compound, the hydroxy compound is a compound represented by the following formula (5).

[Chemical Formula 4]

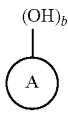

(5)

In the formula, ring A represents an organic group including 6 to 50 carbon atoms comprising an aromatic group substituted with (b) number of hydroxy groups at any position that maintains aromaticity, and it may be monocyclic, polycyclic or heterocyclic and optionally substituted with another substituent, with (b) representing an integer of 1 to 6.

Preferably, ring A is a structure comprising at least one structure selected from the group consisting of a benzene ring, naphthalene ring and anthracene ring, and more preferably ring A is a structure comprising at least one benzene ring.

The hydroxy group bonded to the ring A aromatic group is a hydroxy group bonded to a carbon atom of the ring A aromatic group, the number of such hydroxy groups being an integer of 1 to 6, preferably 1 to 3, more preferably 1 to 2 and even more preferably one (that is, b=1). More preferably, it is an aromatic monohydroxy compound with one aromatic hydroxyl group.

Specifically there may be mentioned phenol, methylphenol (and its various isomers), ethylphenol (and its various isomers), propylphenol (and its various isomers), butylphenol (and its various isomers), pentylphenol (and its various isomers), hexylphenol (and its various isomers), octylphenol (and its various isomers), nonylphenol (and its various isomers), cumylphenol (and its various isomers), dimethylphenol (and its various isomers), methylethylphenol (and its various isomers), methylpropylphenol (and its various isomers), methylbutylphenol (and its various isomers), methylpentylphenol (and its various isomers), diethylphenol (and its various isomers), ethylpropylphenol (and its various isomers), ethylbutylphenol (and its various isomers), dipropylphenol (and its various isomers), dicumylphenol (and its various isomers), trimethylphenol (and its various isomers), triethylphenol (and its various isomers), naphthol (and its various isomers), and the like.

As aromatic hydroxy compounds there are preferred compounds having one hydroxyl group directly bonded to the aromatic hydrocarbon ring composing the aromatic hydroxy compound. An aromatic hydroxy compound having two or more hydroxyl groups directly bonded to the aromatic hydrocarbon ring composing the aromatic hydroxy compound may also be used as the aromatic hydroxy compound, but since compounds with a single hydroxy group generally have low viscosity, there is preferably only one hydroxyl group.

<Compound with Thioureido Group>

The compound with a thioureido group is a compound produced by any of several methods for producing isothiocyanates using an organic primary amine and thiourea.

The compound with a thioureido group is a compound represented by the following formula (6), for example.

[Chemical Formula 5]

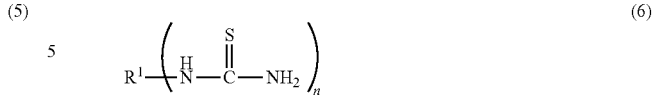

(6)

In the formula, $R^1$ represents a group as defined in formula (3), and n represents an integer as defined in formula (3).

Preferred compounds with thioureido groups include N-phenylurea, N-(methylphenyl)urea (and its various isomers), N-(dimethylphenyl)urea (and its various isomers), N-(diethylphenyl)urea (and its various isomers), N-(dipropylphenyl)urea (and its various isomers), N-naphthylurea (and its various isomers), N-(methylnaphthyl)urea (and its various isomers), N-dimethylnaphthylurea (and its various isomers), N-trimethylnaphthylurea (and its various isomers), N,N'-phenylenediurea (and its various isomers), N,N'-methylphenylenediurea (and its various isomers), N,N'-methylenediphenylenediurea (and its various isomers), N,N'-mesitylenediurea (and its various isomers), N,N'-biphenylenediurea (and its various isomers), N,N'-diphenylenediurea (and its various isomers), N,N'-propylenediphenylenediurea (and its various isomers), N,N'-oxy-diphenylenediurea (and its various isomers), bis(ureidophenoxyethane) (and its various isomers), N,N'-xylenediurea (and its various isomers), N,N'-methoxyphenyldiurea (and its various isomers), N,N'-ethoxyphenyldiurea (and its various isomers), N,N'-naphthalenediurea (and its various isomers), N,N'-methylnaphthalenediurea (and its various isomers), N-aliphatic diureas such as N,N'-ethylenediurea, N,N'-propylenediurea (and its various isomers), N,N'-butylenediurea (and its various isomers), N,N'-pentamethylenediurea (and its various isomers), N,N'-hexanemethylenediurea (and its various isomers) and N,N'-decamethylenediurea (and its various isomers); N-aliphatic triureas such as N,N',N''-hexamethylenetriurea (and its various isomers), N,N',N''-nonamethylenetriurea (and its various isomers) and N,N,N''-decamethylenetriurea (and its various isomers); and substituted N-cycloaliphatic polyureas such as N,N-cyclobutylenediurea (and its various isomers), N,N'-methylenedicyclohexyldiurea (and its various isomers), 3-ureidomethyl-3,5,5-trimethylcyclohexylurea (cis and/or transform) and methylenebis(cyclohexylureaXand its various isomers).

<N-Substituted O-Substituted Thiocarbamate>

The N-substituted O-substituted thiocarbamate is a compound produced using an organic primary amine, thiourea and a hydroxy compound, among the different isothiocyanate production methods described below. When an alcohol is used as the hydroxy compound, it is an N-substituted O-substituted thiocarbamate represented by the following formula (7).

[Chemical Formula 6]

(7)

In the formula, $R^1$ represents a group as defined in formula (3), $R^3$ is a group derived from an alcohol, being a residue remaining after removing from the alcohol one hydroxy group bonded to a saturated carbon atom of the alcohol, and n represents an integer as defined in formula (3).

Since the specific structure of the N-substituted O-substituted thiocarbamate will be determined by the type of organic primary amine and alcohol used, a complete list cannot be given, but the following compounds may be mentioned as examples.

N,N'-Hexanediyl-di(thiocarbamic acid methyl ester) (and its various isomers), N,N'-hexanediyl-di(thiocarbamic acid ethyl ester) (and its various isomers), N,N'-hexanediyl-di(thiocarbamic acid propyl ester) (and its various isomers), N,N'-hexanediyl-di(thiocarbamic acid butyl ester) (and its various isomers), N,N'-hexanediyl-di(thiocarbamic acid pentyl ester) (and its various isomers), N,N'-hexanediyl-di(thiocarbamic acid hexyl ester) (and its various isomers), N,N'-hexanediyl-di(thiocarbamic acid heptyl ester) (and its various isomers), N,N'-hexanediyl-di(carbamic acid octyl ester) (and its various isomers), N,N'-hexanediyl-di(thiocarbamic acid nonyl ester) (and its various isomers), N,N'-hexanediyl-di(thiocarbamic acid decyl ester) (and its various isomers), N,N'-hexanediyl-di(carbamic acid dodecyl ester) (and its various isomers), N,N'-hexanediyl-di(thiocarbamic acid octadecyl ester) (and its various isomers), N,N-methylenediphenylene-di(thiocarbamic acid methyl ester) (and its various isomers), N,N-methylenediphenylene-di(thiocarbamic acid ethyl ester) (and its various isomers), N,N'-methylenediphenylene-di(thiocarbamic acid propyl ester) (and its various isomers), N,N-methylenediphenylene-di(thiocarbamic acid butyl ester) (and its various isomers), N,N'-methylenediphenylene-di(thiocarbamic acid pentyl ester) (and its various isomers), N,N-methylenediphenylene-di(thiocarbamic acid hexyl ester) (and its various isomers), N,N'-methylenediphenylene-di(thiocarbamic acid heptyl ester) (and its various isomers), N,N-methylenediphenylene-di(thiocarbamic acid octyl ester) (and its various isomers), N,N-methylenediphenylene-di(thiocarbamic acid nonyl ester) (and its various isomers), N,N-methylenediphenylene-di(thiocarbamic acid decyl ester) (and its various isomers), N,N'-methylenediphenylene-di(thiocarbamic acid dodecyl ester) (and its various isomers) and N,N-methylenediphenylene-di(thiocarbamic acid octadecyl ester) (and its various isomers);

3-(Methoxythiocarbonylamino-methyl)-3,5,5-trimethylcyclohex ylthiocarbamic acid methyl ester (and its various isomers), 3-(ethoxythiocarbonylamino-methyl)-3,5,5-trimethylcyclohexylthiocarb amic acid ethyl ester (and its various isomers), 3-(propyloxythiocarbonylamino-methyl)-3,5,5-trimethylcyclohexylthioc arbamic acid propyl ester (and its various isomers), 3-(butyloxythiocarbonylamino-methyl)-3,5,5-trimethylcyclohexylthioca rbamic acid butyl ester (and its various isomers), 3-(pentyloxythiocarbonylamino-methyl)-3,5,5-trimethylcyclohexylthioc arbamic acid pentyl ester (and its various isomers), 3-(hexyloxythiocarbonylamino-methyl)-3,5,5-trimethylcyclohexylthioc arbamic acid hexyl ester (and its various isomers), 3-(heptyloxythiocarbonylamino-methyl)-3,5,5-trimethylcyclohexylthioc arbamic acid heptyl ester (and its various isomers), 3-(octyloxythiocarbonylamino-methyl)-3,5,5-trimethylcyclohexylthioca rbamic acid octyl ester (and its various isomers), 3-(nonyloxythiocarbonylamino-methyl)-3,5,5-trimethylcyclohexylthioc arbamic acid nonyl ester (and its various isomers), 3-(decyloxythiocarbonylamino-methyl)-3,5,5-trimethylcyclohexylthioca rbamic acid decyl ester (and its various isomers), 3-(dodecyloxythiocarbonylamino-methyl)-3,5,5-trimethylcyclohexylthi ocarbamic acid dodecyl ester (and its various isomers) and 3-(octadecyloxythiocarbonylamino-methyl)-3,5,5-trimethylcyclohexylth iocarbamic acid octadecyl ester (and its various isomers);

Toluene-di(thiocarbamic acid methyl ester) (and its various isomers), toluene-di(thiocarbamic acid ethyl ester) (and its various isomers), toluene-di(thiocarbamic acid propyl ester) (and its various isomers), toluene-di(thiocarbamic acid butyl ester) (and its various isomers), toluene-di(thiocarbamic acid pentyl ester) (and its various isomers), toluene-di(thiocarbamic acid hexyl ester) (and its various isomers), toluene-di(thiocarbamic acid heptyl ester) (and its various isomers), toluene-di(thiocarbamic acid octyl ester) (and its various isomers), toluene-di(thiocarbamic acid nonyl ester) (and its various isomers), toluene-di(thiocarbamic acid decyl ester) (and its various isomers), toluene-di(thiocarbamic acid dodecyl ester) (and its various isomers), toluene-di(thiocarbamic acid octadecyl ester) (and its various isomers), N,N'-methylenedicyclohexyl-di(thiocarbamic acid methyl ester) (and its various isomers), N,N'-methylenedicyclohexyl-di(thiocarbamic acid ethyl ester) (and its various isomers), N,N'-methylenedicyclohexyl-di(thiocarbamic acid propyl ester) (and its various isomers), N,N'-methylenedicyclohexyl-di(thiocarbamic acid butyl ester) (and its various isomers), N,N'-methylenedicyclohexyl-di(thiocarbamic acid pentyl ester) (and its various isomers), N,N'-methylenedicyclohexyl-di(thiocarbamic acid hexyl ester) (and its various isomers), N,N'-methylenedicyclohexyl-di(thiocarbamic acid heptyl ester) (and its various isomers), N,N'-methylenedicyclohexyl-di(thiocarbamic acid octyl ester) (and its various isomers), N,N'-methylenedicyclohexyl-di(thiocarbamic acid nonyl ester) (and its various isomers), N,N'-methylenedicyclohexyl-di(thiocarbamic acid decyl ester) (and its various isomers), N,N'-methylenedicyclohexyl-di(thiocarbamic acid dodecyl ester) (and its various isomers) and N,N'-methylenedicyclohexyl-di(thiocarbamic acid octadecyl ester) (and its various isomers);

N-Phenylthiocarbamic acid methyl ester (and its various isomers), N-phenylthiocarbamic acid ethyl ester (and its various isomers), N-phenylthiocarbamic acid propyl ester (and its various isomers), N-phenylthiocarbamic acid butyl ester (and its various isomers), N-phenylthiocarbamic acid pentyl ester (and its various isomers), N-phenylthiocarbamic acid (hexyl ester) (and its various isomers), N-phenylthiocarbamic acid heptyl ester (and its various isomers), N-phenylthiocarbamic acid octyl ester (and its various isomers), N-phenylthiocarbamic acid nonyl ester (and its various isomers), N-phenylthiocarbamic acid decyl ester (and its various isomers), N-phenylthiocarbamic acid dodecyl ester (and its various isomers), N-phenylthiocarbamic acid octadecyl ester (and its various isomers), N-dimethylthiophenylcarbamic acid methyl ester (and its various isomers), N-dimethylphenylthiocarbamic acid ethyl ester (and its various isomers), N-dimethylphenylthiocarbamic acid propyl ester (and its various isomers), N-dimethylphenylthiocarbamic acid butyl ester (and its various isomers), N-dimethylphenylthiocarbamic acid pentyl ester (and its various isomers), N-dimethylphenylthiocarbamic acid hexyl ester (and its various isomers), N-dimethylphenylthiocarbamic acid heptyl ester (and its various isomers), N-dimethylphenylthiocarbamic acid octyl ester (and its various isomers), N-dimethylphenylthiocarbamic acid nonyl ester (and its various isomers), N-dimethylphenylthiocarbamic acid decyl ester (and its various isomers), N-dimethylphenylthiocarbamic acid dodecyl ester (and its various isomers) and N-dimethylphenylthiocarbamic acid octadecyl ester (and its various isomers).

When an aromatic hydroxy compound is used as the hydroxy compound, on the other hand, it is an N-substituted O-substituted thiocarbamate represented by the following formula (8).

[Chemical Formula 7]

(8)

In the formula, $R^1$ represents a group as defined in formula (3), Ar is a group derived from an aromatic hydroxy compound, being a residue remaining after removing from the aromatic hydroxy compound one hydroxy group bonded to an aromatic ring of the aromatic hydroxy compound, and n represents an integer as defined in formula (1).

Since the specific structure of the N-substituted O-substituted thiocarbamate represented by formula (8) will be determined by the type of organic primary amine and aromatic hydroxy compound used, a complete list cannot be given, but the following compounds may be mentioned as examples.

N,N'-Hexanediyl-di(thiocarbamic acid phenyl ester), N,N'-hexanediyl-di(thiocarbamic acid (methylphenyl) ester) (and its various isomers), N,N'-hexanediyl-di(thiocarbamic acid (ethylphenyl) ester) (and its various isomers), N,N'-hexanediyl-di(thiocarbamic acid (propylphenyl) ester) (and its various isomers), N,N'-hexanediyl-di(thiocarbamic acid (butylphenyl) ester) (and its various isomers), N,N'-hexanediyl-di(thiocarbamic acid (pentylphenyl) ester) (and its various isomers), N,N'-hexanediyl-di(thiocarbamic acid (hexylphenyl) ester) (and its various isomers), N,N'-hexanediyl-di(thiocarbamic acid (heptylphenyl) ester) (and its various isomers), N,N'-hexanediyl-di(thiocarbamic acid (octylphenyl) ester) (and its various isomers), N,N'-hexanediyl-di(thiocarbamic acid (nonylphenyl) ester) (and its various isomers), N,N'-hexanediyl-di(thiocarbamic acid (decylphenyl) ester) (and its various isomers), N,N-hexanediyl-di(thiocarbamic acid (dodecylphenyl) ester) (and its various isomers), N,N-hexanediyl-di(thiocarbamic acid (octadecylphenyl) ester) (and its various isomers), N,N'-hexanediyl-bis(thiocarbamic acid (dimethylphenyl) ester) (and its various isomers), N,N-hexanediyl-bis(thiocarbamic acid (diethylphenyl) ester) (and its various isomers), N,N'-hexanediyl-bis(thiocarbamic acid (dipropylphenyl) ester) (and its various isomers), N,N-hexanediyl-bis(thiocarbamic acid (dibutylphenyl) ester) (and its various isomers), N,N'-hexanediyl-bis(thiocarbamic acid (dipentylphenyl) ester) (and its various isomers), N,N-hexanediyl-bis(thiocarbamic acid (dihexylphenyl) ester) (and its various isomers), N,N'-hexanediyl-bis(thiocarbamic acid (diheptylphenyl) ester) (and its various isomers), N,N-hexanediyl-bis(thiocarbamic acid (dioctylphenyl) ester) (and its various isomers), N,N'-hexanediyl-bis(thiocarbamic acid (dinonylphenyl) ester) (and its various isomers), N,N-hexanediyl-bis(thiocarbamic acid (didecylphenyl) ester) (and its various isomers), N,N'-hexanediyl-bis(thiocarbamic acid (didodecylphenyl) ester) (and its various isomers) and N,N'-hexanediyl-bis(thiocarbamic acid (dioctadecylphenyl) ester) (and its various isomers);

N,N'-Methylenediphenylene-di(thiocarbamic acid phenyl ester) (and its various isomers), N,N'-methylenediphenylene-di(thiocarbamic acid (methylphenyl) ester) (and its various isomers), N,N'-methylenediphenylene-di(thiocarbamic acid (ethylphenyl) ester) (and its various isomers), N,N'-methylenediphenylene-di(thiocarbamic acid (propylphenyl) ester) (and its various isomers), N,N'-methylenediphenylene-di(thiocarbamic acid (butylphenyl) ester) (and its various isomers), N,N'-methylenediphenylene-di(thiocarbamic acid (pentylphenyl) ester) (and its various isomers), N,N'-methylenediphenylene-di(thiocarbamic acid (hexylphenyl) ester) (and its various isomers), N,N'-methylenediphenylene-di(thiocarbamic acid (heptylphenyl) ester) (and its various isomers), N,N-methylenediphenylene-di(thiocarbamic acid (octylphenyl) ester) (and its various isomers), N,N'-methylenediphenylene-di(thiocarbamic acid (nonylphenyl) ester) (and its various isomers), N,N-methylenediphenylene-di(thiocarbamic acid (decylphenyl) ester) (and its various isomers), N,N'-methylenediphenylene-di(thiocarbamic acid (dodecylphenyl) ester) (and its various isomers), N,N-methylenediphenylene-di(thiocarbamic acid (octadecylphenyl) ester) (and its various isomers), N,N-methylenediphenylene-bis(thiocarbamic acid (dimethylphenyl) ester) (and its various isomers), N,N-methylenediphenylene-bis(thiocarbamic acid (diethylphenyl) ester) (and its various isomers), N,N'-methylenediphenylene-bis(thiocarbannic acid (dipropylphenyl) ester) (and its various isomers), N,N-methylenediphenylene-bis(thiocarbamic acid (dibutylphenyl) ester) (and its various isomers), N,N-methylenediphenylene-bis(thiocarbamic acid (dipentylphenyl) ester) (and its various isomers), N,N-methylenediphenylene-bis(thiocarbamic acid (dihexylphenyl) ester) (and its various isomers), N,N-methylenediphenylene-bis(thiocarbamic acid (diheptylphenyl) ester) (and its various isomers), N,N-methylenediphenylene-bis(thiocarbamic acid (dioctylphenyl) ester) (and its various isomers), N,N-methylenediphenylene-bis(thiocarbamic acid (dinonylphenyl) ester) (and its various isomers), N,N-methylenediphenylene-bis(thiocarbamic acid (didecylphenyl) ester) (and its various isomers), N,N-methylenediphenylene-bis(thiocarbamic acid (didodecylphenyl) ester) (and its various isomers) and N,N-methylenediphenylene-bis(thiocarbamic acid (dioctadecylphenyl) ester) (and its various isomers);

3-(Phenoxythiocarbonylamino-methyl)-3,5,5-trimethylcyclohex ylthiocarbamic acid phenyl ester, 3-((methylphenoxy)thiocarbonylamino-methyl)-3,5,5-trimethylcyclohex ylthiocarbamic acid (methylphenyl) ester (and its various isomers), 3-((ethylphenoxy)thiocarbonylamino-methyl)-3,5, 5-trimethylcyclohexyl thiocarbamic acid (ethylphenyl) ester (and its various isomers), 3-((propylphenoxy)thiocarbonylamino-methyl)-3,5,5-trimethylcyclohex ylthiocarbamic acid (propylphenyl) ester (and its various isomers), 3-((butylphenoxy)thiocarbonylamino-methyl)-3,5,5-trimethylcyclohexy lthiocarbamic acid (butylphenyl) ester (and its various isomers), 3-((pentylphenoxy)thiocarbonylamino-methyl)-3,5,5-trimethylcyclohex ylthiocarbamic acid (pentylphenyl) ester (and its various isomers), 3-((hexylphenoxy)thiocarbonylamino-methyl)-3,5,5-trimethylcyclohexy lthiocarbamic acid (hexylphenyl) ester (and its various isomers), 3-((heptylphenoxy)thiocarbonylamino-methyl)-3,5, 5-trimethylcyclohex ylthiocarbamic acid (heptylphenyl) ester (and its various isomers), 3-((octylphenoxy)thiocarbonylamino-methyl)-3,5,5-trimethylcyclohexyl thiocarbamic acid (octylphenyl) ester (and its various isomers), 3-((nonylphenoxy)thiocarbonylamino-methyl)-3,5,5-trimethylcyclohexy lthiocarbamic acid (nonylphenyl) ester (and its various isomers), 3-((decylphenoxy)thiocarbonylamino-methyl)-3,5,5-trimethylcyclohexy lthiocarbamic acid (decylphenyl) ester (and its various isomers), 3-((dodecylphenoxy)thiocarbonylamino-methyl)-3,5,5-trimethylcyclohe xylthiocarbamic acid (dodecylphenyl) ester (and its various isomers), 3-((octadecylphenoxy)thiocarbonylamino-methyl)-3,5,5-trimethylcyclo hexylthiocarbamic acid (octadecylphenyl) ester (and its various isomers), 3-((dimethylphenoxy)thiocarbonylamino-methyl)-3,5,5-trimethylcycloh exylthiocarbamic acid (dimethylphenoxy) ester (and its various isomers), 3-((diethylphenoxy)thiocarbonylamino-methyl)-3,5,5-trimethylcyclohex ylthiocarbamic acid (diethylphenyl) ester (and its various isomers), 3-((dipropylphenoxy)thiocarbonylamino-methyl)-3,5,5-trimethylcycloh exylthiocarbamic acid (dipropylphenyl) ester (and its various isomers), 3-((dibutylphenoxy)thiocarbonylamino-methyl)-3,5,5-trimethylcyclohe xylthiocarbamic acid (dibutylphenyl) ester (and its various isomers), 3-((dipentylphenoxy)thiocarbonylamino-methyl)-3,5,5-trimethylcyclohe xylthiocarbamic acid (dipentylphenyl) ester (and its various isomers), 3-((dihexylphenoxy)thiocarbonylamino-methyl)-3,5,5-trimethylcyclohe xylthiocarbamic acid (dihexylphenyl) ester (and its various isomers), 3-((diheptylphenoxy)thiocarbonylamino-methyl)-3,5,5-trimethylcyclohe xylthiocarbamic acid (diheptylphenyl) ester (and its various isomers), 3-((dioctylphenoxy)thiocarbonylamino-methyl)-3,5,5-trimethylcyclohex ylthiocarbamic acid (dioctylphenyl) ester (and its various isomers), 3-((dinonylphenoxy)thiocarbonylamino-methyl)-3,5,5-trimethylcyclohe xylthiocarbamic acid (dinonylphenyl) ester (and its various isomers), 3-((didecylphenoxy)thiocarbonylamino-methyl)-3,5,5-trimethylcyclohe xylthiocarbamic acid (didecylphenyl) ester (and its various isomers), 3-((didodecylphenoxy)thiocarbonylamino-methyl)-3,5,5-trimethylcyclo hexylthiocarbamic acid (didodecylphenyl) ester (and its various isomers) and 3-((dioctadecylphenoxy)thiocarbonylamino-methyl)-3,5,5-trimethylcycl ohexylthiocarbamic acid (dioctadecylphenyl) ester (and its various isomers);

Toluene-di(thiocarbamic acid phenyl ester) (and its various isomers), toluene-di(thiocarbamic acid (methylphenyl) ester) (and its various isomers), toluene-di(thiocarbamic acid ethylphenyl) ester) (and its various isomers), toluene-di(thiocarbamic acid (propylphenyl) ester) (and its various isomers), toluene-di(thiocarbamic acid (butylphenyl) ester) (and its various isomers), toluene-di(thiocarbamic acid (pentylphenyl) ester) (and its various isomers), toluene-di(thiocarbamic acid (hexylphenyl) ester) (and its various isomers), toluene-di(thiocarbamic acid (heptylphenyl) ester) (and its various isomers), toluene-di(thiocarbamic acid (octylphenyl) ester) (and its various isomers), toluene-di(thiocarbamic acid (nonylphenyl) ester) (and its various isomers), toluene-di(thiocarbamic acid (decylphenyl) ester) (and its various isomers), toluene-di(thiocarbamic acid (dodecylphenyl) ester) (and its various isomers), toluene-di(thiocarbamic acid (octadecylphenyl) ester) (and its various isomers), toluene-bis(thiocarbamic acid (dimethylphenyl) ester) (and its various isomers), toluene-bis(thiocarbamic acid (diethylphenyl) ester) (and its various isomers), toluene-bis(thiocarbamic acid (dipropylphenyl) ester) (and its various isomers), toluene-bis(thiocarbamic acid (dibutylphenyl) ester) (and its various isomers), toluene-bis(thiocarbamic acid (dipentylphenyl) ester) (and its various isomers), toluene-bis(thiocarbamic acid (dihexylphenyl) ester) (and its various isomers), toluene-bis(thiocarbamic acid (diheptylphenyl) ester) (and its various isomers), toluene-bis(thiocarbamic acid (dioctylphenyl) ester) (and its various isomers), toluene-bis(thiocarbamic acid (dinonylphenyl) ester) (and its various isomers), toluene-bis(thiocarbamic acid (didecylphenyl) ester) (and its various isomers), toluene-bis (thiocarbamic acid (didodecylphenyl) ester) (and its various isomers) and toluene-bis(thiocarbamic acid (dioctadecylphenyl) ester) (and its various isomers);

N,N'-Methylenedicyclohexyl-di(thiocarbamic acid phenyl ester) (and its various isomers), N,N'-methylenedicyclohexyl-di(thiocarbamic acid (methylphenyl) ester) (and its various isomers), N,N'-methylenedicyclohexyl-di(thiocarbamic acid (ethylphenyl) ester) (and its various isomers), N,N'-methylenedicyclohexyl-di(thiocarbamic acid (propylphenyl) ester) (and its various isomers), N,N'-methylenedicyclohexyl-di(thiocarbamic acid (butylphenyl) ester) (and its various isomers), N,N'-methylenedicyclohexyl-di(thiocarbamic acid (pentylphenyl) ester) (and its various isomers), N,N'-methylenedicyclohexyl-di(thiocarbamic acid (hexylphenyl) ester) (and its various isomers), N,N'-methylenedicyclohexyl-di(thiocarbamic acid (heptylphenyl) ester) (and its various isomers), N,N'-methylenedicyclohexyl-di(thiocarbamic acid (octylphenyl) ester) (and its various isomers), N,N'-methylenedicyclohexyl-di(thiocarbamic acid (nonylphenyl) ester) (and its various isomers), N,N'-methylenedicyclohexyl-di(thiocarbamic acid (decylphenyl) ester) (and its various isomers), N,N'-methylenedicyclohexyl-di(thiocarbamic acid (dodecylphenyl) ester) (and its various isomers), N,N-methylenedicyclohexyl-di(thiocarbamic acid (octadecylphenyl) ester) (and its various isomers), N,N-methylenedicyclohexyl-bis(thiocarbamic acid (dimethylphenyl) ester) (and its various isomers), N,N-methylenedicyclohexyl-bis(thiocarbamic acid (diethylphenyl) ester) (and its various isomers), N,N'-methylenedicyclohexyl-bis(thiocarbamic acid (dipropylphenyl) ester) (and its various isomers), N,N'-methylenedicyclohexyl-bis(thiocarbamic acid (dibutylphenyl) ester) (and its various isomers), N,N'-methylenedicyclohexyl-bis(thiocarbamic acid (dipentylphenyl) ester) (and its various isomers), N,N'-methylenedicyclohexyl-bis(thiocarbamic acid (dihexylphenyl) ester) (and its various isomers), N,N'-methylenedicyclohexyl-bis(thiocarbamic acid (diheptylphenyl) ester) (and its various isomers), N,N'-methylenedicyclohexyl-bis(thiocarbamic acid (dioctylphenyl) ester) (and its various isomers), N,N'-methylenedicyclohexyl-bis(thiocarbamic acid (dinonylphenyl) ester) (and its various isomers), N,N'-methylenedicyclohexyl-bis(thiocarbamic acid (didecylphenyl) ester) (and its various isomers), N,N'-methylenedicyclohexyl-bis(thiocarbamic acid (didodecylphenyl) ester) (and its various isomers) and N,N'-methylenedicyclohexyl-bis (thiocarbamic acid (dioctadecylphenyl) ester) (and its various isomers);

N-Phenylthiocarbamic acid phenyl ester, N-phenylthiocarbamic acid (methylphenyl) ester (and its various isomers), N-phenylthiocarbamic acid (ethylphenyl) ester (and its various isomers), N-phenylthiocarbamic acid (propylphenyl) ester (and its various isomers), N-phenylthiocarbamic acid (butylphenyl) ester (and its various isomers), N-phenylthiocarbamic acid (pentylphenyl) ester (and its various isomers), N-phenylthiocarbamic acid (hexylphenyl) ester (and its various isomers), N-phenylthiocarbamic acid (heptylphenyl) ester (and its various isomers), N-phenylthiocarbamic acid (octylphenyl) ester (and its various isomers), N-phenylthiocarbamic acid (nonylphenyl) ester (and its various isomers), N-phenylthiocarbamic acid (decylphenyl) ester (and its various isomers), N-phenylthiocarbamic acid (dodecylphenyl) ester (and its various isomers), N-phenylthiocarbamic acid (octadecylphenyl) ester (and its various isomers), N-phenylthiocarbamic acid (dimethylphenyl) ester (and its various isomers), N-phenylthiocarbamic acid (diethylphenyl) ester (and its various isomers), N-phenylthiocarbamic acid (dipropylphenyl) ester (and its various isomers), N-phenylthiocarbamic acid (dibutylphenyl) ester (and its various isomers), N-phenylthiocarbamic acid (dipentylphenyl) ester (and its various isomers), N-phenylthiocarbamic acid (dihexylphenyl) ester (and its various isomers), N-phenylthiocarbamic acid (diheptylphenyl) ester (and its various isomers), N-phenylthiocarbamic acid (dioctylphenyl) ester (and its various isomers), N-phenylthiocarbamic acid (dinonylphenyl) ester (and its various isomers), N-phenylthiocarbamic acid (didecylphenyl) ester (and its various isomers), N-phenylthiocarbamic acid (didodecylphenyl) ester (and its various isomers), N-phenylthiocarbamic acid (dioctadecylphenyl) ester (and its various isomers), N-phenylthiocarbamic acid phenyl ester, N-phenylthiocarbamic acid (methylphenyl) ester (and its various isomers), N-phenylthiocarbamic acid (ethylphenyl) ester (and its various isomers), N-phenylthiocarbamic acid (propylphenyl) ester (and its various isomers), N-phenylthiocarbamic acid (butylphenyl) ester (and its various isomers), N-phenylthiocarbamic acid (pentylphenyl) ester (and its various isomers), N-phenylthiocarbamic acid (hexylphenyl) ester (and its various isomers), N-phenylthiocarbamic acid (heptylphenyl) ester (and its various isomers), N-phenylthiocarbamic acid (octylphenyl) ester (and its various isomers), N-phenylthiocarbamic acid (nonylphenyl) ester (and its various isomers), N-phenylthiocarbamic acid (decylphenyl) ester (and its various isomers), N-phenylthiocarbamic acid (dodecylphenyl) ester (and its various isomers), N-phenylthiocarbamic acid (octadecylphenyl) ester (and its various isomers), N-phenylthiocarbamic acid (dimethylphenyl) ester (and its various isomers), N-phenylthiocarbamic acid (diethylphenyl) ester (and its various isomers), N-phenylthiocarbamic acid (dipropylphenyl) ester (and its various isomers), N-phenylthiocarbamic acid (dibutylphenyl) ester (and its various isomers), N-phenylthiocarbamic acid (dipentylphenyl) ester (and its various isomers), N-phenylthiocarbamic acid (dihexylphenyl) ester (and its various isomers), N-phenylthiocarbamic acid (diheptylphenyl) ester (and its various isomers), N-phenylthiocarbamic acid (dioctylphenyl) ester (and its various isomers), N-phenylthiocarbamic acid (dinonylphenyl) ester (and its various isomers), N-phenylthiocarbamic acid (didecylphenyl) ester (and its various isomers), N-phenylthiocarbamic acid (didodecylphenyl) ester (and its various isomers) and N-phenylthiocarbamic acid (dioctadecylphenyl) ester (and its various isomers);

N-Dimethylphenylthiocarbamic acid phenyl ester (and its various isomers), N-dimethylphenylthiocarbamic acid (methylphenyl) ester (and its various isomers), N-dimethylphenylthiocarbamic acid (ethylphenyl) ester (and its various isomers), N-dimethylphenylthiocarbamic acid (propylphenyl) ester (and its various isomers), N-dimethylphenylthiocarbamic acid (butylphenyl) ester (and its various isomers), N-dimethylphenylthiocarbamic acid (pentylphenyl) ester (and its various isomers), N-dimethylphenylthiocarbamic acid (hexylphenyl) ester (and its various isomers), N-dimethylphenylthiocarbamic acid (heptylphenyl) ester (and its various isomers), N-dimethylphenylthiocarbamic acid (octylphenyl) ester (and its various isomers), N-dimethylphenylthiocarbamic acid (nonylphenyl) ester (and its various isomers), N-dimethylphenylthiocarbamic acid (decylphenyl) ester (and its various isomers), N-dimethylphenylthiocarbamic acid (dodecylphenyl) ester (and its various isomers), N-dimethylphenylthiocarbamic acid (octadecylphenyl) ester (and its various isomers), N-dimethylphenylthiocarbamic acid (dimethylphenyl) ester (and its various isomers), N-dimethylphenylthiocarbamic acid (diethylphenyl) ester (and its various isomers), N-dimethylphenylthiocarbamic acid (dipropylphenyl) ester (and its various isomers), N-dimethylphenylthiocarbamic acid (dibutylphenyl) ester (and its various isomers), N-dimethylphenylthiocarbamic acid (dipentylphenyl) ester (and its various isomers), N-dimethylphenylthiocarbamic acid (dihexylphenyl) ester (and its various isomers), N-dimethylphenylthiocarbamic acid (diheptylphenyl) ester (and its various isomers), N-dimethylphenylthiocarbamic acid (dioctylphenyl) ester (and its various isomers), N-dimethylphenylthiocarbamic acid (dinonylphenyl) ester (and its various isomers), N-dimethylphenylthiocarbamic acid (didecylphenyl) ester (and its various isomers), N-dimethylphenylthiocarbamic acid (didodecylphenyl) ester (and its various isomers) and N-dimethylphenylthiocarbamic acid (dioctadecylphenyl) ester (and its various isomers).

<Isothiocyanate>

The isothiocyanate to be produced by the method of this embodiment and the isothiocyanate preferably contained in the composition of this embodiment, are compounds represented by the following formula (9).

[Chemical Formula 8]

$$R^1\!\!-\!\!(NCS)_n \qquad (9)$$

In the formula, $R^1$ represents a group as defined in formula (3), and n represents a number as defined in formula (3).

In formula (9), groups preferred for $R^1$ include straight-chain hydrocarbon groups such as methylene, dimethylene, trimethylene, tetramethylene, pentamethylene, hexamethylene and octamethylene; unsubstituted alicyclic hydrocarbon-derived groups such as cyclopentane, cyclohexane, cycloheptane, cyclooctane and bis(cyclohexyl)alkanes; alkyl-substituted cyclohexane-derived groups such as methylcyclopentane, ethylcyclopentane, methylcyclohexane (and its various isomers), ethylcyclohexane (and its various isomers), propylcyclohexane (and its various isomers), butylcyclohexane (and its various isomers), pentylcyclohexane (and its various isomers) and hexylcyclohexane (and its various isomers); dialkyl-substituted cyclohexane-derived groups such as dimethylcyclohexane (and its various isomers), diethylcyclohexane (and its various isomers) and dibutylcyclohexane (and its various isomers); trialkyl-substituted cyclohexane-derived groups such as 1,5,5-trimethylcyclohexane, 1,5,5-triethylcyclohexane, 1,5,5-tripropylcyclohexane (and its various isomers) and 1,5,5-tributylcyclohexane (and its various isomers); monoalkyl-substituted benzenes such as toluene, ethylbenzene and propylbenzene; dialkyl-substituted benzenes such as xylene, diethylbenzene and dipropylbenzene; and aromatic hydrocarbon-derived groups such as diphenylalkanes and benzene.

Preferred among these are hexane, benzene, diphenylmethane, toluene, cyclohexane, xylenyl, methylcyclohexane, isophorone and dicyclohexylmethane-derived groups. The term "derived group" refers to a group having a structure in which n number of hydrogens have been removed from the compound. The letter n here has the same definition as n in formula (3).

Examples of isothiocyanates include aliphatic isothiocyanates such as butyl isothiocyanate, octyl isothiocyanate and allyl isothiocyanate, aliphatic diisothiocyanates such as hexamethylene diisothiocyanate, 4,4'-methylenebis(cyclohexyl isothiocyanate) (and its various isomers), cyclohexane diisothiocyanate (and its various isomers) and 3-isothiocyanatomethyl-3,5,5-trimethylcyclohexyl isothiocyanate; aromatic diisothiocyanates such as phenylene diisothiocyanate (and its various isomers), toluene diisothiocyanate (and its various isomers) and 4,4'-methylene di(phenylisothiocyanate), and polyisothiocyanates such as polyvinyl isothiocyanate, polyallyl isothiocyanate and polyvinyl (phenylisothiocyanate). Among these it is preferred to use aliphatic diisothiocyanates such as hexamethylene diisothiocyanate, 4,4'-methylenebis(cyclohexyl isothiocyanate) (and its various isomers), cyclohexane diisothiocyanate (and its various isomers) and 3-isothiocyanatomethyl-3,5,5-trimethylcyclohexyl isothiocyanate, with hexamethylene diisothiocyanate, 4,4'-methylenebis(cyclohexyl isothiocyanate) and 3-isothiocyanatomethyl-3,5,5-trimethylcyclohexyl isothiocyanate being more preferred.

[Isothiocyanate Production Method]

An isothiocyanate production method will now be described. In the method of this embodiment, an isothiocyanate is produced using an organic primary amine and thiourea as starting materials, and several preferred methods exist. These methods will now be described.

<First Method>

The first method is a method including the following step (1) and step (2).

Step (1): A step of reacting an organic primary amine and thiourea to produce a compound with a thioureido group and ammonia.

Step (2): A step of thermally decomposing the compound with a thioureido group and separating the isothiocyanate and ammonia that are produced.

Step (1) is a step of reacting an organic primary amine and thiourea to produce a compound with a thioureido group and ammonia, as a step in which the reaction represented by the following formula (10) is carried out.

[Chemical Formula 9]

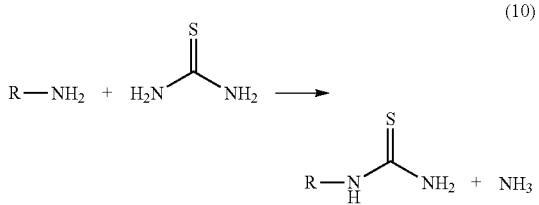

(10)

In the formula, R represents an organic group.

The description is of the reaction of formula (10) wherein a monofunctional organic primary amine has been used, but it will be readily appreciated by a person skilled in the art that the same reaction proceeds even when using a polyfunctional organic primary amine.

The amount of thiourea may be in the range of 1- to 100-fold as the stoichiometric ratio with respect to the amino groups of the organic primary amine. When a low amount of thiourea is used there will be a tendency toward production of complex-substituted thiocarbonyl compounds and the like, and it is therefore preferred to use an excess of thiourea, but using a large excess of thiourea can conversely also tend toward production of complex-substituted thiocarbonyl compounds, or result in persistence of unreacted thiourea, necessitating a great deal of effort for separation and recovery of the thiourea (described below). Thus, the amount of thiourea is in the range of preferably 1.1- to 10-fold and more preferably 1.5- to 5-fold as the stoichiometric ratio with respect to the amino groups of the organic primary amine.

The reaction temperature will depend on the reactivity of the organic primary amine and thiourea used, but it is preferably in the range of 100° C. to 300° C. At a temperature lower than 100° C., the reaction may be slowed or the reaction may essentially not take place, or the amount of complex-substituted thiocarbonyl compounds may increase. At a temperature higher than 300° C., on the other hand, the thiourea may decompose, the hydroxy compound may undergo dehydrogenating modification, or the N-substituted O-substituted thiocarbamate product may tend to undergo decomposition reaction, alteration reaction or the like. From this viewpoint, a more preferred temperature range is 120° C. to 280° C., and an even more preferred range is 140° C. to 250° C.

The reaction pressure will differ depending on the composition of the reaction system, the reaction temperature, the method of removing ammonia, the reactor used and the like, and it may be reduced pressure, ordinary pressure or pressurization, but normally the reaction is preferably conducted in a range of 0.01 kPa to 10 MPa (absolute pressure). In consideration of facilitating industrial implementation the pressure is preferably reduced pressure or ordinary pressure, preferably in the range of 0.1 kPa to 1.5 MPa (absolute pressure).

The reaction of step (1) is preferably conducted in a liquid phase. However, the melting point of thiourea being 185° C., a liquid phase will sometimes fail to form with the organic primary amine and thiourea alone under the set reaction conditions. In such cases it is preferred to use a solvent.

Examples of solvents that are preferred for use include alkanes such as pentane (and its various isomers), hexane (and its various isomers), heptane (and its various isomers), octane (and its various isomers), nonane (and its various isomers) and decane (and its various isomers); aromatic hydrocarbons and alkyl-substituted aromatic hydrocarbons such as benzene, toluene, xylene (and its various isomers), ethylbenzene, diisopropylbenzene (and its various isomers), dibutylbenzene (and its various isomers) and naphthalene; nitrile compounds such as acetonitrile and benzonitrile; halogen- or nitro-substituted aromatic compounds such as chlorobenzene, dichlorobenzene (and its various isomers), bromobenzene, dibromobenzene (and its various isomers), chloronaphthalene, bromonaphthalene, nitrobenzene and nitronaphthalene; polycyclic hydrocarbon compounds such as diphenyl, substituted-diphenyl, diphenylmethane, terphenyl, anthracene and dibenzyltoluene (and its various isomers); aliphatic hydrocarbons such as cyclohexane, cyclopentane, cyclooctane and ethylcyclohexane; ketones such as methyl ethyl ketone and acetophenone; esters such as dibutyl phthalate, dihexyl phthalate, dioctyl phthalate and benzylbutyl phthalate; ethers and thioethers such as tetrahydrofuran, 1,4-dioxane, 1,2-dimethoxyethane, diphenyl ether and diphenyl sulfide; ketone compounds such as acetone and methyl ethyl ketone; ester compounds such as ethyl acetate and ethyl benzoate; and sulfoxides such as dimethyl sulfoxide and diphenyl sulfoxide. The aforementioned hydroxy compounds (alcohols and aromatic hydroxy compounds) may also be satisfactorily used as reaction solvents.

The reactor used to carry out the reaction is not particularly restricted and any known reactor may be employed, although a tank and/or tower reactor is preferred.

Specifically, conventionally known reactors such as a stirring tank, pressurized stirring tank, reduced-pressure stirring tank, tower reactor, distillation column, packed tower, thin-film distiller or the like may be used in appropriate combinations.

There are no particular restrictions on the material of the reactor, and publicly known materials may be used. For example, glass, stainless steel, carbon steel, hastelloy, or glass lined or TEFLON® coated base materials may be used. SUS304, SUS316 and SUS316L are inexpensive and preferred for use. If necessary, there may be added measuring devices such as a flowmeter and thermometer and known processing equipment such as a reboiler, pump and condenser, while heating may be by a known method using steam, a heater or the like, and cooling may be by a known method using natural cooling, cooling water, brine or the like. Steps may also be added to the process as necessary. For example, steps and devices that are readily apparent to a person or engineer skilled in the art may be added, such as a step of removing the ammonia that is produced (described below), a step of purifying the organic primary amine, a step of dissolving the thiourea in a solvent, a step of separating the solvent or a step of incinerating and disposing of the by-products or other components.

Step (2) is a step of thermally decomposing the compound with a thioureido group produced in step (1), and separating the isothiocyanate and ammonia that are produced, and it is a step in which the reaction represented by the following formula (11) is conducted.

[Chemical Formula 10]

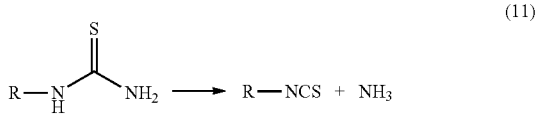

(11)

In the formula, R represents an organic group.

The description is of the reaction of formula (11) above in which a compound with a thioureido group derived from a monofunctional organic primary amine is used, but it will be readily appreciated by a person skilled in the art that the same reaction proceeds even when using a polyfunctional compound with a thioureido group.

The reaction temperature will depend on the thermal decomposition reactivity of the thioureido compound used, but it is preferably in the range of 150° C. to 350° C. At a temperature of lower than 150° C., the reaction may be slow or the reaction may essentially not take place. At a temperature higher than 350° C., on the other hand, alteration reaction of the thioureido compound may take place. From this viewpoint, a more preferred temperature range is 170° C. to 320° C., and an even more preferred range is 190° C. to 300° C.

The reaction pressure will differ depending on the composition of the reaction system, the reaction temperature, the method of removing ammonia, the reactor used and the like, and it may be reduced pressure, ordinary pressure or pressurization, but normally the reaction is preferably conducted in a range of 0.01 kPa to 10 MPa (absolute pressure). Furthermore, because of the rapid reaction rate between the ammonia and isothiocyanate produced in this reaction, it is preferable to promptly remove the produced ammonia out of the system, and considering that removal of the ammonia is to be accomplished by distillation, it is preferably at reduced pressure or ordinary pressure, and more preferably at reduced pressure. Specifically, it may be in the range of 0.1 kPa to 80 kPa (absolute pressure) and more preferably 1 kPa to 50 kPa.

The reactor used to carry out the reaction is not particularly restricted and a known reactor may be employed, although a tank and/or tower reactor is preferred.

Specifically, conventionally known reactors such as a stirring tank, pressurized stirring tank, reduced-pressure stirring tank, tower reactor, distillation column, packed tower, thin-film distiller or the like may be used in appropriate combinations.

There are no particular restrictions on the material of the reactor, and publicly known materials may be used. For example, glass, stainless steel, carbon steel, hastelloy, or glass lined or TEFLON® coated base materials may be used. SUS304, SUS316 and SUS316L are inexpensive and preferred for use. If necessary, there may be added measuring devices such as a flowmeter and thermometer and known processing equipment such as a reboiler, pump and condenser, while heating may be by a known method using steam, a heater or the like, and cooling may be by a known method using natural cooling, cooling water, brine or the like. Steps may also be added to the process as necessary.

<Second Method>

The second method is a method including the following step (I). Step (I): A step of reacting an organic primary amine and thiourea and separating the isothiocyanate and ammonia that are produced.

The reaction of step (I) is represented by the following formula (12).

[Chemical Formula 11]

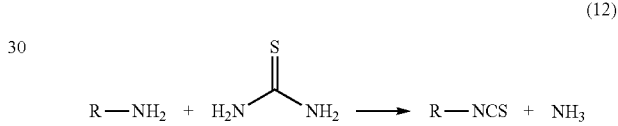

(12)

In the formula, R represents an organic group.

The description is of the reaction of formula (12) wherein a monofunctional organic primary amine has been used, but it will be readily appreciated by a person skilled in the art that the same reaction proceeds even when using a polyfunctional organic primary amine.

The reaction represented by formula (12) is a method combining the reactions represented by formula (10) and formula (11) above, or a separate reaction conducted simultaneously, and it may be carried out by conducting the reaction between the organic primary amine and the thiourea at a temperature that causes the decomposition reaction of the compound with a thioureido group represented by formula (11) to take place, and removing out of the reaction system the ammonia that is produced with the isothiocyanate.

The amount of thiourea may be in the range of 1- to 100-fold as the stoichiometric ratio with respect to the amino groups of the organic primary amine. When a low amount of thiourea is used there will be a tendency toward production of complex-substituted thiocarbonyl compounds and the like, and it is therefore preferred to use an excess of thiourea, but using a large excess of thiourea can conversely also tend toward production of complex-substituted thiocarbonyl compounds, or result in persistence of unreacted thiourea, necessitating a great deal of effort for separation and recovery of the thiourea (described below). Thus, the amount of thiourea is in the range of preferably 1.1- to 10-fold and more preferably 1.5- to 5-fold as the stoichiometric ratio with respect to the amino groups of the organic primary amine.

The reaction temperature will depend on the reactivity of the compounds used, but it is preferably in the range of 150°

C. to 350° C. At a temperature of lower than 150° C., the reaction may be slow or the reaction may essentially not take place. At a temperature higher than 350° C., on the other hand, alteration reaction may take place. From this viewpoint, a more preferred temperature range is 170° C. to 320° C., and an even more preferred range is 190° C. to 300° C.

The reaction pressure will differ depending on the composition of the reaction system, the reaction temperature, the method of removing ammonia, the reactor used and the like, and it may be reduced pressure, ordinary pressure or pressurization, but normally the reaction is preferably conducted in a range of 0.01 kPa to 10 MPa (absolute pressure). In addition, since the reaction is accomplished by removing the produced ammonia out of the system, and considering that the removal of ammonia will be accomplished by distillation, it is preferably conducted under reduced pressure or at ordinary pressure, and more preferably under reduced pressure. Specifically, it may be in the range of 0.1 kPa to 80 kPa (absolute pressure) and more preferably 1 kPa to 50 kPa.

While the reaction of step (I) is preferably carried out in a liquid phase, the melting point of thiourea is 185° C. and a liquid phase will sometimes fail to form with the organic primary amine and thiourea alone under the set reaction conditions. In such cases it is preferred to use a solvent.

Examples of solvents that are preferred for use include alkanes such as pentane (and its various isomers), hexane (and its various isomers), heptane (and its various isomers), octane (and its various isomers), nonane (and its various isomers) and decane (and its various isomers); aromatic hydrocarbons and alkyl-substituted aromatic hydrocarbons such as benzene, toluene, xylene (and its various isomers), ethylbenzene, diisopropylbenzene (and its various isomers), dibutylbenzene (and its various isomers) and naphthalene; nitrile compounds such as acetonitrile and benzonitrile; halogen- or nitro-substituted aromatic compounds such as chlorobenzene, dichlorobenzene (and its various isomers), bromobenzene, dibromobenzene (and its various isomers), chloronaphthalene, bromonaphthalene, nitrobenzene and nitronaphthalene; polycyclic hydrocarbon compounds such as diphenyl, substituted-diphenyl, diphenylmethane, terphenyl, anthracene and dibenzyltoluene (and its various isomers); aliphatic hydrocarbons such as cyclohexane, cyclopentane, cyclooctane and ethylcyclohexane; ketones such as methyl ethyl ketone and acetophenone; esters such as dibutyl phthalate, dihexyl phthalate, dioctyl phthalate and benzylbutyl phthalate; ethers and thioethers such as tetrahydrofuran, 1,4-dioxane, 1,2-dimethoxyethane, diphenyl ether and diphenyl sulfide; ketone compounds such as acetone and methyl ethyl ketone; ester compounds such as ethyl acetate and ethyl benzoate; and sulfoxides such as dimethyl sulfoxide and diphenyl sulfoxide. The aforementioned hydroxy compounds (alcohols and aromatic hydroxy compounds) may also be satisfactorily used as reaction solvents.

The reactor used to carry out the reaction is not particularly restricted and a known reactor may be employed, although a tank and/or tower reactor is preferred.

Specifically, conventionally known reactors such as a stirring tank, pressurized stirring tank, reduced-pressure stirring tank, tower reactor, distillation column, packed tower, thin-film distiller or the like may be used in appropriate combinations.

There are no particular restrictions on the material of the reactor, and publicly known materials may be used. For example, glass, stainless steel, carbon steel, hastelloy, or glass lined or TEFLON® coated base materials may be used. SUS304, SUS316 and SUS316L are inexpensive and preferred for use. If necessary, there may be added measuring devices such as a flowmeter and thermometer and known processing equipment such as a reboiler, pump and condenser, while heating may be by a known method using steam, a heater or the like, and cooling may be by a known method using natural cooling, cooling water, brine or the like. Steps may also be added to the process as necessary. For example, steps and devices that are readily apparent to a person or engineer skilled in the art may be added, such as a step of removing the ammonia that is produced (described below), a step of purifying the organic primary amine, a step of dissolving the thiourea in a solvent, a step of separating the solvent or a step of incinerating and disposing of the by-products or other components.

<Third Method>

The third method is a method including the following step (A) to step (C).

Step (A): A step of reacting an organic primary amine and thiourea to produce a compound with a thioureido group and ammonia.

Step (B): A step of reacting the compound with a thioureido group and a hydroxy compound to produce an N-substituted O-substituted thiocarbamate and ammonia, and separating out the ammonia.

Step (C): A step of thermally decomposing the N-substituted O-substituted thiocarbamate to produce an isothiocyanate.

Step (A) is a step of reacting an organic primary amine and thiourea to produce a compound with a thioureido group and ammonia, and it is the same reaction as step (1) described above.

Step (B) is a step of reacting the compound with a thioureido group of step (A) with a hydroxy compound to produce an N-substituted O-substituted thiocarbamate and ammonia, and separating out the ammonia, and it is a step of conducting the reaction represented by the following formula (13).

[Chemical Formula 12]

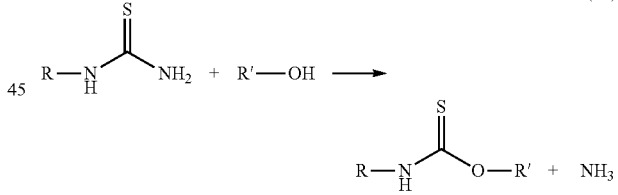

In the formula, R and R' each independently represent an organic group.

The description is of the reaction of formula (13) wherein a compound with a thioureido group derived from a monofunctional organic primary amine, and a monofunctional hydroxy compound have been used, but it will be readily appreciated by a person skilled in the art that the same reaction proceeds even when using a polyfunctional compound with a thioureido group, and/or a polyfunctional hydroxy compound.

The amount of hydroxy compound may be in the range of 1- to 100-fold as the stoichiometric ratio with respect to the thioureido groups of the compound with a thioureido group. When the amount of hydroxy compound used is low the desired reaction will proceed with more difficulty and secondary reactions will have a greater tendency to take place, and therefore an excess of hydroxy compound is preferably used, but using a large excess of hydroxy compound may result in a larger reactor and increase the heat required, and may tend to lower the production efficiency. Consequently, the amount of hydroxy compound is preferably in the range of 2- to 80-fold and more preferably 3- to 50-fold as the stoichiometric ratio with respect to the thioureido groups of the compound with a thioureido group.

The hydroxy compound used may be the actual hydroxy compound used as the solvent in step (A), or when a different solvent has been used in step (A), fresh hydroxy compound may be added either after removal of the solvent or without removing the solvent.

The reaction temperature will depend on the compounds used, but it is preferably in the range of 100° C. to 300° C. At a temperature of lower than 100° C., the reaction may be slow or the reaction may essentially not take place. At a temperature higher than 300° C., on the other hand, alteration reaction of the compound with a thioureido group will have a greater tendency to take place. From this viewpoint, a more preferred temperature range is 120° C. to 280° C., and an even more preferred range is 140° C. to 250° C.

In the reaction conducted in this step (reaction (13) described above), ammonia by-product results together with the desired N-substituted O-substituted carbamate, but this ammonia is highly reactive with the N-substituted O-substituted carbamate. Consequently, in order to increase the N-substituted O-substituted carbamate yield, it is necessary to conduct the reaction while removing as much of the ammonia by-product as possible out of the system. Preferably, the ammonia is removed so that the ammonia concentration in the reaction mixture is no greater than 1000 ppm, more preferably no greater than 300 ppm, even more preferably no greater than 100 ppm and most preferably no greater than 10 ppm. The method may be carried out by reactive distillation, a method using an inert gas, a method using membrane separation or adsorptive separation, or the like. Reactive distillation, for example, is a method in which the ammonia that is successively produced during the reaction is separated out in gaseous form by distillation. In order to increase the ammonia distillation efficiency, it may be accomplished while boiling off the solvent or hydroxy compound. A method using an inert gas is a method in which the ammonia that is successively produced during the reaction is separated from the reaction system in gaseous form by entraining it with an inert gas. The inert gas used may be, for example, nitrogen, helium, argon, carbon dioxide, methane, ethane, propane or the like, either alone or in mixtures, and the preferred method is introduction of the inert gas into the reaction system. In an adsorptive separation method, the adsorbent used may be, for example, an adsorbent that can be used under the temperature conditions in which the reaction is conducted, such as silica, alumina, various zeolites, diatomaceous earths and the like. These different methods of removing ammonia out of the system may be carried out alone, or several different methods may be carried out in combination.

The reaction pressure will differ depending on the composition of the reaction system, the reaction temperature, the method of removing ammonia, the reactor used and the like, and it may be reduced pressure, ordinary pressure or pressurization, but normally the reaction is preferably conducted in a range of 0.01 kPa to 10 MPa (absolute pressure). In consideration of facilitating industrial implementation the pressure is preferably reduced pressure or ordinary pressure, preferably in the range of 0.1 kPa to 1.5 MPa (absolute pressure).

A solvent may also be used for the reaction. Examples of solvents that are preferred for use include alkanes such as pentane (and its various isomers), hexane (and its various isomers), heptane (and its various isomers), octane (and its various isomers), nonane (and its various isomers) and decane (and its various isomers); aromatic hydrocarbons and alkyl-substituted aromatic hydrocarbons such as benzene, toluene, xylene (and its various isomers), ethylbenzene, diisopropylbenzene (and its various isomers), dibutylbenzene (and its various isomers) and naphthalene; nitrile compounds such as acetonitrile and benzonitrile; halogen- or nitro-substituted aromatic compounds such as chlorobenzene, dichlorobenzene (and its various isomers), bromobenzene, dibromobenzene (and its various isomers), chloronaphthalene, bromonaphthalene, nitrobenzene and nitronaphthalene; polycyclic hydrocarbon compounds such as diphenyl, substituted-diphenyl, diphenylmethane, terphenyl, anthracene and dibenzyltoluene (and its various isomers); aliphatic hydrocarbons such as cyclohexane, cyclopentane, cyclooctane and ethylcyclohexane; ketones such as methyl ethyl ketone and acetophenone; esters such as dibutyl phthalate, dihexyl phthalate, dioctyl phthalate and benzylbutyl phthalate; ethers and thioethers such as tetrahydrofuran, 1,4-dioxane, 1,2-dimethoxyethane, diphenyl ether and diphenyl sulfide; ketone compounds such as acetone and methyl ethyl ketone; ester compounds such as ethyl acetate and ethyl benzoate; and sulfoxides such as dimethyl sulfoxide and diphenyl sulfoxide. Also, a hydroxy compound used in excess is preferably used as the reaction solvent.

The reactor used to carry out the reaction is not particularly restricted and a known reactor may be employed, although a tank and/or tower reactor is preferred.

Specifically, conventionally known reactors such as a stirring tank, pressurized stirring tank, reduced-pressure stirring tank, tower reactor, distillation column, packed tower, thin-film distiller or the like may be used in appropriate combinations.

There are no particular restrictions on the material of the reactor, and publicly known materials may be used. For example, glass, stainless steel, carbon steel, hastelloy, or glass lined or TEFLON® coated base materials may be used. SUS304, SUS316 and SUS316L are inexpensive and preferred for use. If necessary, there may be added measuring devices such as a flowmeter and thermometer and known processing equipment such as a reboiler, pump and condenser, while heating may be by a known method using steam, a heater or the like, and cooling may be by a known method using natural cooling, cooling water, brine or the like. Steps may also be added to the process as necessary.

Step (C) is a step of thermally decomposing the N-substituted O-substituted thiocarbamate of step (B) to produce an isothiocyanate, and it is a step in which the reaction represented by the following formula (14) is conducted.

[Chemical Formula 13]

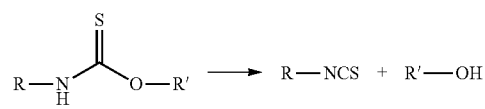

(14)

In the formula, R and R' each independently represent an organic group.

The description is of the reaction of formula (14) with an N-substituted O-substituted thiocarbamate derived from a monofunctional organic primary amine, but it will be readily appreciated by a person skilled in the art that the same reaction proceeds even when using a polyfunctional N-substituted O-substituted thiocarbamate.

The reaction temperature will depend on the thermal decomposition reactivity of the N-substituted O-substituted thiocarbamate used, but preferably it is in the range of 150° C. to 350° C. At a temperature of lower than 150° C., the reaction may be slow or the reaction may essentially not take place. At a temperature higher than 350° C., on the other hand, alteration reaction of the N-substituted O-substituted thiocarbamate may take place. From this viewpoint, a more preferred temperature range is 170° C. to 320° C., and an even more preferred range is 190° C. to 300° C.

The reaction pressure will differ depending on the composition of the reaction system, the reaction temperature, the reactor used and the like, and it may be reduced pressure, ordinary pressure or pressurization, but normally the reaction is preferably conducted in a range of 0.01 kPa to 10 MPa (absolute pressure). Furthermore, because of the rapid reaction rate between the hydroxy compound and isothiocyanate produced in this reaction, it is preferable to promptly remove the produced hydroxy compound out of the system, and considering that removal of the hydroxy compound is to be accomplished by distillation, it is preferably at reduced pressure or ordinary pressure, and more preferably at reduced pressure. Specifically, it may be in the range of 0.1 kPa to 80 kPa (absolute pressure) and more preferably 1 kPa to 50 kPa.

The reactor used to carry out the reaction is not particularly restricted and a known reactor may be employed, although a tank and/or tower reactor is preferred.

Specifically, conventionally known reactors such as a stirring tank, pressurized stirring tank, reduced-pressure stirring tank, tower reactor, distillation column, packed tower, thin-film distiller or the like may be used in appropriate combinations.

There are no particular restrictions on the material of the reactor, and publicly known materials may be used. For example, glass, stainless steel, carbon steel, hastelloy, or glass lined or TEFLON® coated base materials may be used. SUS304, SUS316 and SUS316L are inexpensive and preferred for use. If necessary, there may be added measuring devices such as a flowmeter and thermometer and known processing equipment such as a reboiler, pump and condenser, while heating may be by a known method using steam, a heater or the like, and cooling may be by a known method using natural cooling, cooling water, brine or the like. Steps may also be added to the process as necessary.

<Fourth Method>

The fourth method is a method including the following step (a) and step (b).

Step (a): A step of reacting an organic primary amine, thiourea and a hydroxy compound to produce an N-substituted O-substituted thiocarbamate and ammonia, and separating out the ammonia.

Step (b): A step of thermally decomposing the N-substituted O-substituted thiocarbamate to produce an isothiocyanate.

Step (a) is a step of reacting an organic primary amine, thiourea and a hydroxy compound to produce an N-substituted O-substituted thiocarbamate and ammonia, and separating out the ammonia, and it is a step of conducting the reaction represented by the following formula (15).

[Chemical Formula 14]

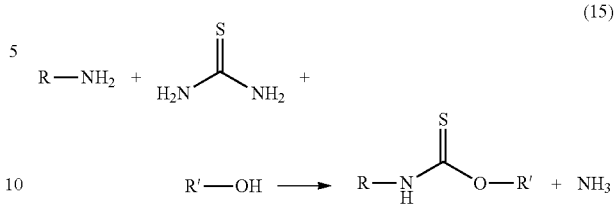

In the formula, R and R' each independently represent an organic group.

The description is of the reaction of formula (15) wherein a monofunctional organic primary amine and a monofunctional hydroxy compound have been used, but it will be readily appreciated by a person skilled in the art that the same reaction proceeds even when using a polyfunctional organic primary amine and/or a polyfunctional hydroxy compound.

The amount of thiourea may be in the range of 1- to 100-fold as the stoichiometric ratio with respect to the amino groups of the organic primary amine. When a low amount of thiourea is used there will be a tendency toward production of complex-substituted thiocarbonyl compounds and the like, and it is therefore preferred to use an excess of thiourea, but using a large excess of thiourea can conversely also tend toward production of complex-substituted thiocarbonyl compounds, or result in persistence of unreacted thiourea, necessitating a great deal of effort for separation and recovery of the thiourea (described below). Thus, the amount of thiourea is in the range of preferably 1.1- to 10-fold and more preferably 1.5- to 5-fold as the stoichiometric ratio with respect to the amino groups of the organic primary amine.

The amount of hydroxy compound may be in the range of 1- to 100-fold as the stoichiometric ratio with respect to the amino groups of the organic primary amine. When the amount of hydroxy compound used is low the desired reaction will proceed with more difficulty and secondary reactions will have a greater tendency to take place, and therefore an excess of hydroxy compound is preferably used, but using a large excess of hydroxy compound may result in a larger reactor and may increase the heat required, tending to lower the production efficiency. Thus, the amount of hydroxy compound is in the range of preferably 2- to 80-fold and more preferably 3- to 50-fold as the stoichiometric ratio with respect to the amino groups of the organic primary amine.

The reaction temperature will depend on the compounds used, but it is preferably in the range of 100° C. to 300° C. At a temperature of lower than 100° C., the reaction may be slow or the reaction may essentially not take place. At a temperature higher than 300° C., on the other hand, alteration reaction of the compound with a thioureido group will have a greater tendency to take place. From this viewpoint, a more preferred temperature range is 120° C. to 280° C., and an even more preferred range is 140° C. to 250° C.

In the reaction conducted in this step, ammonia by-product results together with the desired N-substituted O-substituted carbamate, but this ammonia is highly reactive with the N-substituted O-substituted carbamate. Consequently, in order to increase the N-substituted O-substituted carbamate yield, it is necessary to conduct the reaction while removing as much of the ammonia by-product out of the system as possible. Preferably, the ammonia is removed to an extent such that the ammonia concentration in the reaction mixture is no greater than 1000 ppm, more preferably no greater than 300 ppm, even more preferably no greater than 100 ppm and most preferably no greater than 10 ppm. The method may be carried out by reactive distillation, a method using an inert gas, a method using membrane separation or adsorptive separation, or the like. For example, reactive distillation is a method in which the ammonia that is successively produced during the reaction is separated out in gaseous form by distillation. In order to increase the ammonia distillation efficiency, it may be accomplished while boiling off the solvent or hydroxy compound. A method using an inert gas is a method in which the ammonia that is successively produced during the reaction is separated from the reaction system in gaseous form by entraining it with an inert gas. The inert gas used may be, for example, nitrogen, helium, argon, carbon dioxide, methane, ethane, propane or the like, either alone or in mixtures, and the preferred method is introduction of the inert gas into the reaction system. In an adsorptive separation method, the adsorbent used may be, for example, an adsorbent that can be used under the temperature conditions in which the reaction is conducted, such as silica, alumina, various zeolites, diatomaceous earths and the like. These different methods of removing ammonia out of the system may be carried out alone, or several different methods may be carried out in combination.

The reaction pressure will differ depending on the composition of the reaction system, the reaction temperature, the method of removing the ammonia, the reactor used and the like, and it may be reduced pressure, ordinary pressure or pressurization, but normally the reaction is preferably conducted in a range of 0.01 kPa to 10 MPa (absolute pressure). In consideration of facilitating industrial implementation, the pressure is preferably reduced pressure or ordinary pressure, preferably in the range of 0.1 kPa to 1.5 MPa (absolute pressure).

A solvent may also be used for the reaction. Examples of solvents that are preferred for use include alkanes such as pentane (and its various isomers), hexane (and its various isomers), heptane (and its various isomers), octane (and its various isomers), nonane (and its various isomers) and decane (and its various isomers); aromatic hydrocarbons and alkyl-substituted aromatic hydrocarbons such as benzene, toluene, xylene (and its various isomers), ethylbenzene, diisopropylbenzene (and its various isomers), dibutylbenzene (and its various isomers) and naphthalene; nitrile compounds such as acetonitrile and benzonitrile; halogen- or nitro-substituted aromatic compounds such as chlorobenzene, dichlorobenzene (and its various isomers), bromobenzene, dibromobenzene (and its various isomers), chloronaphthalene, bromonaphthalene, nitrobenzene and nitronaphthalene; polycyclic hydrocarbon compounds such as diphenyl, substituted-diphenyl, diphenylmethane, terphenyl, anthracene and dibenzyltoluene (and its various isomers); aliphatic hydrocarbons such as cyclohexane, cyclopentane, cyclooctane and ethylcyclohexane; ketones such as methyl ethyl ketone and acetophenone; esters such as dibutyl phthalate, dihexyl phthalate, dioctyl phthalate and benzylbutyl phthalate; ethers and thioethers such as tetrahydrofuran, 1,4-dioxane, 1,2-dimethoxyethane, diphenyl ether and diphenyl sulfide; ketone compounds such as acetone and methyl ethyl ketone; ester compounds such as ethyl acetate and ethyl benzoate; and sulfoxides such as dimethyl sulfoxide and diphenyl sulfoxide. Also, a hydroxy compound used in excess is preferably used as the reaction solvent.

The reactor used to carry out the reaction is not particularly restricted and a known reactor may be employed, although a tank and/or tower reactor is preferred.

Specifically, conventionally known reactors such as a stirring tank, pressurized stirring tank, reduced-pressure stirring tank, tower reactor, distillation column, packed tower, thin-film distiller or the like may be used in appropriate combinations.

There are no particular restrictions on the material of the reactor, and publicly known materials may be used. For example, glass, stainless steel, carbon steel, hastelloy, or glass lined or TEFLON® coated base materials may be used. SUS304, SUS316 and SUS316L are inexpensive and preferred for use. If necessary, there may be added measuring devices such as a flowmeter and thermometer and known processing equipment such as a reboiler, pump and condenser, while heating may be by a known method using steam, a heater or the like, and cooling may be by a known method using natural cooling, cooling water, brine or the like. Steps may also be added to the process as necessary.

Step (b) is the same method as in step (C) described above.

<Recovery of Ammonia During N-Substituted O-Substituted Carbamate Production>

Ammonia by-product is separated out in step (B) of the second method and step (a) of the third method, and the method therefor will now be described.

In step (B) and step (a), all or a portion of the hydroxy compound and all or a portion of the compound with a thiocarbonyl group, except for the N-substituted O-substituted thiocarbamate, are separated as a gas phase component together with ammonia, and the gas phase component is used for the following step (Y).

Step (Y): A step of introducing the gas phase component including ammonia, a hydroxy compound and a compound with a thiocarbonyl group into a condenser and condensing the hydroxy compound and the compound with a thiocarbonyl group.

In this step, the gas phase component comprising the hydroxy compound, the compound with a thiocarbonyl group except for the N-substituted O-substituted thiocarbamate (referred to simply as "compound with a thiocarbonyl group" for this embodiment) and the ammonia by-product of the reaction, is introduced into a condenser and all or a portion of the hydroxy compound and all or a portion of the compound with a thiocarbonyl group are condensed.

In this embodiment, the "compound with a thiocarbonyl group" to be condensed in the condenser is a group having a thiocarbonyl group, that is used or produced in the reactions of step (B) and step (a), being a compound other than the N-substituted O-substituted thiocarbamate which is the target compound, and it includes the actual thiourea used as the starting material (the unreacted substance and/or the excess portion when it is used in excess with respect to the organic primary amine), compounds resulting from reaction between thiourea and the hydroxy compound, and compounds resulting from reaction of the same or different thiourea compounds. While it is difficult to identify all compounds with a thiocarbonyl group, specific compounds include the thiourea and thiocarbamic acid ester used as starting materials, and isothiocyanic acid, dithiobiuret, trithiocyanuric acid and the like. The compound with a thiocarbonyl group can be quantified by a method of detecting the thiocarbonyl groups in the compound, by a method such as infrared spectroscopy, near-infrared spectroscopy, Raman spectroscopy, ultraviolet spectroscopy or the like, or it can be quantified by a method of specifically analyzing the produced compound by a method such as gas chromatography, liquid chromatography or NMR. Most of these compounds with a thiocarbonyl group have high melting points, and tend to easily precipitate.

In step (Y), the ratio (HIT) of the amount (H) of the hydroxy compound to be condensed with respect to the amount (T) of the compound with a thiocarbonyl group to be condensed is preferably 1 or greater. The amount (T) of the compound with a thiocarbonyl group to be condensed represents the total number of thiocarbonyl groups in the compound with a thiocarbonyl group to be condensed, and the amount (H) of the hydroxy compound to be condensed represents the number of hydroxy compounds to be condensed (H). That is, the ratio (H/T) may be restated as the stoichiometric ratio of thiocarbonyl groups and hydroxy compound.

As the method for quantifying the compound with a thiocarbonyl group to be condensed and the hydroxy compound to be condensed, the gas component before condensation or the condensed liquid may be analyzed by any of various known methods, and the measured value of the gas component and/or the measured value of the condensed liquid may be used. Examples of methods to be used include gas chromatography, liquid chromatography, NMR, (near) infrared spectroscopy and ultraviolet spectroscopy. The condensed liquid will sometimes contain components resulting from reaction between the isothiocyanate groups and hydroxy compound during the condensation process, such as N-substituted O-substituted thiocarbamate. In such cases, each carbamate group of an N-substituted O-substituted thiocarbamate is added to the aforementioned amount as having been formed from a thiocarbonyl group and hydroxy compound.

In the condensation procedure, the amount of hydroxy compound to be condensed is 1 or greater with respect to the amount of the compound with a thiocarbonyl group to be condensed, in order to allow their mixture to be a uniform liquid mixture in the condenser. This will not only facilitate handling of the mixture obtained by condensation, but will also help avoid causing problems such as adhesion and accumulation of solid components in the condenser. Furthermore, as explained below, this is also effective for ensuring that the compound with a thiocarbonyl group contained in the ammonia recovered from the condenser is no greater than a certain amount. The amount of hydroxy compound to be condensed with respect to the compound with a thiocarbonyl group to be condensed is more preferably such that HIT is 2 or greater and more preferably 3 or greater. In order to ensure that the amount of the hydroxy compound to be condensed with respect to the compound with a thiocarbonyl group to be condensed is within this range, the extent of evaporation of the hydroxy compound may be adjusted by controlling the temperature or pressure, and the amount of condensation of the hydroxy compound may be adjusted by controlling the temperature of the condenser. In addition, in order to handle the condensate as a liquid phase component, a temperature is preferably maintained so that the hydroxy compound does not solidify.

Furthermore, the ratio of the amount of hydroxyl compound to be condensed with respect to the amount of compound with a thiocarbonyl group (HIT) may be, for example, 100 or smaller or even 50 or smaller, although this is not restrictive. In such cases the effect of the invention will still be adequately exhibited.

The condenser recovers the gaseous mixture including ammonia, as the component that is not to be condensed, and the compound with a thiocarbonyl group contained in the gaseous mixture is limited to no greater than a specified amount. Specifically, the number of thiocarbonyl groups (—C(=S)—) in the compound with a thiocarbonyl group, contained in the ammonia, is no greater than 1, preferably no greater than 0.5, more preferably no greater than 0.1 and even more preferably no greater than 0.02, with respect to the number of ammonia molecules. The reason for the specified range for the amount of compound with a thiocarbonyl group contained in the ammonia is in order to avoid adhesion and accumulation of solid components in the line used for transport of the ammonia by the condenser.

While it is not possible to identify all of the solid components that adhere or accumulate in the line used for transport of ammonia, investigation by the present inventors has shown that most of it consists of compounds with a thiocarbonyl group. The method for avoiding adhesion and accumulation of such solid components may be a method of heating the line used for transport of the ammonia and decomposing the compound with a thiocarbonyl group, but investigation by the present inventors has shown that simple heating alone usually results in polymerization of decomposition products (for example, isocyanic acid) or reaction of the decomposition products with other compounds with a thiocarbonyl group, making it difficult to completely avoid adhesion and accumulation of solid components. Furthermore, it was found that when the line is simply heated, the compound with a thiocarbonyl group contained in the ammonia, and other decomposition products, are rapidly cooled and solidify especially at the exit port of the line used for transport of the ammonia (the sections contacting with air and the like), often resulting in considerable adhesion and accumulation of the solid components. As a result of much diligent research on this issue, the present inventors have found, surprisingly, that the problem of adhesion and accumulation of solid components can be solved if the compound with a thiocarbonyl group contained in the ammonia is limited to no greater than the amount specified above, and the present invention has thereupon been completed. While the mechanism by which this effect is exhibited is not completely understood, the present inventors conjecture that adhesion and accumulation in the line occurs due to the compound with a thiocarbonyl group itself and due to decomposition and/or polymerization products from the compound with a thiocarbonyl group, and that limiting the thiocarbonyl groups in the compound with a thiocarbonyl group to no greater than a specified concentration significantly reduces adhesion of the compound with a thiocarbonyl group itself as well as the reaction rates of decomposition and/or polymerization of the compound.

The term "compound with a thiocarbonyl group" is a group having a thiocarbonyl group that is used in the reaction between the organic primary amine, thiourea and hydroxy compound, and it includes the actual thiourea used as the starting material (the unreacted substance and/or the excess portion when it is used in excess with respect to the organic primary amine), compounds resulting from reaction between thiourea and the hydroxy compound, and compounds resulting from reaction of the same or different thiourea compounds. While it is difficult to identify all compounds with a thiocarbonyl group, specific compounds include the thiourea and thiocarbamic acid ester used as starting materials, and by-products such as isothiocyanic acid, dithiobiuret, trithiocyanuric acid and the like. Of these compounds, thiourea, isothiocyanic acid and thiocarbamic acid ester require particular attention since they are often contained in ammonia and in large amounts, although it depends on the production conditions for the N-substituted O-substituted thiocarbamate. According to investigation by the present inventors, controlling the amounts of these compounds in the ammonia to within the preferred ranges specified above largely avoids the problems of adhesion and accumulation of solid components in the line used to transport the ammonia.

The method for quantifying the compound with a thiocarbonyl group in the ammonia may be any of various known methods, and methods such as gas chromatography, liquid chromatography, NMR (near) infrared spectroscopy, ultraviolet spectroscopy and the like may be used. Specifically, for example, the ammonia may be directly introduced as gas for gas chromatography measurement (the line used to transport the ammonia may be directly connected to the gas chromatography means for measurement, or for example, ammonia gas collected in a bag or container for gas collection, such as a Tedlar bag, may be injected into the gas chromatography means with a gas-tight syringe, for example, and measured). Also, for example, the compound with a thiocarbonyl group (A) contained in the ammonia may be absorbed into water, an organic solvent or the like and measured by a method such as gas chromatography, liquid chromatography, NMR, (near) infrared spectroscopy, ultraviolet spectroscopy or the like. Of these methods, it is preferred to carry out a method in which the ammonia is introduced directly as gas to gas chromatography means equipped with a mass spectrometer, the compound with a thiocarbonyl group is identified, and the summed product of the amount of the compound with a thiocarbonyl group multiplied by the number of thiocarbonyl groups in the compound with a thiocarbonyl group is taken and recorded as the amount of the compound with a thiocarbonyl group contained in the ammonia.

When the compound with a thiocarbonyl group is present in an amount below the quantifiable limit in the methods mentioned above the concentration in the ammonia is extremely low and therefore will almost never affect adhesion and accumulation of solid components in the ammonia transport line, and in such cases there is no effect if the "amount of the compound with a thiocarbonyl group" is not included, such that it may be ignored.

The mixture of the hydroxy compound and the compound with a thiocarbonyl group, that has been condensed by the condenser, may be circulated inside the reactor for reutilization in the reaction of step (B) or step (a), or the mixture may be recovered for reutilization of the hydroxy compound and/or the compound with a thiocarbonyl group in the reaction of step (A), step (B) or step (a).

For reutilization of the condensed components, preferably the amount of ammonia contained in the hydroxy compound and the compound with a thiocarbonyl group is no greater than 5000 ppm. Reutilization is possible even if ammonia is contained at greater than 5000 ppm, but as mentioned above, the reactions of step (B) and step (a) are equilibrium reactions with by-production of ammonia, and it is necessary to remove the produced ammonia out of the system in order to efficiently promote these reactions. If a very large amount of ammonia is contained in the hydroxy compound and the compound with a thiocarbonyl group that are reutilized, a greater amount of ammonia will be extracted during the reaction, potentially exceeding the amount of ammonia that can be extracted per unit time (which depends on the reactor capabilities, the reaction conditions, and the like), often resulting in introduction of ammonia and making it impossible to lower the ammonia concentration in the reaction mixture to the preferred range (the range specified above), thereby lowering the N-substituted O-substituted thiocarbamate yield. Consequently, the amount of ammonia contained in the hydroxy compound and the compound with a thiocarbonyl group that are reutilized in the reaction is preferably a low amount, and yet significant efforts are necessary to reduce the amount of ammonia to a minimum. From this viewpoint, the amount of ammonia contained in the hydroxy compound and the compound with a thiocarbonyl group is more preferably no greater than 3000 ppm and even more preferably no greater than 2000 ppm.

As mentioned above, a variety of compounds are sometimes recovered as compounds with a thiocarbonyl group, and a mixture of the hydroxy compound and the compound with a thiocarbonyl group can still be reutilized as the condensed component without problems even if such compounds are included.

<Separation of Ammonia in Step of Reaction Producing Thioureido Group>

Step (1) and step (A) described above are steps in which an organic primary amine and thiourea are reacted to produce a thioureido group, with ammonia being a by-product of these steps. According to investigation by the present inventors, even without removal of ammonia, reaction (7) mentioned above has its equilibrium shifted heavily toward the product side, and the compound with a thioureido group, as the target compound of this step, can be obtained at a high yield. However, since the subsequent step (step (2) in the case of step (1), or step (B) in the case of step (A)) is a step requiring removal of ammonia, the step of removing ammonia (step (X)) is preferably carried out during this step (step (1) or step (A)), from the viewpoint of reducing the amount of ammonia to be removed in the subsequent step.

Step (X): A step of separating the compound with a thioureido group and ammonia that are produced.

Step (X) may be carried out simultaneously with step (1) or step (A), or after step (1) and step (A), or it may be carried out simultaneously with step (1) or step (A) and after step (1) or step (A).

There are no particular restrictions on the method of removing the ammonia, and it may be a method by reactive distillation and an inert gas, or a method by membrane separation and adsorptive separation, or the like. For example, reactive distillation is a method in which the ammonia that is successively produced during the reaction is separated out in gaseous form by distillation. In order to increase the ammonia distillation efficiency, it may be accomplished while boiling off the solvent or hydroxy compound. A method using an inert gas is a method in which the ammonia that is successively produced during the reaction is separated from the reaction system in gaseous form by entraining it with an inert gas. The inert gas used may be, for example, nitrogen, helium, argon, carbon dioxide, methane, ethane, propane or the like, either alone or in mixtures, and the preferred method is introduction of the inert gas into the reaction system. In an adsorptive separation method, the adsorbent used may be, for example, an adsorbent that can be used under the temperature conditions in which the reaction is conducted, such as silica, alumina, various zeolites, diatomaceous earths and the like. These different methods of removing ammonia out of the system may be carried out alone, or several different methods may be carried out in combination.

[Composition for Transporting and Storing N-Substituted O-Substituted Thiocarbamate]

The composition for transporting and storing according to this embodiment includes an N-substituted O-substituted thiocarbamate and a hydroxy compound, wherein the equivalent weight ratio of hydroxy groups of the hydroxy compound with respect to the carbamate groups of the N-substituted O-substituted thiocarbamate is in the range of 1 to 100.

Generally speaking, an N-substituted O-substituted thiocarbamate readily forms hydrogen bonds between molecules due to the carbamate groups composing the N-substituted O-substituted thiocarbamate. For this reason, the N-substituted O-substituted thiocarbamate will usually have a high melting point. When transporting such an N-substituted O-substituted thiocarbamate, there is employed, for example, a method of shaping wherein the solid N-substituted O-substituted thiocarbamate is pulverized, worked into pellets or the like, or a method of heating to a higher temperature than the melting point of the N-substituted O-substituted thiocarbamate and transporting the N-substituted O-substituted thiocarbamate in liquid form.

When a shaped form is to be transported, the high variation in shapes of the N-substituted O-substituted thiocarbamate can lead to blockage of the transport line. Consequently, complex equipment is necessary to stably transport a constant amount of N-substituted O-substituted thiocarbamate, or often a step is necessary to limit the shapes of the N-substituted O-substituted thiocarbamate within a given range.

On the other hand, when the N-substituted O-substituted thiocarbamate is to be transported in liquid form, it is necessary for heating to be at a higher temperature than the melting point of the N-substituted O-substituted thiocarbamate, in consideration of preventing solidification during transport. When the N-substituted O-substituted thiocarbamate has been kept at such a high temperature, thermal decomposition reaction of the N-substituted O-substituted thiocarbamate often takes place at undesired locations, producing isothiocyanate, or heat alteration reaction of the N-substituted O-substituted thiocarbamate often takes place. In particular, since the N-substituted O-substituted thiocarbamate has a low thermal decomposition temperature compared to the N-substituted O-substituted carbamate, for example, isothiocyanate groups tend to be generated by thermal decomposition of the N-substituted O-substituted thiocarbamate.

The composition of this embodiment solves the aforementioned problem, and when the composition is transported or stored, it has the effect of inhibiting heat alteration reaction of the N-substituted O-substituted thiocarbamate in the composition, allowing the N-substituted O-substituted thiocarbamate to be stably maintained. While the mechanism by which the composition exhibits an effect of inhibiting heat alteration reaction of the N-substituted O-substituted thiocarbamate is not completely understood, the present inventors conjecture that the hydroxy compound in the composition forms hydrogen bonds with the thiourethane bonds (—NHC(=S)—O—) of the N-substituted O-substituted thiocarbamate, thereby creating a state in which the thiourethane bonds do not easily come into proximity with each other, and therefore this may inhibit, for example, the reaction of forming compounds with thioureylene groups represented by the following formula (16).

[Chemical Formula 15]

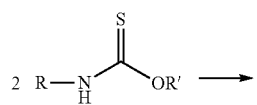

(16)

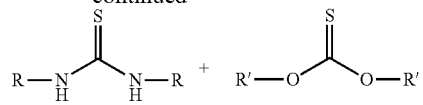

In the formula, R and R' each independently represent an organic group.

The description is of the reaction of formula (16) with a monofunctional N-substituted O-substituted thiocarbamate, but it will be readily appreciated by a person skilled in the art that the same reaction proceeds even with a polyfunctional N-substituted O-substituted thiocarbamate.

The composition ratio between the components of the composition of this embodiment and the other components, is as follows.

(Hydroxy Compound)

The hydroxy compound contains an alcohol or an aromatic hydroxy compound. Preferred for use as alcohols are compounds represented by formula (4) above. Also, preferred for use as aromatic hydroxy compounds are compounds represented by formula (5) above.

(N-Substituted O-Substituted Thiocarbamate)

The N-substituted O-substituted thiocarbamate of the composition of this embodiment is a compound represented by formula (7) or (8) above.

The N-substituted O-substituted thiocarbamate production method of this embodiment is not particularly restricted, and any of various known methods may be used. As one preferred N-substituted O-substituted thiocarbamate production method, there may be mentioned an N-substituted O-substituted thiocarbamate obtained by reacting an organic primary amine, thiourea and a hydroxy compound, and there is preferably used an N-substituted O-substituted thiocarbamate obtained by the different N-substituted O-substituted thiocarbamate production methods described above (step (A) and step (B) of the third method, and step (a) of the fourth method).

Also, in addition to an N-substituted O-substituted thiocarbamate produced by such methods, there may be used an N-substituted O-substituted thiocarbamate produced, for example, by reacting an N-substituted O-substituted thiocarbamate and a hydroxy compound for transesterification reaction in which the ester group of the N-substituted O-substituted thiocarbamate is converted to an ester group derived from the hydroxy compound.

(Thiourea Derivative)

The composition of this embodiment may further include at least one type of compound (hereunder referred to as "thiourea derivative") selected from among thiourea (H$_2$N—C(=S)—NH$_2$), N-unsubstituted O-substituted thiocarbamates, thiocarbonic acid esters, compounds with a thioureido group, dithiobiuret (H$_2$N—C(=S)—NH—C(=S)—NH$_2$) and dithiobiuret derivatives (compounds having a dithiobiuret group (—NHCSNHCSNH$_2$) at an end).

When the N-substituted O-substituted thiocarbamate is obtained by reacting an organic primary amine, thiourea and a hydroxy compound, the dithiobiuret derivative is a compound derived from the organic primary amine, produced by reaction between the organic primary amine, thiourea and hydroxy compound.

As mentioned above, the compound with a thioureido group may also be a compound produced by reaction between an organic primary amine and thiourea during production of an N-substituted O-substituted thiocarbamate from an organic primary amine, thiourea and a hydroxy compound (step (A) of the third method). Specifically, it is a compound represented by formula (4) above.

Generally speaking, when the composition for transporting and storing contains thiourea derivatives, the compounds have active hydrogens and therefore react with the isothiocyanate produced during thermal decomposition of the N-substituted O-substituted thiocarbamate, producing high molecular weight compounds, potentially resulting in the problems of adhesion to the reactor and solidification. Furthermore, these thiourea derivatives themselves undergo thermal decomposition reaction to generate thermal decomposition products such as ammonia and isothiocyanic acid, sometimes producing insoluble high molecular weight compounds by reaction with isothiocyanate.

However, the present inventors have found that a composition containing a specified amount of a thiourea derivative helps to inhibit alteration reaction of the N-substituted O-substituted thiocarbamate during transport and storage. The present inventors have further found that producing an isothiocyanate using this composition has an effect of increasing the isothiocyanate yield. This effect has been hitherto unknown and is a surprising effect. While the mechanism by which the effect is exhibited is not completely understood, the present inventors conjecture that during transport and during storage of the composition, thiourea derivatives might trap trace amounts of contaminating water and oxygen, which inhibits alteration reaction of the N-substituted O-substituted thiocarbamate. The present inventors further conjecture that when the composition is used for production of an isothiocyanate, the thiourea derivatives might function as thermal decomposition catalysts for the N-substituted O-substituted thiocarbamate.

Thus, the preferred mode of the composition for transporting and storing an N-substituted O-substituted thiocarbamate according to this embodiment is an N-substituted O-substituted thiocarbamate where the N-substituted O-substituted thiocarbamate is produced from an organic primary amine, thiourea and a hydroxy compound, the composition optionally further including, in addition to the N-substituted O-substituted thiocarbamate and the hydroxy compound, also at least one compound selected from among thiourea, thiocarbonic acid esters, N-unsubstituted O-substituted thiocarbamates, compounds with a thioureido group, dithiobiuret and dithiobiuret derivatives.

In the composition of this embodiment, the equivalent weight ratio of hydroxy groups of the hydroxy compound with respect to the carbamate groups of the N-substituted O-substituted thiocarbamate is in the range of 1 to 100. Assuming the mechanism described above, a lower concentration of the N-substituted O-substituted thiocarbamate or thiourea derivative in the composition is preferred and therefore the hydroxy groups are preferably in a large excess with respect to the carbamate groups, but on the other hand, using a very large excess of the hydroxy compound may lower the transport efficiency of the N-substituted O-substituted thiocarbamate or overly increase the size of the storage tank during storage. In addition, when the composition is used to produce an isothiocyanate, reverse reaction tends to occur between the hydroxy compound that is present in large excess and the produced isothiocyanate, often lowering the isothiocyanate production yield. In consideration of the above, the ratio of hydroxy groups to carbamate groups is more preferably 1.5 to 50 and even more preferably 3 to 20.

When the N-substituted O-substituted thiocarbamate is an N-substituted O-substituted thiocarbamate obtained by reacting an organic primary amine, thiourea and an aromatic hydroxy compound, the amount of thiourea derivative in the composition of this embodiment, i.e. the total number including the number of molecules V of the thiourea, the number of molecules W of the N-unsubstituted O-substituted thiocarbamate, the number of molecules X of the thiocarbonic acid ester, the number of molecules Y of the dithiobiuret and the number Z of terminal dithiobiuret groups of the dithiobiuret derivative (V+W+X+Y+Z) is preferably 0.0001 to 0.05 with respect to the number of carbamate groups of the N-substituted O-substituted thiocarbamate.

As mentioned above, for stabilization of the N-substituted O-substituted thiocarbamate and increase in the isothiocyanate yield, it is preferred for the composition to contain a certain amount of thiourea derivative. With an excessively large amount of thiourea derivative, however, reaction with the isothiocyanate that is produced during thermal decomposition may result in production of high molecular weight compounds and their adhesion or solidification in the reactor. Thus, the aforementioned total number (V+W+X+Y+Z) is in the range of preferably 0.0001 to 0.03 and more preferably 0.0001 to 0.01 with respect to the N-substituted O-substituted thiocarbamate. The total number (V+W+X+Y+Z) may be determined by a publicly known method. For example, the composition may be analyzed by a method such as gas chromatography or liquid chromatography, and the components contained in the composition may be identified and quantified. The lower limit for the range is 0.0001, but the present inventors have set this based on the detection threshold for determining the total number (V+W+X+Y+Z) using gas chromatography and liquid chromatography.

The composition of this embodiment may also include components other than the aforementioned compounds (N-substituted O-substituted thiocarbamate, hydroxy compound and thiourea derivative). Such components may be any compound with a thioureylene group (—NHCSNH—) in the molecular chain, a Fries rearranged N-substituted O-substituted thiocarbamate (providing that the carbamate group is the group derived from the aromatic hydroxy compound), water, an alcohol, an inert gas (for example, nitrogen gas, carbon dioxide gas, argon gas, ammonia gas or the like), or the like.

For explanation of this embodiment, a thioureylene group (—NHCSNH—) may be referred to as a "thiourein group".

There are no particular restrictions on the content of these components, but if undesirable secondary reactions are expected to occur due to the storage temperature or the like, the amount is preferably controlled periodically. The components to be given particular attention are oxygen, ammonia, water, oxidizing substances and reducing substances. The composition for storage according to this embodiment contains a compound including a nitrogen atom, and it is often the case that aromatic hydroxy compounds are oxidized by oxygen, resulting in phenomena such as alteration, coloration and the like. In addition, since the composition will in most cases be a flammable composition, the oxygen gas may be controlled by a publicly known method, such as for custody and storage of organic chemical substances conducted in the technical field. For example, the gas phase oxygen concentration in the storage tank may be controlled to an oxygen concentration of no greater than 10%, preferably no greater than 1% and even more preferably no greater than 100 ppm, for example, by a method such as nitrogen purging. When the gas phase portion is to be circulated with an inert gas such as nitrogen, the oxygen concentration in the inert gas is controlled to no greater than 10 ppm.

The composition of this embodiment contains ammonia at preferably 1 to 1000 ppm, more preferably 1 to 300 ppm, even more preferably 1 to 100 ppm, yet more preferably 1 to 50 ppm and most preferably 1 to 10 ppm.

The composition of this embodiment preferably contains no metal components deriving from the catalyst or the like. Results of investigation by the present inventors have demonstrated that such metal components have an effect of tending to cause alteration reaction of the N-substituted O-substituted thiocarbamate. Therefore, the metal component content is preferably no greater than 2000 ppm, more preferably no greater than 600 ppm, even more preferably no greater than 200 ppm and most preferably no greater than 20 ppm.

A lower amount of ammonia is preferred in consideration of equilibrium, as is also known in the prior art, but surprisingly, a low amount has an effect of inhibiting alteration reaction of the N-substituted O-substituted thiocarbamate by metal components and the like in the composition.

The amount of ammonia is the amount of ammonia at the start of transport and storage, and as explained above, it is sometimes consumed by the inhibiting effect of the catalyst component during transport and storage. When the composition for transport and storage has been produced, or when it has been prepared, or when it has been placed in the storage tank or when it is initially transported, the composition for transport and storage preferably has the ammonia amount specified above. The method of adjusting the ammonia amount may be by a publicly known method, for example, using an inert gas such as nitrogen for purging into the liquid phase.

Also, as mentioned above, the metal components in the composition may be metal components derived from the catalyst component referred to below. The metal components may include Lewis acids and Lewis acid-producing transition metal compounds, organic tin compounds, copper-based metals, zinc and ferromagnetic metal compounds. Specifically, these include Lewis acids which are typically $AlX_3$, $TiX_3$, $TiX_4$, $VOX_3$, $VX_5$, $ZnX_2$, $FeX_3$ or $SnX_4$ (where X is a halogen or an acetoxy, alkoxy or aryloxy group), or a transition metal compound that produces a Lewis acid; organic tin compounds which are typically $(CH_3)_3SnOCOCH_3$, $(C_2H_5)SnOCOC_6H_5$, $Bu_3SnOCOCH_3$, $Ph_3SnOCOCH_3$, $Bu_2Sn(OCOCH_3)_2$, $Bu_2Sn(OCOC_{11}H_{23})_2$, $Ph_3SnOCH_3$, $(C_2H_5)_3SnOPh$, $Bu_2Sn(OCH_3)_2$, $Bu_2Sn(OC_2H_5)_2$, $Bu_2Sn(OPh)_2$, $Ph_2Sn(CH_3)_2$, $(C_2H_5)_3SnOH$, $PhSnOH$, $Bu_2SnO$, $(CsHi_7)_2SnO$, $Bu_2SnCl_2$ and $BuSnO$ (OH); copper-based metal compounds such as $CuCl$, $CuCl_2$, $CuBr$, $CuBr_2$, $CuI$, $CuI_2$, $Cu(OAc)_2$, $Cu(acac)_2$, copper olefinates, $Bu_2Cu$, $(CH_3O)_2Cu$, $AgNO_3$, $AgBr$, silver picrate and $AgC_6H_6ClO_4$; zinc compounds such as $Zn(acac)_2$; ferromagnetic metal compounds such as $Fe(C_{10}H_8)(CO)_5$, $Fe(CO)_5$, $Fe(C_4H_6)(CO)_3$, $Co(mesitylene)_2(PEt_2Ph_2)$, $COC_5F_5(CO)_7$ and ferrocene. Bu stands for butyl, Ph for phenyl and "acac" for an acetylacetone chelate ligand.

Since a high moisture content may produce a phenomenon in which the composition does not become homogeneous, the water concentration, though depending on the makeup of the composition, is preferably no greater than 10 mass % and preferably no greater than 1 mass % in the composition, and because a large amount of water can cause secondary reactions due to the water when this composition is used as a starting material for the N-substituted O-substituted thiocarbamate, it is therefore controlled to a range of even more preferably no greater than 100 ppm. The method of controlling the water may be a publicly known method, such as using a dehydrating agent or desiccant, or distillation under reduced pressure, under pressurization or at ordinary pressure, purging an inert gas into the liquid phase and entraining and removing out the water, or the like. When an oxidizing substance or reducing substance is present, it can potentially cause modification of the hydroxy compound, and therefore such substances are controlled by a publicly known controlling method for hydroxy compounds. An oxidizing substance is a Bronsted acid or Lewis acid, such as an organic acid or inorganic acid, while a reducing substance is a Bronsted base, Lewis base such as an organic base or inorganic base, or hydrogen gas. Excluded from reducing substances are compounds derived from the composition, such as ammonia, or thiourea or other compounds in the composition.

The conditions for storage and transport of the composition of this embodiment are not particularly restricted, but in some cases will be conditions of high temperature that have a high tendency to result in thermal decomposition reaction of the N-substituted O-substituted thiocarbamate. When the flow property or stability is impaired during storage in the range of −40° C. to 280° C., depending on the storage period, the conditions are preferably 0° C. to 260° C. and even more preferably 40° C. to 260° C., but control may be varied according to the purpose of use of the composition, the storage period and the handleability of the composition. The temperature during transport may be within the same range as the temperature during storage, but when the composition is used as starting material for isothiocyanate production and is to be transported into a thermal decomposition reactor for the N-substituted O-substituted thiocarbamate, it will usually be preheated to the reaction temperature and then transported to the thermal decomposition reactor, and therefore transport may be conducted after confirming that the transport can be safely carried out, depending on the conditions for the thermal decomposition reaction step or the accessory devices of the thermal decomposition reactor. Normally, it will be in the range of −40° C. to 280° C., or if the flow property and stability are not impaired, 0° C. to 260° C. and even more preferably 40° C. to 260° C. As mentioned above, the control may be according to the purpose of use of the composition, the transport time and the composition handleability. There are also no particular restrictions on the pressure during transport, but storage may be under reduced pressure conditions to pressurized conditions. Because the hydroxy compound will sometimes distill off if the storage is under reduced pressure, the proportion of N-substituted O-substituted thiocarbamate and hydroxy compound in the composition is controlled to be in the range specified above. There are no particular restrictions on the storage container, tubings, etc. for storage and transport. Taking into account the combustible organic materials, a container is selected in consideration of the flash point of the composition to be handled, as one that conforms to the regulations of the region in which it is to be handled. There are no particular restrictions on the material, and publicly known materials may be used. For example, glass, stainless steel, carbon steel, hastelloy, or glass lined or TEFLON® coated base materials may be used. The storage tank or transport equipment for the composition may have additional known accessory equipment as necessary, including pumps, heat regulators, instrumentation and the like.

The composition for transporting and storing an N-substituted O-substituted thiocarbamate according to this embodiment may be prepared by mixing an N-substituted O-substituted thiocarbamate, a hydroxy compound and a thiourea derivative so as to have a composition in the range specified above, or it may be prepared by using a composition containing an N-substituted O-substituted thiocarbamate, that has been obtained by production of an N-substituted O-substituted thiocarbamate, and from this, adding and/or removing a hydroxy compound or thiourea derivative so that the resulting composition is as specified above.

The composition for transporting and storing according to this embodiment may be suitably used for production of an isothiocyanate, in particular. Specifically, the composition for transporting and storing may be transported to a thermal decomposition reactor, and supplied for thermal decomposition reaction of the N-substituted O-substituted thiocarbamate in the composition to produce an isothiocyanate.

(Isothiocyanate Production Method)

The isothiocyanate production method of this embodiment comprises a step of thermal decomposition reaction of the N-substituted O-substituted thiocarbamate included in the aforementioned composition for transporting and storing, to obtain an isothiocyanate. The reaction conditions and other aspects of the method of thermal decomposition reaction of the N-substituted O-substituted thiocarbamate are not particularly restricted, and for example, the method described in JP 2089657 B may be used. Furthermore, the same methods as step (C) and step (b) described above may also be suitably used.

<Composition for Transporting and Storing Compound with a Thioureido Group>

The composition for transporting and storing a compound with a thioureido group, according to this embodiment, includes a compound with a thioureido group and a hydroxy compound, and it is a composition for transporting and storing a compound with a thioureido group wherein the equivalent weight ratio of hydroxy groups of the hydroxy compound with respect to the thioureido groups of the compound with a thioureido group is in the range of 1 to 100.

Generally speaking, a compound with a thioureido group tends to forms hydrogen bonds between the molecules by their thioureido groups. Compounds with thioureido groups therefore usually have high melting points. For transport of such a compound with a thioureido group there may be employed, for example, a method in which product that has been shaped by pulverizing the solid compound with a thioureido group or working it into pellets is transported, or a method in which heating is carried out to a higher temperature than the melting point of the compound with a thioureido group and the compound with a thioureido group is transported in liquid form.

When a shaped product is to be transported, the large variation in shapes of the compound with a thioureido group will sometimes lead to blockage of the transport line. Therefore, complex equipment is necessary to stably transport a constant amount of the compound with a thioureido group, or often a step is necessary to limit the shapes of the compound with a thioureido group within a given range.

On the other hand, when the compound with a thioureido group is to be transported in liquid form, it is necessary for heating to be at a higher temperature than the melting point of the compound with a thioureido group, in consideration of preventing solidification during transport. When the compound with a thioureido group has been kept at such a high temperature, thermal decomposition reaction of the compound with a thioureido group often takes place at undesired locations, producing isothiocyanate or ammonia, or undesirable heat alteration reaction of the compound with a thioureido group often takes place, resulting in condensation of the thioureido groups together to form thioureylene groups, or the like.

The composition of this embodiment solves such problems, and, when the composition is to be transported or stored, it exhibits an effect of inhibiting heat alteration reaction of the compound with a thioureido group in the composition to allow the compound with a thioureido group to be stably maintained. While the mechanism by which the composition exhibits an effect of inhibiting heat alteration reaction of the compound with a thioureido group is not completely understood, the present inventors conjecture that the hydroxy compound in the composition forms hydrogen bonds with the thioureido groups of the compound with a thioureido group, thereby creating a state in which the thioureido groups do not easily come into proximity with each other, and therefore this may inhibit, for example, the reaction of forming compounds with thioureido groups represented by the following formula (17).

[Chemical Formula 16]

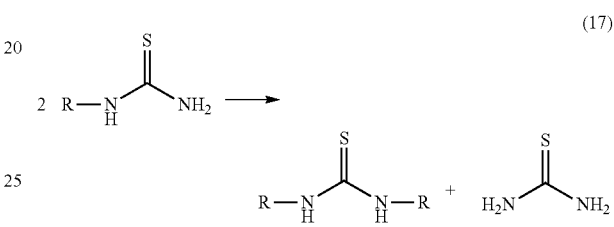

In the formula, R and R' each independently represent an organic group.

The description is of formula (17) as a reaction of a monofunctional compound with a thioureido group, but it will be readily appreciated by a person skilled in the art that the same reaction proceeds even with a polyfunctional compound.

The composition ratio between the components of the composition of this embodiment and the other components, is as follows.

(Hydroxy Compound)

The hydroxy compound contains an alcohol or an aromatic hydroxy compound. Preferred for use as alcohols are compounds represented by formula (4) above. Also, preferred for use as aromatic hydroxy compounds are compounds represented by formula (5) above.

(Compound with a Thioureido Group)

The compound with a thioureido group for the composition of this embodiment is a compound represented by formula (6) above.

The production method for a compound with a thioureido group according to this embodiment is not particularly restricted, and any of various publicly known methods may be used. One preferred production method for the compound with a thioureido group is that of a compound with a thioureido group obtained by reacting an organic primary amine and thiourea, and it is preferred to use a compound with a thioureido group obtained by the aforementioned production method for a compound with a thioureido group as mentioned above (step (1) of the first method or step (A) of the third method).

Instead of a compound with a thioureido group produced by the methods described above, for example, there may be used compounds produced by reacting a compound with a thioureylene group and thiourea for conversion of the thioureylene group to a thioureido group.

In such methods, for example, when reaction between an organic primary amine and thiourea is carried out in the presence of a hydroxy compound or the like, an N-substituted O-substituted thiocarbamate will sometimes be produced in addition to the compound with a thioureido group, depending on the reaction conditions and the compounds used, in which case there is no problem with the N-substituted O-substituted thiocarbamate being included in the composition of this embodiment.

(Thiourea Derivative)

The composition of this embodiment may further include at least one type of compound (hereunder referred to as "thiourea derivative") selected from among thiourea ($H_2N$—C(=S)—$NH_2$), N-unsubstituted O-substituted thiocarbamates, thiocarbonic acid esters, dithiobiuret ($H_2N$—C(=S)—NH—C(=S)—$NH_2$) and dithiobiuret derivatives (compounds having a dithiobiuret group (—$NHCSNHCSNH_2$) at an end).

When the compound with a thioureido group is a compound obtained by reacting an organic primary amine and thiourea, the "dithiobiuret derivative" will be a compound derived from the organic primary amine, produced by the reaction.

Generally speaking, when the composition for transporting and storing contains a thiourea derivative, such compounds have active hydrogens and therefore react with the compound with a thioureido group, producing high molecular weight compounds, potentially resulting in the problems of adhesion to the reactor and of solidification. Furthermore, these thiourea derivatives themselves undergo thermal decomposition reaction to generate thermal decomposition products such as ammonia and isothiocyanic acid, sometimes producing insoluble high molecular weight compounds.

However, the present inventors have found that a composition containing a specified amount of a thiourea derivative helps to inhibit alteration reaction of the compound with a ureido group during transport and storage. The present inventors have also found that producing an N-substituted O-substituted thiocarbamate using such a composition has an effect of increasing the yield of the N-substituted O-substituted thiocarbamate. This effect has been hitherto unknown and is a surprising effect. While the mechanism by which the effect is exhibited is not completely understood, the present inventors conjecture that during transport and during storage of the composition, thiourea derivatives might trap trace amounts of contaminating water and oxygen, which inhibits alteration reaction of the compound with a thioureido group.

Thus, a preferred mode of the composition for transporting and storing a compound with a thioureido group according to this embodiment may be a composition in which the compound with a thioureido group is a compound with a thioureido group produced from an organic primary amine and thiourea, the composition further including, in addition to the compound with a thioureido group and the hydroxy compound, at least one type of compound selected from among thiourea, thiocarbonic acid esters, N-unsubstituted O-substituted thiocarbamate, dithiobiuret and dithiobiuret derivatives.

In the composition of this embodiment, the equivalent weight ratio of hydroxy groups of the hydroxy compound with respect to the thioureido groups of the compound with a thioureido group is in the range of 1 to 100. Assuming the mechanism described above, it is preferred to have a lower concentration of the compound with a thioureido group and the thiourea derivative contained in the composition, and it is therefore preferred to have an excess of hydroxy groups with respect to thioureido groups, but on the other hand, using a very large excess of hydroxy compounds may lower the transport efficiency of the compound with a thioureido group, or require an excessively large storage tank for storage. In consideration of the above, the ratio of hydroxy groups to thioureido groups is more preferably 1.5 to 50 and even more preferably 3 to 20.

When the compound with a thioureido group is a compound with a thioureido group obtained by reacting an organic primary amine and thiourea, the amount of thiourea derivative in the composition of this embodiment, i.e. the total number including the number of molecules V of the thiourea, the number of molecules W of the N-unsubstituted O-substituted thiocarbamate, the number of molecules X of the thiocarbonic acid ester, the number of molecules Y of the dithiobiuret and the number Z of terminal dithiobiuret groups of the dithiobiuret derivative (V+W+X+Y+Z) is preferably 0.0001 to 0.05 with respect to the number of carbamate groups of the N-substituted O-substituted thiocarbamate.

As mentioned above, for stabilization of the compound with a thioureido group and increase in the isothiocyanate yield, it is preferred for the composition to contain a certain amount of thiourea derivative. With an excessively large amount of thiourea derivative, however, reaction with the isothiocyanate that is produced during thermal decomposition may result in production of high molecular weight compounds and their adhesion or solidification on the reactor. Thus, the aforementioned total number (V+W+X+Y+Z) is in the range of preferably 0.0001 to 0.03 and more preferably 0.0001 to 0.01 with respect to the compound with a thioureido group. The total number (V+W+X+Y+Z) may be determined by a publicly known method. For example, the composition may be analyzed by a method such as gas chromatography or liquid chromatography, and the components contained in the composition may be identified and quantified. The lower limit for the range is 0.0001, but the present inventors have set this based on the lower detection limit for determining the total number (V+W+X+Y+Z) using gas chromatography and liquid chromatography.

The composition of this embodiment may include components other than the compounds mentioned above (compound with a thioureido group, hydroxy compound and thiourea derivative). Such components may be any compound with a thioureylene group (—NHCSNH—) in the molecular chain, a Fries rearranged N-substituted O-substituted thiocarbamate (providing that the carbamate group is the group derived from the aromatic hydroxy compound), water, an alcohol, an inert gas (for example, nitrogen gas, carbon dioxide gas, argon gas, ammonia gas or the like), or the like.

For explanation of this embodiment, a thioureylene group (—NHCSNH—) may be referred to as a "thiourein group".

There are no particular restrictions on the content of these components, but if undesirable secondary reactions are expected to occur due to the storage temperature or the like, the amount is preferably controlled at all times. The components to be given particular attention are oxygen, ammonia, water, oxidizing substances and reducing substances. The composition for storage according to this embodiment contains a compound including a nitrogen atom, and it is often the case that aromatic hydroxy compounds are oxidized by oxygen, resulting in phenomena such as modification, coloration and the like. In addition, since the composition will in most cases be a flammable composition, the oxygen gas may be controlled by a publicly known method, such as for custody and storage of organic chemical substances conducted in the technical field. For example, the gas phase oxygen concentration in the storage tank may be controlled to an oxygen concentration of no greater than 10%, preferably no greater than 1% and even more preferably no greater than 100 ppm, for example, by a method such as nitrogen purging. When the gas phase portion is to be circulated with an inert gas such as nitrogen, the oxygen concentration in the inert gas is controlled to no greater than 10 ppm.

The composition of this embodiment contains ammonia at preferably 1 to 1000 ppm, more preferably 1 to 300 ppm, even more preferably 1 to 100 ppm, yet more preferably 1 to 50 ppm and most preferably 1 to 10 ppm.

The composition of this embodiment preferably contains no metal components deriving from the catalyst or the like. Results of investigation by the present inventors have demonstrated that such metal components have an effect of tending to cause alteration reaction of the N-substituted O-substituted thiocarbamate. Therefore, the metal component content is preferably no greater than 2000 ppm, more preferably no greater than 600 ppm, even more preferably no greater than 200 ppm and most preferably no greater than 20 ppm.

A lower amount of ammonia is preferred in consideration of equilibrium, as is also known in the prior art, but surprisingly, a low amount has an effect of inhibiting alteration reaction of the N-substituted O-substituted thiocarbamate by metal components and the like in the composition.

The amount of ammonia is the amount of ammonia at the start of transport and storage, and as explained above, it is sometimes consumed by the inhibiting effect of the catalyst component during transport and storage. When the composition for transport and storage has been produced, or adjusted, or when it has been placed in a storage tank or initially transported, the composition for transport and storage preferably has the ammonia amount specified above. The method of adjusting the ammonia amount may be by a publicly known method, for example, using an inert gas such as nitrogen for purging into the liquid phase.

Also, as mentioned above, the metal components in the composition may be metal components derived from the catalyst component referred to below. The metal components include Lewis acids and Lewis acid-producing transition metal compounds, organic tin compounds, copper-based metals, zinc and ferromagnetic metal compounds. Specifically, these include Lewis acids which are typically $AlX_3$, $TiX_3$, $TiX_4$, $VOX_3$, $VX_5$, $ZnX_2$, $FeX_3$ or $SnX_4$ (where X is a halogen or an acetoxy, alkoxy or aryloxy group), or a transition metal compound that produces a Lewis acid; organic tin compounds which are typically $(CH_3)_3SnO\text{-}COCH_3$, $(C2H_5)SnOCOC_6H_5$, $Bu_3SnOCOCH_3$, $Ph_3SnOCOCH_3$, $Bu_2Sn(OCOCH_3)_2$, $Bu_2Sn(OCOC_{11}H_{23})_2$, $Ph_3SnOCH_3$, $(C_2H_5)_3SnOPh$, $Bu_2Sn(OCH_3)_2$, $Bu_2Sn(OC_2H_5)_2$, $Bu_2Sn(OPh)_2$, $Ph_2Sn(CH_3)_2$, $(C_2H_5)_3SnOH$, $PhSnOH$, $Bu_2SnO$, $(C_8H_{17})_2SnO$, $Bu_2SnCl_2$, $BuSnO(OH)$ or the like; copper-based metal compounds such as $CuCl$, $CuCl_2$, $CuBr$, $CuBr_2$, $CuI$, $CuI_2$, $Cu(OAc)_2$, $Cu(acac)_2$, copper olefinates, $Bu_2Cu$, $(CH_3O)_2Cu$, $AgNO_3$, $AgBr$, silver picrate, $AgC_6H_6ClO_4$ and the like; zinc compounds such as $Zn(acac)_2$; ferromagnetic metal compounds such as $Fe(C_{10}H_8)(CO)_5$, $Fe(CO)_5$, $Fe(C4H_6)(CO)_3$, $Co(mesitylene)_2(PEt_2Ph_2)$, $COC_5F_5(CO)_7$ and ferrocene, and the like. Bu stands for butyl, Ph for phenyl and "acac" for an acetylacetone chelate ligand.

Since a high moisture content may produce a phenomenon in which the composition does not become homogeneous, the water concentration, though depending on the makeup of the composition, it is preferably no greater than 10 mass % and preferably no greater than 1 mass % in the composition, and because a large amount of water can cause secondary reactions due to the water when this composition is used as starting material for the N-substituted O-substituted thiocarbamate, it is therefore controlled to even more preferably no greater than 100 ppm. The method of controlling the water may be a publicly known method, such as using a dehydrating agent or desiccant, or distillation under reduced pressure, under pressurization or at ordinary pressure, purging an inert gas into the liquid phase and entraining and removing out the water, or the like. When an oxidizing substance or reducing substance is present, it can potentially cause modification of the hydroxy compound, and therefore such substances are controlled by a publicly known controlling method for hydroxy compounds. An oxidizing substance is a Bronsted acid or Lewis acid, such as an organic acid or inorganic acid, while a reducing substance is a Bronsted base, Lewis base such as an organic base or inorganic base, or hydrogen gas. Excluded from reducing substances are compounds derived from the composition, such as ammonia, or thiourea or other compounds in the composition.

The conditions for storage and transport of the composition of this embodiment are not particularly restricted, but at high temperature the conditions will sometimes have a high tendency to result in thermal decomposition reaction of the compound with a thioureido group. When the flow property or stability is impaired during storage in the range of −40° C. to 280° C., depending on the storage period, the conditions are preferably 0° C. to 260° C. and even more preferably 40° C. to 260° C., but control may be varied according to the purpose of use of the composition, the storage period and the handleability of the composition. The temperature during transport may be within the same range as the temperature during storage, but when the composition is used as starting material for N-substituted O-substituted thiocarbamate production and is to be transported into a reactor for production of an N-substituted O-substituted thiocarbamate, it will usually be preheated to the reaction temperature and then transported to the reactor, and therefore transport may be conducted after confirming that the transport can be safely carried out, depending on the conditions for the reaction step or the accessory devices of the thermal decomposition reactor. Normally, it will be in the range of −40° C. to 280° C., or if the flow property and stability are not impaired, 0° C. to 260° C. and even more preferably 40° C. to 260° C. As mentioned above, the control may be according to the purpose of use of the composition, the transport time and the composition handleability. There are also no particular restrictions on the pressure during transport, but storage may be under reduced pressure conditions to pressurized conditions. Because the hydroxy compound will sometimes distill off if the storage is under reduced pressure, the proportion of the compound with a thioureido group and the hydroxy compound in the composition is controlled to be in the range specified above. There are no particular restrictions on the storage container, tubings, etc. for storage and transport. Taking into account the combustible organic materials, a container is selected in consideration of the flash point of the composition to be handled, as one that conforms to the regulations of the region in which it is to be handled. There are no particular restrictions on the material, and publicly known materials may be used. For example, glass, stainless steel, carbon steel, hastelloy, or glass lined or TEFLON® coated base materials may be used. The storage tank or transport equipment for the composition may have additional known accessory equipment as necessary, including pumps, heat regulators, instrumentation and the like.

The composition for transporting and storing a compound with a thioureido group for this embodiment may be prepared by mixing a compound with a thioureido group, a hydroxy compound and a thiourea derivative in the composition in the range specified above, or it may be prepared by using a composition containing a compound with a thioureido group, that has been obtained by production of a compound with a thioureido group, and from this, adding and/or removing a hydroxy compound or thiourea derivative so that the resulting composition is as specified above.

The composition for transporting and storing for this embodiment may be used most suitably for production of an N-substituted O-substituted thiocarbamate and for a thioisocyanate obtained by thermal decomposition of the compound with a thioureido group. Specifically, the composition for transporting and storing may be transported to a reactor that is to produce an N-substituted O-substituted thiocarbamate, and reacted with a hydroxy compound to produce the N-substituted O-substituted thiocarbamate, or the composition may be transported to a thermal decomposition reactor and supplied for thermal decomposition reaction of the compound with a ureido group contained in the composition to produce an isothiocyanate.

[Isothiocyanate Composition]

The isothiocyanate composition of this embodiment comprises an isothiocyanate and a compound having at least one type of functional group selected from the group consisting of groups represented by the following formula (1) and formula (2).

[Chemical Formula 17]

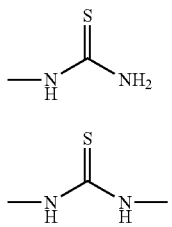

(1)

(2)

While it is difficult to identify all compounds with groups represented by formula (1) and (2), the preferred compounds are of the same type of as that derived from the isothiocyanate contained in the composition. The isothiocyanate is a compound having none of the groups represented by formula (1) and (2). For example, when the isothiocyanate is a compound represented by formula (9) above, the compound having a group represented by formula (1) or (2) may be a compound represented by the following formula (18).

[Chemical Formula 18]

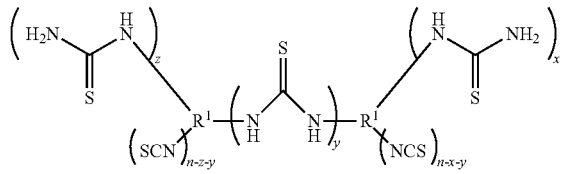

(18)

In the formula, $R^1$ represents a group as defined for formula (3), n represents an integer as defined for formula (3), x, y and z each independently represent an integer of 0 to n, and n-z-y and n-x-y are both an integer of 0 or greater.

When y is 0 in formula (18), the compound is one represented by the following formula (19).

[Chemical Formula 19]

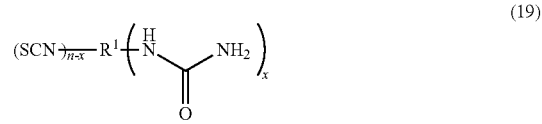

(19)

In the formula, $R^1$ represents a group as defined for formula (3), n represents an integer as defined for formula (3), and x represents an integer as defined for formula (18).

The present inventors have found, surprisingly, that an isothiocyanate composition containing a compound having a group represented by formula (1) or (2) has excellent storage stability, and the present invention has been thereupon completed. While the mechanism by which the compound having a group represented by formula (1) or (2) exhibits such an effect is not fully understood, the present inventors conjecture that the active hydrogens in the compound having a group represented by formula (1) or (2) (in this case, the hydrogens bonded to a nitrogen atom), might trap the trace amounts of water, oxygen, carbon dioxide and the like contaminating during storage, thereby preventing degradation of the isothiocyanate by these compounds.

A preferred isothiocyanate composition containing such compounds is an isothiocyanate composition including isothiocyanate at 97 wt % or greater based on the total mass of the isothiocyanate composition, with the total of the groups represented by formula (1) and (2) being at least 0.1 molppm and no greater than $1.0 \times 10^4$ molppm with respect to the total amount of isothiocyanate groups in the composition.

As mentioned above, in order to eliminate the effects of water, oxygen and the like contaminating during storage, the compound having a group represented by formula (1) and (2) is preferably contained in a large amount in the composition, but if it is contained in a very large amount, on the other hand, this group itself will act on the isothiocyanate group, sometimes resulting in lower stability of the composition. From this viewpoint, the total of the groups represented by formula (1) and (2) is preferably at least 0.1 molppm and no greater than $1.0 \times 10^4$ molppm, more preferably at least 0.3 molppm and no greater than $5.0 \times 10^3$ molppm, even more preferably at least 0.5 molppm and no greater than $3.0 \times 10^3$ molppm, and yet more preferably at least 1.0 molppm and no greater than $1.0 \times 10^3$ molppm.

Also, considering the effect exhibited by hydrogens bonded to nitrogen atoms, the thiocarbamate group will often exhibit a similar effect. When a compound with a thiocarbamate group is present, the amount of thiocarbamate groups is preferably at least 0.1 molppm and no greater than $1.0 \times 10^4$ molppm with respect to the total amount of isothiocyanate groups in the composition.

The groups in the composition can be determined by a publicly known method, for example, a method of direct or indirect quantification of the functional groups by an infrared spectrophotometer, near-infrared spectrophotometer, $^1$H-NMR (for example, with calculation from the integral ratio of the peak corresponding to hydrogens of isothiocyanate groups, and methylene chains or the like adjacent to the group represented by formula (1) or (2)), $^{13}$C-NMR (for example, with calculation from the integral ratio of the peak corresponding to a carbon of an isothiocyanate group or of a thiocarbonyl group bonded to the sulfur atom of a group represented by formula (1) or (2)) or the like, or a method of quantifying each of the compounds in the composition by high-performance liquid chromatography or gas chromatography and calculating the proportion of functional groups based on the weight ratio.

The isothiocyanate composition of this embodiment may contain a solvent so long the gist of the invention is maintained, and there is also no problem if it contains a publicly known stabilizer, catalyst or the like.

The isothiocyanate composition of this embodiment has excellent storage stability, and for example, exhibits an effect not found in the prior art when it is stored in a high temperature, high humidity environment.

The isothiocyanate production method and the composition for production of an isothiocyanate according to this embodiment, as described above, exhibit an effect for convenient production of an isothiocyanate, and the isothiocyanate composition of this embodiment has excellent storage stability.

EXAMPLES

The present invention will now be explained in more specific detail based on examples, with the understanding that the scope of the invention is in no way limited to the examples.

<Analysis Methods>
(1) High-Performance Liquid Chromatography Analysis
(i) Analysis Conditions
Apparatus: High-performance liquid chromatography system LC-10AT
(product of Shimadzu Corp., Japan)
Column: Inertsil-ODS, particle diameter: 5 μm, column diameter: 4.6 mm, length: 150 mm (product of GL Sciences Inc., Japan).
Temperature: 40° C.
Eluent: solution A=acetonitrile, solution B=0.3 wt % aqueous phosphate solution
Flow rate: 1.0 mL/min, as total for solution A and solution B
Gradient:
Initial measurement: 5 vol % solution A/95 vol % solution B
At 15 minutes: 15 vol % solution A/85 vol % solution B
At 20 minutes: 15 vol % solution A/85 vol % solution B
However, from the start of measurement up to 15 minutes after the start of measurement, solution A increases 15 vol % every 10 minutes, while solution B decreases 15 vol % every 10 minutes.
Detector: Ultraviolet detector (measuring wavelength: 210 nm).
Analysis sample injection rate: 10 μL
(ii) High-Performance Liquid Chromatography Analysis Specimen
An analysis specimen was prepared by dissolving 100 mg of sample and 10 mg of 1,1-diethylurea as an internal standard substance in 1.5 g of acetic acid.
(2) Gas Chromatographic Analysis Method
Analyzer: GC-14B by Shimadzu Corp., Japan
Column: Porapack N
Diameter: 3 mm, length: 3 m, SUS
Column temperature: 60° C.
Inlet temperature: 120° C.
Carrier gas: Helium
Carrier gas flow rate: 40 mL/min
Detector: TCD (thermal conductivity detector)
(i) Gas Chromatographic Analysis Sample
A gas sample collected in a Tedlar bag was sampled with a gas-tight syringe and injected.
(ii) Quantitative Analysis
Each standard substance was subjected to analysis, and quantitative analysis was performed on the analysis sample solution based on a drawn calibration curve.
(3) GC-MS Analysis Method
Analyzer: Apparatus connected to GC17A and GCMS-QP5050A by Shimadzu Corp., Japan
Column: DB-1 by Agilent Technologies, USA
Length: 30 m, inner diameter: 0.250 mm, film thickness: 1.00 μm
Column temperature: After holding at 50° C. for 5 minutes, the temperature was raised to 200° C. at a temperature-elevating rate of 10° C./min.
After holding at 200° C. for 5 minutes, the temperature was raised to 300° C. at a temperature-elevating rate of 10° C./min.
Inlet temperature: 300° C.
Interface temperature: 300° C.
(i) GC-MS Analysis Sample
A gas sample collected in a Tedlar bag was sampled with a gas-tight syringe and injected.
(ii) Quantitative Analysis
Each standard substance was subjected to analysis, and quantitative analysis was performed on the analysis sample solution based on a drawn calibration curve. The detection threshold was approximately 1 ppm, in terms of sample concentration.

The amount of "carbonyl groups in the compound with a thiocarbonyl group, contained in the ammonia" is referred to below, and this is the amount calculated by the following procedure.
i) The ammonia-containing gas is subjected to GC-MS analysis by the method indicated above.
ii) The number of thiocarbonyl groups in each molecule of compound detected by GC-MS is calculated.
iii) The total of the amount of each compound as detected by GC-MS (units in mmol) and the total number of thiocarbonyl groups in each compound obtained by multiplication (units in mmol) is calculated, and this total is recorded as the amount of "thiocarbonyl groups in the compound with a thiocarbonyl group, contained in the ammonia". Thus, while this amount does not include the amount of thiocarbonyl groups in the compound with a thiocarbonyl group that is below the detection threshold of GC-MS, the total amount of thiocarbonyl groups that is not included is very small, and therefore it does not hinder in any way the discussion regarding the ratio of "thiocarbonyl groups in the compound with a thiocarbonyl group, contained in the ammonia" and ammonia, for this example.

[Example 1] Production of Octyl Isothiocyanate by First Method

Step (1-1): Production of Compound with Thioureido Group

After placing 3.9 g of octylamine, 4.6 g of thiourea and 140 g of mesitylene in a 500 mL internal volume flask, the interior was exchanged with a nitrogen atmosphere. The flask was immersed in an oil bath that had been heated to 110° C., and the contents were heated while stirring. When heating was performed for 12 hours and then the solution was sampled and analyzed by high-performance liquid chromatography, octylthiourea was found to be produced at a yield of 95% with respect to octylamine. The ammonia concentration of the solution was 15 ppm.

Step (1-2): Thermal Decomposition of Compound with Thioureido Group

The reaction mixture obtained in step (1-1) was placed in a glass tube equipped with a trap bulb, the interior was reduced in pressure to 20 kPa, and heating was performed with a glass tube oven that had been preheated to 250° C. When the liquid collected at the trap bulb was analyzed by high-performance liquid chromatography, octyl isothiocyanate was found to be obtained at a yield of 83% with respect to octylamine.

Example 2

Step (2-1): Production of Compound with Thioureido Group

The same method was carried out as in step (1-1) of Example 1, except that 5.3 g of hexamethylenediamine, 13.9 g of thiourea and 320 g of benzyl ether were placed in a 1 L internal volume flask and the interior was exchanged with a nitrogen atmosphere. Hexamethylenedithioureido was found to be produced at a yield of 93% with respect to hexamethylenediamine. The ammonia concentration of the solution was 10 ppm.

Step (2-2): Thermal Decomposition of Compound with Thioureido Group

The reaction mixture obtained in step (2-1) was used for the same method as step (1-2) of Example 1. When the liquid collected at the trap bulb was analyzed by high-performance liquid chromatography, hexamethylene diisothiocyanate yield was found to be obtained at a yield of 80% with respect to hexamethylenediamine.

Example 3

Step (3-1): Production of Compound with Thioureido Group

The same method was carried out as in step (1-1) of Example 1, except that 22.5 g of isophorone diamine, 63.5 g of thiourea and 1260 g of phenol were placed in a 3 L internal volume flask and the interior was exchanged with a nitrogen atmosphere. Isophorone dithioureido was found to be produced at a yield of 88% with respect to isophorone diamine. The ammonia concentration of the solution was 3250 ppm.

Step (3-2): Removal of Ammonia

After the reaction of step (3-1), a vacuum pump was connected to the flask and the flask interior was brought to 1 kPa. The flask was immersed in an oil bath at 50° C. and heated for 1 hour, at which time the ammonia concentration of the solution was 5 ppm.

Step (3-3): Thermal Decomposition of Compound with Thioureido Group

The same method was carried out as in step (1-3) of Example 1, except that the reaction mixture obtained in step (3-2) was used. When the liquid collected at the trap bulb was analyzed by high-performance liquid chromatography, isophorone diisothiocyanate was found to be obtained at a yield of 78% with respect to isophorone diamine.

Example 4

Step (4-1): Production of Compound with Thioureido Group

The same method was carried out as in step (1-1) of Example 1, except that 90.5 g of aniline, 236 g of thiourea and 2460 g of dibenzyl ether were placed in a 5 L internal volume flask and the interior was exchanged with a nitrogen atmosphere. Phenylthiourea was found to be produced at a yield of 91% with respect to aniline. The ammonia concentration of the solution was 20 ppm.

Step (4-2): Thermal Decomposition of Compound with Thioureido Group

Oil at 250° C. was circulated through the oil jacket of a thin-film evaporator (heat transfer area: 0.1 m$^2$, product of Kobelco Eco-Solutions Co., Ltd.), and the interior was reduced in pressure to 1 kPa. The reaction mixture obtained in step (4-1) was supplied to the thin-film evaporator for thermal decomposition. When the liquid collected at the trap bulb was analyzed by high-performance liquid chromatography, isophorone diisothiocyanate was found to be obtained at a yield of 81% with respect to isophorone diamine.

[Example 5] Production of Octyl Isothiocyanate by Second Method

Step (5-1): Production of Isothiocyanate

After charging 3.9 g of octylamine, 4.6 g of thiourea and 123 g of mesitylene into a 500 mL internal volume flask, the interior was exchanged with a nitrogen atmosphere and a Dimroth condenser was mounted onto the flask. Cooling water at approximately 5° C. was circulated through the cooler. Upon immersing the flask in an oil bath that had been heated to 180° C. while stirring the contents, reflux was initiated. When heating was performed for 3 hours in this state and the reaction mixture was analyzed by high-performance liquid chromatography, octyl isothiocyanate was found to be obtained at a yield of 75% with respect to octylamine.

Example 6

Step (6-1): Production of Isothiocyanate

After charging 5.8 g of allylamine hydrochloride, 7.0 g of thiourea and 310 g of anisole into a 1 L internal volume flask, the interior was exchanged with a nitrogen atmosphere and a Dimroth condenser was mounted onto the flask. Cooling water at approximately 5° C. was circulated through the cooler. Upon immersing the flask in an oil bath that had been heated to 180° C. while stirring the contents, reflux was initiated. When heating was performed for 3 hours in this state and the reaction mixture was analyzed by high-performance liquid chromatography, allyl isothiocyanate was found to be obtained at a yield of 72% with respect to allylamine hydrochloride.

Example 7

Step (7-1): Production of Isothiocyanate

The same method was carried out as in step (5-1) of Example 5, except that 7.8 g of 4,4'-dicyclohexylmethane-diamine, 10.2 g of thiourea and 210 g of mesitylene were used. When the reaction mixture was analyzed by high-performance liquid chromatography, 4,4'-dicyclohexylmethane diisothiocyanate was found to be obtained at a yield of 70% with respect to 4,4'-dicyclohexylmethanediamine.

[Example 8] Production of Octyl Isothiocyanate by Third Method

Step (8-1): Production of Compound with Thioureido Group

After charging 3.9 g of octylamine, 4.6 g of thiourea and 30 g of 2-ethylhexyl alcohol into a 100 mL internal volume flask, the interior was exchanged with a nitrogen atmosphere. The flask was immersed in an oil bath that had been preheated to 150° C., and heating was performed for 5 hours while stirring. When the reaction mixture was analyzed by high-performance liquid chromatography, octylthioureido was found to be obtained at a yield of 95% with respect to octylamine. The ammonia concentration of the solution was 20 ppm.

Step (8-2): Production of N-Substituted O-Substituted Thiocarbamate

After further adding 90 g of 2-ethylhexyl alcohol to the reaction mixture obtained in step (8-1), a Dimroth condenser was mounted onto the flask and cooling water at approximately 5° C. was circulated through the cooler. Upon immersion in an oil bath that had been preheated to 200° C. while stirring the contents of the flask, reflux was initiated. Heating was performed for 5 hours in this state. When the reaction mixture was analyzed by high-performance liquid chromatography, 2-ethylhexyl N-octylthiocarbamate was found to be obtained at a yield of 83% with respect to octylamine, and octyl isothiocyanate was found to be produced at a yield of 8% with respect to octylamine.

Step (8-3): Production of Octyl Isothiocyanate

The reaction mixture of step (8-2) was subjected to vacuum distillation with a rotary evaporator to distill off the 2-ethylhexyl alcohol. The residual solution was placed in a glass tube equipped with a trap bulb, the interior was reduced in pressure to 10 kPa, and heating was performed with a glass tube oven that had been heated to 250° C. When the solution collected at the trap bulb was analyzed by high-performance liquid chromatography, octyl isothiocyanate was obtained at a yield of 51% and 2-ethylhexyl N-octylthiocarbamate was recovered at a yield of 22% with respect to octylamine.

Example 9

Step (9-1): Production of Compound with Thioureido Group

The apparatus shown in FIG. 1 was used. After loading 5.3 kg of hexamethylenediamine, 13.9 kg of thiourea and 133.0 kg of 4-(1,1,3,3-tetramethylbutyl)phenol into a stirring tank 101, the interior was exchanged with a nitrogen atmosphere. The stirring tank 101 was heated at 150° C. for 5 hours. When the reaction mixture was analyzed by high-performance liquid chromatography, hexamethylenedithioureido was found to be obtained at a yield of 93% with respect to hexamethylenediamine. The ammonia concentration of the solution was 4500 ppm.

Step (9-2): Removal of Ammonia

The stirring tank 101 was adjusted to 100° C. and the interior was reduced in pressure to 2 kPa with a vacuum pump. After 3 hours, the ammonia concentration of the solution was 20 ppm.

Step (9-3): Production of N-Substituted O-Substituted Thiocarbamate

The interior of a distillation column 102 packed with Heli-Pak No. 3 was brought to a total reflux state with 4-(1,1,3,3-tetramethylbutyl)phenol. The temperature at the top of the distillation column was 240° C., and the temperature at the condenser 103 was 100° C. The reaction mixture of step (9-3) was supplied through a line 10 simultaneously with closing of the line 14. Also from the line 11 there was supplied 4-(1,1,3,3-tetramethylbutyl)phenol for concentration adjustment. When the condensate that had been condensed at the condenser 103 and collected at the storage tank 104 was analyzed, the condensate was found to contain thiourea, thiobiuret, ammonia and 4-(1,1,3,3-tetramethylbutyl)phenol, with a ratio of 5 for the amount of 4-(1,1,3,3-tetramethylbutyl)phenol with respect to the amount of the compound with a thiocarbonyl group.

When the gas containing ammonia recovered from the line 12 was analyzed, the ammonia was found to contain thiourea and isothiocyanic acid, with a ratio of 0.5 for the number of thiocarbonyl groups with respect to the number of ammonia molecules.

When the reaction mixture recovered in the storage tank 106 was analyzed by high-performance liquid chromatography, N,N'-hexanediyl-di(thiocarbamic acid (4-(1,1,3,3-tetramethylbutyl)phenyl) was found to be obtained at a yield of 81% with respect to hexamethyleneamine, and hexamethylene diisothiocyanate was found to be produced at a yield of 3% with respect to hexamethylenediamine.

Step (9-4): Production of Hexamethylene Diisothiocyanate

A thin-film evaporator 107 (product of Kobelco Eco-Solutions Co., Ltd., heat transfer area: 0.1 m$^2$) was preheated to 280° C., and the reaction mixture recovered in the storage tank 106 was supplied through a line 16. The produced gas component was supplied to a distillation column 108 through a line 18, and distilling separation was performed at the distillation column 108. Hexamethylene diisothiocyanate was extracted from a line 22 provided at a sublevel of the distillation column 108, and recovered to a storage tank 112.

When the hexamethylene diisothiocyanate recovered in the storage tank 112 was analyzed, it was found to be a composition including hexamethylene diisothiocyanate, aminohexylthiourea and 4-(1,1,3,3-tetramethylbutyl)phenol, with an aminohexylthiourea concentration of 15 molppm and a 4-(1,1,3,3-tetramethylbutyl)phenol concentration of 150 wtppm. The hexamethylene diisothiocyanate yield was 75% with respect to hexamethylenediamine.

After repeating step (9-1) to step (9-4) for continuous operation for 100 days, and open examination of the line 12, no adhesion was observed in the interior of the line 12.

Example 10

Step (10-1): Production of Compound with Thioureido Group

The same method was carried out as in Example (9-1).

Step (10-2): Removal of Ammonia

The same method was carried out as in Example (9-2).

Step (10-3): Production of N-Substituted O-Substituted Thiocarbamate

The interior of a distillation column 102 packed with Heli-Pak No. 3 was brought to a total reflux state with 4-(1,1,3,3-tetramethylbutyl)phenol. The temperature at the top of the distillation column was 210° C., and the temperature at the condenser 103 was 100° C. The reaction mixture of step (10-2) was supplied through a line 10 simultaneously with closing of the line 14. Also from the line 11 there was supplied 4-(1,1,3,3-tetramethylbutyl)phenol for concentration adjustment.

When the condensate that had been condensed at the condenser 103 and collected at the storage tank 104 was analyzed, the condensate was found to contain thiourea, thiobiuret, ammonia and 4-(1,1,3,3-tetramethylbutyl)phenol, with a ratio of 4.5 for the amount of 4-(1,1,3,3-tetramethylbutyl)phenol with respect to the amount of the compound with a thiocarbonyl group.

When the gas containing ammonia recovered from the line 12 was analyzed, the ammonia was found to contain thiourea and isothiocyanic acid, with a ratio of 1.2 for the number of thiocarbonyl groups with respect to the number of ammonia molecules.

When the reaction mixture recovered in the storage tank 106 was analyzed by high-performance liquid chromatography, N,N'-hexanediyl-di(thiocarbamic acid (4-(1,1,3,3-tetramethylbutyl)phenyl) was found to be obtained at a yield of 81% with respect to hexamethyleneamine, and hexamethylene diisothiocyanate was found to be produced at a yield of 3% with respect to hexamethylenediamine.

Step (10-4): Production of Hexamethylene Diisothiocyanate

A thin-film evaporator 107 was preheated to 280° C., and the reaction mixture recovered in the storage tank 106 was supplied through a line 16. The produced gas component was supplied to a distillation column 108 through a line 18, and distilling separation was performed at the distillation column 108. Hexamethylene diisothiocyanate was extracted from a line 22 provided at a sublevel of the distillation column 108, and recovered to a storage tank 112.

When the hexamethylene diisothiocyanate recovered in the storage tank 112 was analyzed, it was found to be a composition including hexamethylene diisothiocyanate, aminohexylthiourea and 4-(1,1,3,3-tetramethylbutyl)phenol, with an aminohexylthiourea concentration of less than 0.1 molppm (lower than the detection limit of the analyzer) and a 4-(1,1,3,3-tetramethylbutyl)phenol concentration of 90 wtppm. The hexamethylene diisothiocyanate yield was 68% with respect to hexamethylenediamine.

When step (10-1) to step (10-4) were repeated for continuous operation, the line 12 became blocked on the 88th day.

Example 11

Step (11-1): Production of Compound with Thioureido Group

The same method was carried out as in Example (9-1).

Step (11-2): Removal of Ammonia

The same method was carried out as in Example (9-2).

Step (11-3): Production of N-Substituted O-Substituted Thiocarbamate

The interior of a distillation column 102 packed with Heli-Pak No. 3 was brought to a total reflux state with 4-(1,1,3,3-tetramethylbutyl)phenol. The temperature at the top of the distillation column was 240° C., and the temperature at the condenser 103 was 100° C. The reaction mixture of step (11-2) was supplied through a line 10 simultaneously with closing of the line 14.

When the condensate that had been condensed at the condenser 103 and collected at the storage tank 104 was analyzed, the condensate was found to contain thiourea, thiobiuret, ammonia and 4-(1,1,3,3-tetramethylbutyl)phenol, with a ratio of 0.9 for the amount of 4-(1,1,3,3-tetramethylbutyl)phenol with respect to the amount of the compound with a thiocarbonyl group.

When the gas containing ammonia recovered from the line 12 was analyzed, the ammonia was found to contain thiourea and isothiocyanic acid, with a ratio of 1.2 for the number of thiocarbonyl groups with respect to the number of ammonia molecules.

When the reaction mixture recovered in the storage tank 106 was analyzed by high-performance liquid chromatography, N,N'-hexanediyl-di(thiocarbamic acid (4-(1,1,3,3-tetramethylbutyl)phenyl) was found to be obtained at a yield of 81% with respect to hexamethyleneamine, and hexamethylene diisothiocyanate was found to be produced at a yield of 3% with respect to hexamethylenediamine.

Step (11-4): Production of Hexamethylene Diisothiocyanate

A thin-film evaporator 107 was preheated to 280° C., and the reaction mixture recovered in the storage tank 106 was supplied through a line 16. The produced gas component was supplied to a distillation column 108 through a line 18, and distilling separation was performed at the distillation column 108. Hexamethylene diisothiocyanate was extracted from a line 22 provided at a sublevel of the distillation column 108, and recovered to a storage tank 112.

When the hexamethylene diisothiocyanate recovered in the storage tank 112 was analyzed, it was found to be a composition including hexamethylene diisothiocyanate, aminohexylthiourea and 4-(1,1,3,3-tetramethylbutyl)phenol, with an aminohexylthiourea concentration of 1.2 mol % and a 4-(1,1,3,3-tetramethylbutyl)phenol concentration of 650 ppm. The hexamethylene diisothiocyanate yield was 80% with respect to hexamethylenediamine.

When step (11-1) to step (11-4) were repeated for continuous operation, the condenser 103 became blocked on the 30th day.

Example 12

Step (12-1): Production of Compound with Thioureido Group

The apparatus shown in FIG. 1 was used. The same method was carried out as in step (9-1) of Example 9, except that 3.8 kg of 2,4-toluenediamine, 9.5 kg of thiourea and 63.0 kg of 2-phenylethanol were used. When the reaction mixture was analyzed by high-performance liquid chromatography, 2,4-toluenediureido was found to be obtained at a yield of 95% with respect to 2,4-toluenediamine. The ammonia concentration of the solution was 53 ppm.

Step (12-2): Production of N-Substituted O-Substituted Thiocarbamate

The interior of the distillation column 102 was brought to a total reflux state with 2-phenylethanol. The temperature at the top of the distillation column was 200° C., and the temperature at the condenser 103 was 50° C. The reaction mixture of step (12-1) was supplied through a line 10 simultaneously with closing of the line 14. For adjustment of the concentration, 2-phenylethanol was supplied from the line 11.

When the condensate that had been condensed at the condenser 103 and collected at the storage tank 104 was analyzed, the condensate was found to contain thiourea, thiobiuret, ammonia and 2-phenylethanol, with a ratio of 15 for the amount of 2-phenylethanol with respect to the amount of the compound with a thiocarbonyl group.

When the gas containing ammonia recovered from the line 12 was analyzed, the ammonia was found to contain thiourea and isothiocyanic acid, with a ratio of 0.05 for the number of thiocarbonyl groups with respect to the number of ammonia molecules.

When the reaction mixture collected at the storage tank 106 was analyzed by high-performance liquid chromatography, 2,4-toluenedi(thiocarbamic acid (2-ethylphenyl)) was found to be obtained at a yield of 82% with respect to 2,4-toluenediamine.

Step (12-3): Production of 2,4-Toluene Diisothiocyanate

A thin-film evaporator 107 was preheated to 280° C., and the reaction mixture recovered in the storage tank 106 was supplied through a line 16. The produced gas component was supplied to a distillation column 108 through a line 18, and distilling separation was performed at the distillation column 108. The 2,4-toluene diisothiocyanate was extracted from a line 22 provided at a sublevel of the distillation column 108, and recovered to a storage tank 112. The 2,4-toluene diisothiocyanate yield was 72% with respect to 2,4-toluenediamine.

After repeating step (12-1) to step (12-3) for continuous operation for 120 days, and open examination of the line 12, no adhesion was observed in the interior of the line 12.

[Example 13] Production of Octyl Isothiocyanate by Fourth Method

Step (13-1): Production of N-Substituted O-Substituted Thiocarbamate

After charging 3.9 g of octylamine, 4.6 g of thiourea and 120 g of 2-ethylhexyl alcohol into a 500 mL internal volume flask, the interior was exchanged with a nitrogen atmosphere. A Dimroth condenser was mounted onto the flask and cooling water at approximately 5° C. was circulated through the cooler. Upon immersing the flask in an oil bath that had been preheated to 200° C. while stirring the contents of the flask, reflux was initiated. Heating was performed for 5 hours in this state. When the reaction mixture was analyzed by high-performance liquid chromatography, 2-ethylhexyl N-octylthiocarbamate was found to be obtained at a yield of 75% with respect to octylamine, and octyl isothiocyanate was found to be produced at a yield of 8% with respect to octylamine.

Step (13-2): Production of Octyl Isothiocyanate

The reaction mixture of step (13-1) was subjected to vacuum distillation with a rotary evaporator to distill off the 2-ethyl alcohol. The residual solution was placed in a glass tube equipped with a trap bulb, the interior was reduced in pressure to 10 kPa, and heating was performed with a glass tube oven that had been heated to 250° C. When the solution collected at the trap bulb was analyzed by high-performance liquid chromatography, octyl isothiocyanate was obtained at a yield of 45% and 2-ethylhexyl N-octylthiocarbamate was recovered at a yield of 20% with respect to octylamine.

Example 14

Step (14-1): Production of N-Substituted O-Substituted Thiocarbamate

The apparatus shown in FIG. 1 was used. After loading 4.1 kg of isophorone diamine, 7.3 kg of thiourea and 72.0 kg of 2,6-xylenol in a stirring tank 101, the interior was exchanged with a nitrogen atmosphere and the components were mixed at 50° C. to form a homogeneous solution.

The interior of the distillation column 102 was brought to a total reflux state with 2,6-xylenol. The temperature at the top of the distillation column was 200° C., and the temperature at the condenser 103 was 50° C. The liquid mixture was supplied to the stirring tank 101 through a line 10 simultaneously with closing of the line 14. For adjustment of the concentration, 2,6-xylenol was supplied from the line 11.

When the condensate that had been condensed at the condenser 103 and collected at the storage tank 104 was analyzed, the condensate was found to contain thiourea, thiobiuret, ammonia and 2,6-xylenol, with a ratio of 7 for the amount of 2,6-xylenol with respect to the amount of the compound with a thiocarbonyl group.

When the gas containing ammonia recovered from the line 12 was analyzed, the ammonia was found to contain thiourea and isothiocyanic acid, with a ratio of 0.3 for the number of thiocarbonyl groups with respect to the number of ammonia molecules.

When the reaction mixture recovered in the storage tank 106 was analyzed by high-performance liquid chromatography, 3-((2,6-dimethylphenoxy)thiocarbonylaminomethyl)-3,5,5-trimethylcy clohexylcarbamic acid (2,6-dimethylphenyl) ester was found to be obtained at a yield of 77% with respect to isophorone amine, and isophorone diisothiocyanate was found to be produced at a yield of 1% with respect to isophorone diamine.

Step (14-2): Production of Isophorone Diisothiocyanate

A thin-film evaporator 107 was preheated to 280° C., and the reaction mixture recovered in the storage tank 106 was supplied through a line 16. The produced gas component was supplied to a distillation column 108 through a line 18, and distilling separation was performed at the distillation column 108. The isophorone diisothiocyanate was extracted from a line 22 provided at a sublevel of the distillation column 108, and recovered to a storage tank 112.

When the isophorone diisothiocyanate collected at the storage tank 112 was analyzed, it was found to be a composition including isophorone diisothiocyanate, 3-(aminothiocarbonylamino-methyl)-3,5,5-trimethylcyclohexylamine and 2,6-xylenol, with a 3-(aminothiocarbonylamino-methyl)-3,5,5-trimethylcyclohexylamine concentration of 8 molppm and a 2,6-xylenol concentration of 100 wtppm. The isophorone diisothiocyanate yield was 72% with respect to isophorone diamine.

After repeating step (14-1) to step (14-2) for continuous operation for 120 days, and open examination of the line 12, no adhesion was observed in the interior of the line 12.

Example 15

Step (15-1): Production of N-Substituted O-Substituted Thiocarbamate

The same method was carried out as in step (14-1) of Example 14, except that the temperature at the top of the distillation column was 180° C.

When the condensate that had been condensed at the condenser 103 and collected at the storage tank 104 was analyzed, the condensate was found to contain thiourea, thiobiuret, ammonia and 2,6-xylenol, with a ratio of 7.2 for the amount of 2,6-xylenol with respect to the amount of the compound with a thiocarbonyl group.

When the gas containing ammonia recovered from the line 12 was analyzed, the ammonia was found to contain thiourea and isothiocyanic acid, with a ratio of 1.1 for the number of thiocarbonyl groups with respect to the number of ammonia molecules.

When the reaction mixture recovered in the storage tank 106 was analyzed by high-performance liquid chromatography, 3-((2,6-dimethylphenoxy)thiocarbonylaminomethyl)-3,5,5-trimethylcy clohexylcarbamic acid (2,6-dimethylphenyl) ester was found to be obtained at a yield of 77% with respect to isophorone amine, and isophorone diisothiocyanate was found to be produced at a yield of 1% with respect to isophorone diamine.

Step (15-2): Production of Isophorone Diisothiocyanate

The same method was carried out as in step (14-2) of Example 14, except that the reaction mixture obtained in step (15-1) was used instead of the reaction mixture obtained in step (14-1).

When the isophorone diisothiocyanate collected at the storage tank 112 was analyzed, it was found to be a composition including isophorone diisothiocyanate, 3-(aminothiocarbonylamino-methyl)-3,5,5-trimethylcyclohexylamine and 2,6-xylenol, with a 3-(aminothiocarbonylamino-methyl)-3,5,5-trimethylcyclohexylamine concentration of 8 molppm and a 2,6-xylenol concentration of 100 wtppm. The isophorone diisothiocyanate yield was 72% with respect to isophorone diamine.

When step (15-1) to step (15-2) were repeated for continuous operation, the line 12 became blocked on the 35th day.

Example 16

Step (16-1): Production of N-Substituted O-Substituted Thiocarbamate

The same method was carried out as in step (14-1) of Example 14, except that no 2,6-xylenol was supplied through the line 11. When the condensate that had been condensed at the condenser 103 and collected at the storage tank 104 was analyzed, the condensate was found to contain thiourea, thiobiuret, ammonia and 2,6-xylenol, with a ratio of 0.9 for the amount of 2,6-xylenol with respect to the amount of the compound with a thiocarbonyl group.

When the gas containing ammonia recovered from the line 12 was analyzed, the ammonia was found to contain thiourea and isothiocyanic acid, with a ratio of 0.4 for the number of thiocarbonyl groups with respect to the number of ammonia molecules.

When the reaction mixture recovered in the storage tank 106 was analyzed by high-performance liquid chromatography, 3-((2,6-dimethylphenoxy)thiocarbonylamino-methyl)-3,5,5-trimethylcy clohexylcarbamic acid (2,6-dimethylphenyl) ester was found to be obtained at a yield of 77% with respect to isophorone amine, and isophorone diisothiocyanate was found to be produced at a yield of 1% with respect to isophorone diamine.

Step (16-2): Production of Isophorone Diisothiocyanate

The same method was carried out as in step (14-2) of Example 14, except that the reaction mixture obtained in step (16-1) was used instead of the reaction mixture obtained in step (14-1).

When the isophorone diisothiocyanate collected at the storage tank 112 was analyzed, it was found to be a composition including isophorone diisothiocyanate, 3-(aminothiocarbonylamino-methyl)-3,5,5-trimethylcyclohexylamine and 2,6-xylenol, with a 3-(aminothiocarbonylamino-methyl)-3,5,5-trimethylcyclohexylamine concentration of 8 molppm and a 2,6-xylenol concentration of 100 wtppm. The isophorone diisothiocyanate yield was 72% with respect to isophorone diamine.

When step (16-1) to step (16-2) were repeated for continuous operation, the condenser 103 became blocked on the 34th day.

Example 17

Step (17-1): Production of N-Substituted O-Substituted Thiocarbamate

The apparatus shown in FIG. 1 was used. The same method was carried out as in step (14-1) of Example 14, except that 3.8 kg of 2,4-toluenediamine, 9.5 kg of thiourea and 63.0 kg of 2-phenylethanol were used.

When the condensate that had been condensed at the condenser 103 and collected at the storage tank 104 was analyzed, the condensate was found to contain thiourea, thiobiuret, ammonia and 2-phenylethanol, with a ratio of 13 for the amount of 2-phenylethanol with respect to the amount of the compound with a thiocarbonyl group.

When the gas containing ammonia recovered from the line 12 was analyzed, the ammonia was found to contain thiourea and isothiocyanic acid, with a ratio of 0.1 for the number of thiocarbonyl groups with respect to the number of ammonia molecules.

When the reaction mixture collected at the storage tank 106 was analyzed by high-performance liquid chromatography, 2,4-toluenedi(thiocarbamic acid (2-ethylphenyl)) was found to be obtained at a yield of 78% with respect to 2,4-toluenediamine.

Step (17-2): Production of 2,4-Toluene Diisothiocyanate

A thin-film evaporator 107 was preheated to 280° C., and the reaction mixture recovered in the storage tank 106 was supplied through a line 16. The produced gas component was supplied to a distillation column 108 through a line 18, and distilling separation was performed at the distillation column 108. The 2,4-toluene diisothiocyanate was extracted from a line 22 provided at a sublevel of the distillation column 108, and recovered to a storage tank 112. The 2,4-toluene diisothiocyanate yield was 70% with respect to 2,4-toluenediamine.

After repeating step (17-1) to step (17-2) for continuous operation for 90 days, and open examination of the line 12, no adhesion was observed in the interior of the line 12.

Example 18

A composition including the N-substituted O-substituted thiocarbamate represented by the following formula (20) and phenol (ratio of 50 for the equivalent weight ratio of hydroxy groups of the phenol with respect to the carbamate groups of the N-substituted O-substituted thiocarbamate) was placed in a 10 L SUS storage container up to approximately ½ of the volume, nitrogen exchanged was performed, and it was stored for 800 days in a storage environment in the Kojima area of Kurashiki City, Okayama Prefecture, Japan. During the storage period, the container was thermally insulated with a warm water circulation jacket at approximately 40° C. (controlled within about 30° C. to 50° C.). After storage, the composition was analyzed and the amount of N-substituted O-substituted thiocarbamate was found to be 98 mol % compared to before storage. Also, when thermal decomposition reaction of the N-substituted O-substituted thiocarbamate was conducted using the stored contents, hexamethylene diisothiocyanate was found to be obtained at a yield of 92% with respect to the N-substituted O-substituted thiocarbamate before the thermal decomposition reaction.

[Chemical Formula 20]

(20)

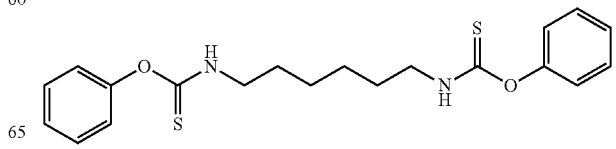

Examples 19 to 38, Comparative Examples 1 and 2

Tables 1 and 2 show the results of storage by the same method as Example 18.

In the tables, "N-substituted O-substituted thiocarbamate" represents the N-substituted O-substituted thiocarbamate in the composition, "ROH" represents the hydroxy compound in the composition, "Equivalent ratio" represents the equivalent weight ratio of hydroxy groups of the hydroxy compound with respect to the carbamate groups of the N-substituted O-substituted thiocarbamate, "Storage yield" represents the yield (mol %) of N-substituted O-substituted thiocarbamate compared to before storage, and "NCS yield" represents the yield of isothiocyanate with respect to N-substituted O-substituted thiocarbamate before thermal decomposition, when an isothiocyanate is produced by thermal decomposition of the N-substituted O-substituted thiocarbamate. Furthermore, when thiourea, N-unsubstituted O-substituted thiocarbamate or the like is included, this is indicated in the column "Other", the numerical value listed in this column representing the equivalent weight ratio of that particular compound with respect to the carbamate groups of the N-substituted O-substituted thiocarbamate.

Incidentally, Comparative Example 2 used naphthalene instead of a hydroxy compound, the amount being indicated as 50 equivalents with respect to the thiocarbamate groups of the N-substituted O-substituted thiocarbamate.

TABLE 1

| | N-substituted O-substituted thiocarbamate | ROH | Equivalent ratio | Other | Storage yield | NCS yield |
|---|---|---|---|---|---|---|
| Example 18 | PhO-C(=S)-NH-(CH₂)₆-NH-C(=S)-OPh | PhOH | 50 | | 98 | 92 |
| Example 19 | n-BuO-C(=S)-NH-(CH₂)₆-NH-C(=S)-O-n-Bu | n-BuOH | 95 | | 90 | 78 |
| Example 20 | (2-ethylhexyl-O)-C(=S)-NH-(CH₂)₆-NH-C(=S)-O-(2-ethylhexyl) | 2-ethylhexanol | 83 | | 90 | 76 |
| Example 21 | (2-ethylhexyl-O)-C(=S)-NH-(CH₂)₆-NH-C(=S)-O-(2-ethylhexyl) | 2-ethylhexanol | 83 | | 98 | 85 |
| Example 22 | (2-ethylhexyl-O)-C(=S)-NH-(CH₂)₆-NH-C(=S)-O-(2-ethylhexyl) | 2-ethylhexanol | 83 | H₂N-C(=S)-NH₂ (0.03) | 97 | 88 |
| Example 23 | (2-ethylhexyl-O)-C(=S)-NH-(CH₂)₆-NH-C(=S)-O-(2-ethylhexyl) | 2-ethylhexanol | 83 | (2-ethylhexyl-O)-C(=S)-NH₂ (0.01) | 97 | 89 |
| Example 24 | (4-C₁₂H₂₅-C₆H₄-O)-C(=S)-NH-(CH₂)₆-NH-C(=S)-O-(C₆H₄-4-C₁₂H₂₅) | PhOH | 10 | (2-ethylhexyl-O)-C(=S)-O-(2-ethylhexyl) (5) | 96 | 90 |

TABLE 1-continued
| | N-substituted O-substituted thiocarbamate | ROH | Equivalent ratio | Other | Storage yield | NCS yield |
|---|---|---|---|---|---|---|
| Example 25 |  |  | 10 | | | |
| | | | 30 | | 0.03 / 95 | 92 |
| Example 26 |  |  | 64 | | 93 | 92 |
| Example 27 |  |  | 60 |  | 0.04 / 90 | 89 |
| Example 28 |  |  | 50 | | 88 | 78 |

TABLE 2

| | N-substituted O-substituted thiocarbamate | ROH | Equivalent ratio | Other | Storage yield | NCS yield |
|---|---|---|---|---|---|---|
| Example 29 | [structure] | [structure: HO-CH2CH2-Ph] | 48 | [structure: H2N-C(=S)-NH-C(=S)-O-CH2CH2-Ph] 0.01 | 92 | 88 |
| Example 30 | [structure] | [structure: 4-(2-phenylpropan-2-yl)phenol] | 15 | | 78 | 76 |
| Example 31 | [structure] | [structure: 4-(2-phenylpropan-2-yl)phenol] | 10 | | | |

TABLE 2-continued

| | N-substituted O-substituted thiocarbamate | ROH | Equivalent ratio | Other | Storage yield | NCS yield |
|---|---|---|---|---|---|---|
| Example 32 | [structure] | phenol | 3 | | 68 | 65 |
| Comp. Example 1 | [structure] | 2-naphthol | 0.5 | | 42 | 60 |
| Example 34 | [structure] | 2-naphthol | 72 | | 75 | 78 |
| Example 35 | [structure] | cyclohexanol | 73 | | 73 | 77 |
| Example 36 | [structure] | cyclohexanol | 60 | | 67 | 73 |
| Comp. Example 2 | [structure] | cyclohexanol | 50 | | 35 | 60 |
| | | naphthalene | | | | |

Example 39

When the reaction mixture obtained in step (9-3) of Example 9 was analyzed, the hydroxy groups of the 4-(1,1,3,3-tetramethylbutyl)phenol in the reaction mixture were at 16 equivalents with respect to the thiocarbamate groups of the N,N'-hexanediyl-di(thiocarbamic acid (4-(1,1,3,3-tetramethylbutyl)phenyl), while the isothiocyanate groups were at 0.03 equivalent. The reaction mixture was stored by the same method as Example 18. After storage, the composition was analyzed and the amount of N-substituted O-substituted thiocarbamate was found to be 95 mol % compared to before storage. Also, when thermal decomposition reaction of the N-substituted O-substituted thiocarbamate was conducted using the stored contents, hexamethylene diisothiocyanate was found to be obtained at a yield of 91% with respect to the N-substituted O-substituted thiocarbamate before the thermal decomposition reaction.

Example 40

When the reaction mixture obtained in step (14-1) of Example 14 was analyzed, the hydroxy groups of the 2,6-xylenol in the reaction mixture were at 16 equivalents with respect to the thiocarbamate groups of the 3-((2,6-dimethylphenoxy)thiocarbonylamino-methyl)-3,5,5-trimethylcy clohexylcarbamic acid (2,6-dimethylphenyl) ester, while the isothiocyanate groups were at 0.013 equivalent. The reaction mixture was stored by the same method as Example 18. After storage, the composition was analyzed and the amount of N-substituted O-substituted thiocarbamate was found to be 98 mol % compared to before storage. Also, when thermal decomposition reaction of the N-substituted O-substituted thiocarbamate was conducted using the stored contents, isophorone diisothiocyanate was found to be obtained at a yield of 90% with respect to the N-substituted O-substituted thiocarbamate before the thermal decomposition reaction.

Example 41

A composition including the compound with a thioureido group represented by the following formula (21) and phenol (ratio of 55 for the equivalent weight ratio of hydroxy groups of the phenol with respect to the amount of thioureido of the compound with a thioureido group) was placed in a 10 L SUS storage container up to approximately ½ of the volume, nitrogen exchanged was performed, and it was stored for 800 days in a storage environment in the Kojima area of Kurashiki City, Okayama Prefecture, Japan. During the storage period, the container was thermally insulated with a warm water circulation jacket at approximately 40° C. (controlled within about 30° C. to 50° C.). After storage, the composition was analyzed and the amount of thioureido groups was found to be 95 mol % compared to before storage.

[Chemical Formula 21]

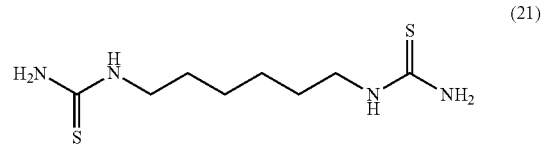

(21)

Examples 42 to 59, Comparative Examples 3 and 4

Tables 3 and 4 show the results of storage by the same method as Example 41.

In the tables, "Compound with thioureido group" represents the compound with a thioureido group in the composition, "ROH" represents the hydroxy compound in the composition, "Equivalent ratio" represents the equivalent weight ratio of the hydroxy groups of the hydroxy compound with respect to the thioureido groups of the compound with a thioureido group, and "Storage yield" represents the yield (mol %) of the compound with a thioureido group compared to before storage. Furthermore, when thiourea, N-unsubstituted O-substituted thiocarbamate or the like is included, this is indicated in the column "Other", the numerical value listed in this column representing the equivalent ratio of that particular compound with respect to the thioureido groups of the compound with a thioureido group.

Incidentally, Comparative Example 4 used tetralin instead of a hydroxy compound, the amount being indicated as 70 equivalents with respect to the thioureido groups of the compound with a thioureido group.

| | Compound with thioureido group | ROH | Equivalent ratio | Other | Storage yield |
|---|---|---|---|---|---|
| Example 41 | H₂N-C(=S)-NH-(CH₂)₆-NH-C(=S)-NH₂ | phenol | 58 | | 95 |
| Example 42 | H₂N-C(=S)-NH-(CH₂)₆-NH-C(=S)-NH₂ | n-butanol | 81 | | 90 |
| Example 43 | H₂N-C(=S)-NH-(CH₂)₆-NH-C(=S)-NH₂ | 2-ethylhexanol | 36 | H₂N-C(=S)-NH₂ | 77 |
| Example 44 | H₂N-C(=S)-NH-(CH₂)₆-NH-C(=S)-NH₂ | 2-ethylhexanol | 37 | 2-ethylhexyl carbamothioate (H₂N-C(=S)-O-CH₂CH(C₂H₅)C₄H₉) | 93, 0.01, 0.01 |
| Example 45 | H₂N-C(=S)-NH-(CH₂)₆-NH-C(=S)-NH₂ | 2-ethylhexanol | 36 | H₂N-C(=S)-NH-C(=S)-NH₂ | 93, 0.01, 0.03 |

-continued

| | Compound with thioureido group | ROH | Equivalent ratio | Other | | Storage yield |
|---|---|---|---|---|---|---|
| Example 46 | H₂N-C(=S)-NH-(CH₂)₆-NH-C(=S)-NH₂ | 2-ethylhexanol | 83 | bis(2-ethylhexyl) thiocarbonate | 0.05 | 92 |
| Example 47 | H₂N-C(=S)-NH-(CH₂)₆-NH-C(=S)-NH₂ | phenol | 20 | 2-ethylhexyl thiocarbamate | 0.01 | 94 |
| | | 4-dodecylphenol ($C_{12}H_{25}$) | 15 | | | |
| Example 48 | isophorone bis(thiourea) derivative | phenol | 30 | | | 95 |

-continued

| Example | Compound with thioureido group | ROH | Equivalent ratio | Other | Storage yield |
|---|---|---|---|---|---|
| Example 49 | (thiourea-substituted trimethylcyclohexane-methyl thiourea) | 2-phenylethanol (HO-CH2CH2-Ph) | 84 | | 86 |
| Example 50 | (thiourea-substituted trimethylcyclohexane-methyl thiourea) | 4-(2-phenylpropan-2-yl)phenol | 22 | dithiobiuret (H2N-C(=S)-NH-C(=S)-NH2) 0.04 | 79 |
| Example 51 | (thiourea-substituted trimethylcyclohexane-methyl thiourea) | 4-(2-phenylpropan-2-yl)phenol | 24 | | 88 |

TABLE 4

| | Compound with thioureido group | ROH | Equivalent ratio | Other | Storage yield |
|---|---|---|---|---|---|
| Example 52 | H₂N-C(S)-NH-[3,3,5-trimethylcyclohexyl]-CH₂-NH-C(S)-NH₂ | HO-CH₂CH₂-C₆H₅ | 82 | H₂N-C(S)-NH-C(S)-O-CH₂CH₂-C₆H₅  0.01 | 92 |
| Example 53 | [methyl-phenyl bis(thiourea)] | HO-C₆H₄-O-C₆H₅ | 20 | | 81 |
| Example 54 | [methyl-phenyl bis(thiourea)] | HO-naphthyl | 11 | | 77 |
| | | HO-C₆H₅ (phenol) | 5 | | |
| Example 55 | H₂N-C(S)-NH-C₆H₄-CH₂-C₆H₄-NH-C(S)-NH₂ | HO-cyclohexyl | 1.5 | | 65 |
| Comp. Example 3 | H₂N-C(S)-NH-C₆H₄-CH₂-C₆H₄-NH-C(S)-NH₂ | HO-cyclohexyl | 0.4 | | 33 |
| Example 57 | H₂N-C(S)-NH-C₆H₄-CH₂-C₆H₄-NH-C(S)-NH₂ | HO-naphthyl | 70 | | 79 |
| Example 58 | C₆H₅-NH-C(S)-NH₂ | HO-C₆H₅ | 29 | | 74 |
| Example 59 | H₂N-C(S)-NH-CH₂CH=CH₂ | HO-CH₂CH₂CH₂CH₃ | 68 | | 76 |

TABLE 4-continued

| | Compound with thioureido group | ROH | Equivalent ratio | Other | Storage yield |
|---|---|---|---|---|---|
| Comp. Example 4 | H₂N–C(S)–NH–C₆H₄–CH₂–C₆H₄–NH–C(S)–NH₂ | tetralin | 70 | | 34 |

Example 60

After mixing the isothiocyanate represented by the following formula (22) and the compound represented by the following formula (23), the mixture was placed in a 10 L SUS storage container to approximately ½ of the volume, nitrogen exchanged was performed, and it was stored for 800 days in a storage environment in the Kojima area of Kurashiki City, Okayama Prefecture, Japan. During the storage period, the container was thermally insulated with a warm water circulation jacket at approximately 40° C. (controlled within about 30° C. to 50° C.). After storage, the composition was analyzed and the amount of thioureido groups was found to be 90 mol % compared to before storage.

[Chemical Formula 22]

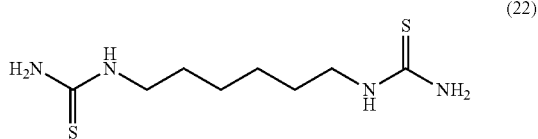
(22)

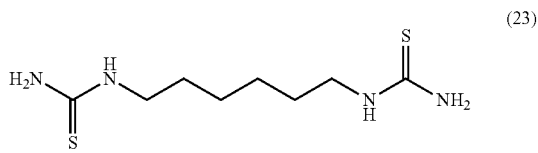
(23)

Examples 60 to 66, Comparative Example 5

Table 5 shows the results of storage by the same method as Example 60.

In the table, "Storage yield" represents the yield (mol %) of isothiocyanate compared to before storage.

TABLE 5

| | Isothiocyanate | Content | Non-isothiocyanate compounds in composition | Amount represented by formulas (1) and (2) (with respect to total isothiocyanate groups) | Storage yield |
|---|---|---|---|---|---|
| Example 60 | SCN~~~NCS | 98.3 wt % | SCN~~~N(H)-C(=S)-N(H)~~~NCS | 0.96 × 10⁴ molppm | 90 |
| Example 61 | SCN~~~NCS | 99.3 wt % | H₂N-C(=S)-N(H)~~~NH-C(=S)-NH₂ | 0.48 × 10⁴ molppm | 92 |
| Example 62 | SCN~~~NCS | 98.9 wt % | H₂N-C(=S)-N(H)~~~SCN ; phenol | 0.22 × 10⁴ molppm | 92 |
| Example 63 | SCN~~~NCS | 98.9 wt % | H₂N-C(=S)-N(H)~~~SCN ; H₂N-C(=S)-N(H)~~~N(H)-C(=S)-NH₂ | 0.45 × 10⁴ molppm | 93 |

TABLE 5-continued

| | Isothiocyanate | Content | Non-isothiocyanate compounds in composition | Amount represented by formulas (1) and (2) (with respect to total isothiocyanate groups) | Storage yield |
|---|---|---|---|---|---|
| Example 64 | [3-isothiocyanatomethyl-3,5,5-trimethylcyclohexyl isothiocyanate structure] | 99.5 wt % | [thiourea derivatives and 2-ethylhexanol structures] | 0.28 × 10⁴ molppm | 92 |
| Example 65 | [4,4'-methylenebis(cyclohexyl isothiocyanate) structure] | 99.7 wt % | [bis-thiourea derivatives of dicyclohexylmethane] | 2.1 × 10⁴ molppm | 94 |

TABLE 5-continued

| | Isothiocyanate | Content | Non-isothiocyanate compounds in composition | Amount represented by formulas (1) and (2) (with respect to total isothiocyanate groups) | Storage yield |
|---|---|---|---|---|---|
| Example 66 | SCN–[cyclohexyl-CH2-cyclohexyl]–NCS | 99.5 wt % | H2N-C(=S)-NH–[cyclohexyl-CH2-cyclohexyl]–NH-C(=S)-NH2; HO-CH2CH2-phenyl | 16 molppm | 96 |
| Comp. Example 5 | SCN–(CH2)6–NCS | 98.0 wt % | H2N-C(=S)-NH–[cyclohexyl-CH2-cyclohexyl-CH2-cyclohexyl]–NH-C(=S)-NH2; SCN–(CH2)6–NH-C(=S)-NH–(CH2)6–NCS | 1.1 × 10^4 molppm | 73 |

Example 67

Step (67-1): Production of N-Substituted O-Substituted Thiocarbamate

Figure 2:
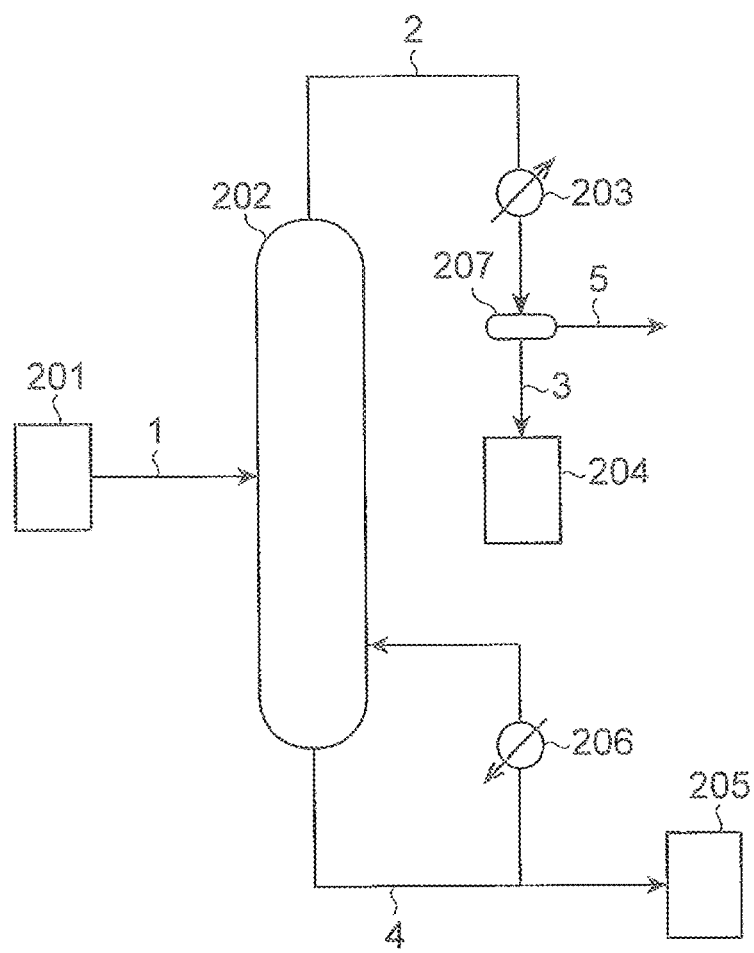
FIG. 2 is a conceptual drawing showing an example of a production apparatus for an N-substituted O-substituted thiocarbamate.

Production of an N-substituted O-substituted thiocarbamate was carried out with a reactor such as shown in FIG. 2.

A starting solution was prepared by mixing 330 g of hexamethylenediamine, 8510 g of 4-(1,1,3,3-tetramethylbutyl)phenol and 463 g of thiourea. A packed tower (reactor) 202 with an inner diameter of 20 mm, packed with a filler (Heli-Pak No. 3), was heated to 240° C., and the interior was adjusted to a pressure of approximately 20 kPa. A liquid mixture having the same composition as the starting solution was introduced through a line 1 provided at the top end of the packed tower 202, and after stabilization of the operating conditions, the starting solution was introduced at approximately 1.0 g/min, and the reaction mixture was recovered in a storage tank 205 through a line 4 provided at the lowermost section of the packed tower 202. The gas phase component was collected from a line 2 provided at the uppermost section of the packed tower 202, and the component obtained by condensation at the condenser 203 that had been kept at approximately 85° C. was collected in the storage tank 204. The amount of reaction mixture collected at the storage tank 205 was 4.69 kg. When the reaction mixture was analyzed by liquid chromatography and $^1$H-NMR, the reaction mixture was found to contain N,N'-hexanediyl-di(thiocarbamic acid (4-(1,1,3,3-tetramethylbutyl)phenyl) ester), with a yield of approximately 85% with respect to hexamethylenediamine.

When the component collected in the other storage tank 204 was analyzed by $^1$H-NMR and $^{13}$C-NMR, it was found to be a mixture of 4-(1,1,3,3-tetramethylbutyl)phenol and thiourea, with a thiourea content of about 286 g (3.77 mol) and a 4-(1,1,3,3-tetramethylbutyl)phenol content of 4.05 kg (19.6 mol). Also, ammonia-containing gas was discharged from a line 5 provided at the top of the storage tank 204. The gas was collected in a Tedlar bag, and the gas was injected for gas chromatography using a gas-tight syringe for analysis of the gas component. As a result, the ammonia recovery per 100 minutes was 0.871 g (51 mmol). Also, when the gas was analyzed by GC-MS, the carbonyl group content in the compound with a carbonyl group in the ammonia was found to be 0.002 mmol.

When step (67-1) was continued, no blockage of the ammonia discharge line was observed even with an operation time exceeding 380 days.

Figure 3:
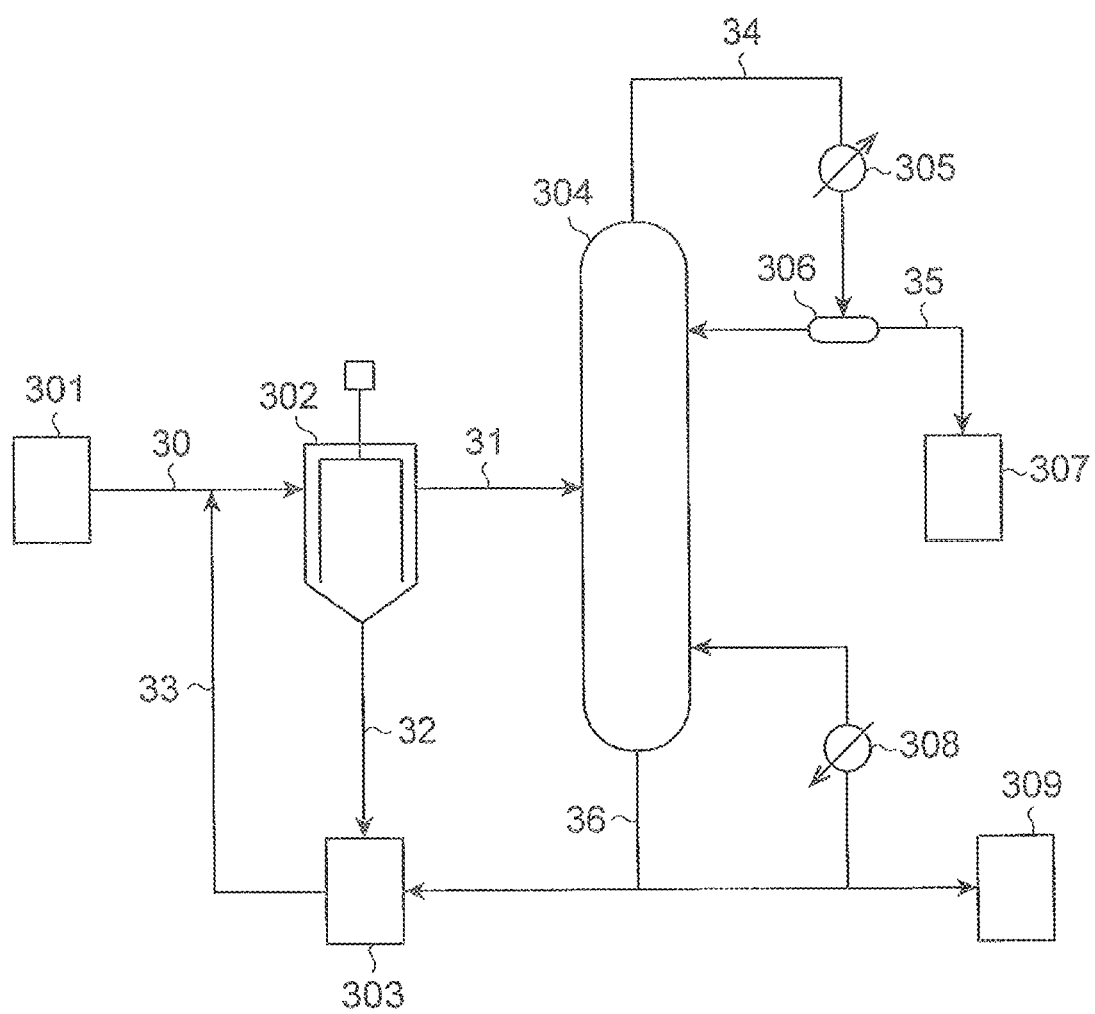
FIG. 3 is a conceptual drawing showing an example of an isothiocyanate production apparatus.

Step (67-2): Production of Isothiocyanate by Thermal Decomposition of N-Substituted O-Substituted Thiocarbamate The apparatus shown in FIG. 3 was used for isothiocyanate production.

A thin-film distillation apparatus 302 was heated to 300° C., and the pressure in the thin-film distillation apparatus was adjusted to approximately 1.3 kPa. The reaction mixture collected in the storage tank 205 in Example 67 was loaded into a storage tank 301, and supplied to the thin-film distillation apparatus at about 1800 g/hr through a line 30. The liquid component was extracted from a line 32 provided at the bottom section of the thin-film distillation apparatus 302, and collected in a storage tank 303. The liquid component collected in the storage tank 303 was again supplied to the thin-film distillation apparatus 302 through a line 33. A gas component including hexamethylene diisothiocyanate and 4-(1,1,3,3-tetramethylbutyl)phenol was extracted through a line 31 provided at the top section of the thin-film distillation apparatus 302. The gas component was introduced into a distillation column 204 for distilling separation of the hexamethylene diisothiocyanate and 4-(1,1,3,3-tetramethylbutyl)phenol. A portion of the high-boiling component including 4-(1,1,3,3-tetramethylbutyl)phenol was returned to the storage tank 303 through a line 36 provided at the bottom section of the distillation column 304, and a portion was supplied back to the distillation column 304 through a reboiler 308, while the remainder was collected at a storage tank 309. The gas phase component containing hexamethylene diisothiocyanate was extracted from the top of the distillation column 304 through a line 34 and condensed at a condenser 305, and a portion of the condensate was returned to the distillation column 304. The condensate was obtained in a storage tank 307.

When the condensate was analyzed by $^1$H-NMR and gas chromatography, the condensate was found to be a solution containing 99 wt % hexamethylene diisothiocyanate. The hexamethylene diisothiocyanate yield was 78% with respect to hexamethylenediamine.

Example 68

Step (68-1): Production of N-Substituted Thiocarbamic Acid Ester

The same method was carried out as in step (67-1) of Example 67, except that 210 g of 2,4-toluenediamine, 9220 g of 4-(1,1,3,3-tetramethylbutyl)phenol and 325 g of thiourea were mixed to form a starting solution, the packed tower 202 was heated to 240° C., the interior pressure was approximately 52 kPa, the condenser was kept at 120° C., and the starting solution was introduced at about 1.0 g/min. When the obtained reaction mixture was analyzed by liquid chromatography and $^1$H-NMR, the reaction mixture was found to contain toluene-2,4-di(thiocarbamic acid (4-(1,1,3,3-tetramethylbutyl)phenyl) ester), with a yield of approximately 83% with respect to 2,4-toluenediamine.

Also, ammonia-containing gas was discharged from a line 25 provided at the top of the storage tank 204. The gas was collected in a Tedlar bag, and the gas was injected for gas chromatography using a gas-tight syringe for analysis of the gas component. As a result, the ammonia recovery per 100 minutes was 0.624 g (38 mmol). When the gas was analyzed by GC-MS, the carbonyl group content in the compound with a carbonyl group in the ammonia was found to be 0.02 mmol.

When step (68-1) was continued, no blockage of the ammonia discharge line was observed even with an operation time exceeding 380 days.

Example 69

Step (69-1): Production of N-Substituted Thiocarbamic Acid Ester

The same method was carried out as in step (67-1) of Example 67, except that 350 g of 3-aminomethyl-3,5,5-trimethylcyclohexylamine, 3100 g of 4-phenylphenol and 391 g of thiourea were mixed to form a starting solution, the packed tower 202 was heated to 240° C., the interior pressure was approximately 26 kPa, the condenser was kept at about 150° C., and the starting solution was introduced at about 1.2 g/min. When the obtained reaction mixture was analyzed by liquid chromatography and $^1$H-NMR, the reaction mixture was found to be a solution including 3-((4-phenylphenoxy)thiocarbonylamino-methyl)-3,5,5-trimethylcycloh exylthiocarbamic acid (4-phenylphenyl) ester, with a yield of approximately 83% with respect to 3-aminomethyl-3,5,5-trimethylcyclohexylamine.

Also, ammonia-containing gas was discharged from a line 25 provided at the top of the storage tank 204. The gas was collected in a Tedlar bag, and the gas was injected for gas chromatography using a gas-tight syringe for analysis of the gas component. As a result, the ammonia recovery per 100 minutes was 1.8 g (106 mmol). When the gas was analyzed by GC-MS, the carbonyl group content in the compound with a carbonyl group in the ammonia was found to be 0.51 mmol.

When step (69-1) was continued, no blockage of the ammonia discharge line was observed even with an operation time exceeding 380 days.

Step (69-2): Production of Isothiocyanate by Thermal Decomposition of N-Substituted Thiocarbamic Acid Ester The same method was carried out as in step (67-2) of Example 67, except that the thin-film distillation apparatus 202 was heated to 220° C., the pressure in the thin-film distillation apparatus was approximately 1.3 kPa, and instead of the reaction mixture collected in the storage tank 205 in Example 67, the reaction mixture collected in the storage tank 205 in step (69-1) of Example 69 was supplied to the thin-film distillation apparatus at about 660 g/hr.

When the condensate obtained in the storage tank 307 was analyzed by $^1$H-NMR and gas chromatography, the condensate was found to be a solution containing 99 wt % isophorone diisothiocyanate, with an isophorone diisothiocyanate yield of 73% with respect to 3-(aminomethyl)-3,3,5-trimethylcyclohexylamine.

Example 70

Step (70-1): Production of Thiocarbamic Acid Ester

Figure 4:
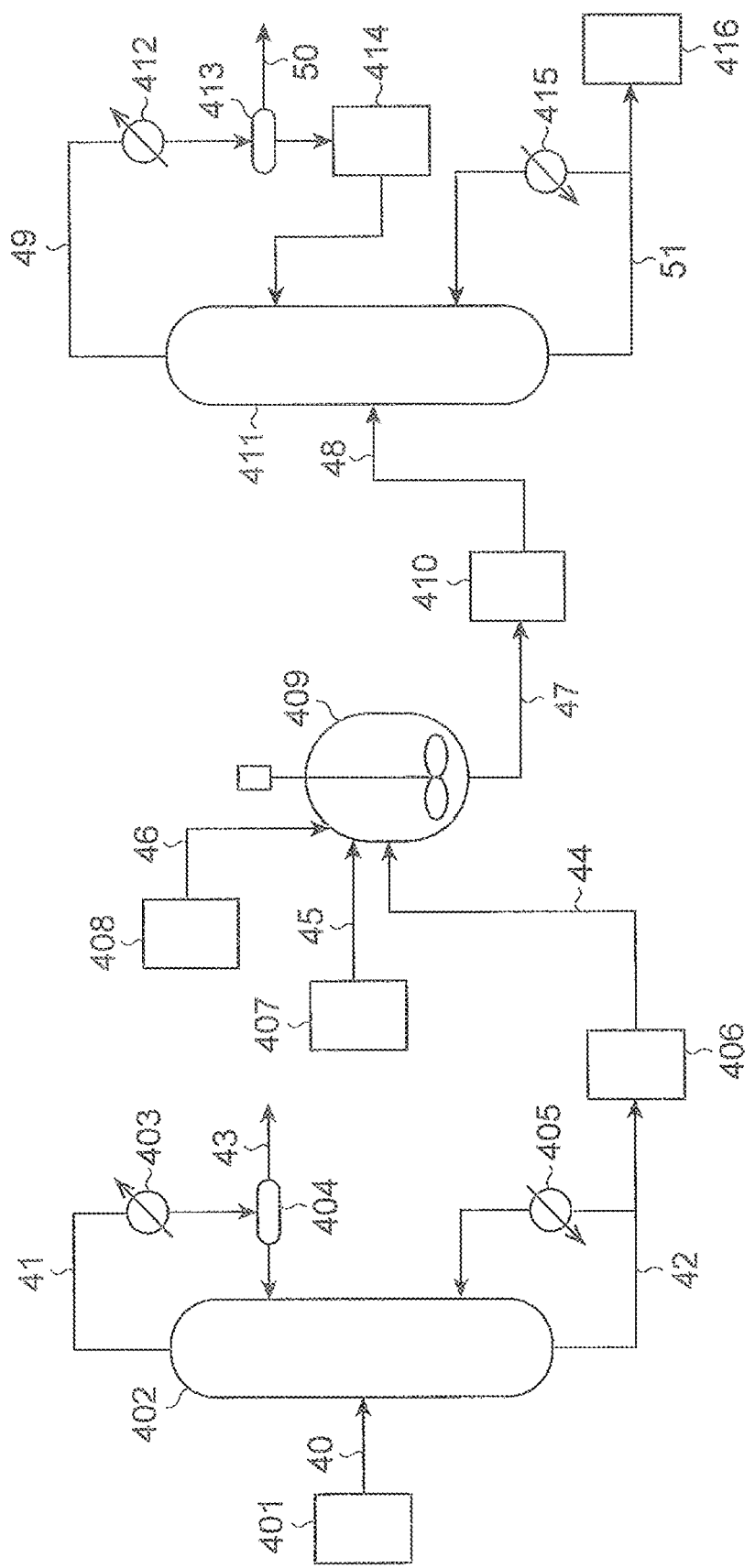
FIG. 4 is a conceptual drawing showing an example of an N-substituted O-substituted thiocarbamate production apparatus.

In step (70-1), the reactor shown in FIG. 4 was used.

A liquid mixture of 3.48 kg of thiourea and 48.5 kg of 4-(1,1,3,3-tetramethylbutyl)phenol was loaded into a storage tank 401. A packed tower 402 with an inner diameter of 20 mm, packed with a filler (Heli-Pak No. 3), was heated to 150° C., and the interior pressure was adjusted to 30 kPa. The thiourea and 4-(1,1,3,3-tetramethylbutyl)phenol mixture was fed from the storage tank 401 to the packed tower 402, and the reaction mixture was collected in a storage tank 406 through a line 42 provided at the lowermost section of the packed tower 402. The gas phase component was introduced into the condenser 403 from the top of the packed tower 402 through a line 41, the condensate was circulated into the packed tower 402, and the gaseous ammonia was discharged from a line 43. When the reaction product collected in the storage tank 406 was analyzed by liquid chromatography, the reaction product was found to be a mixture containing 21 wt % thiocarbamic acid (4-(1,1,3,3-tetramethylbutyl)phenyl).

Step (70-2): Production of Compound with Thioureido Group

In step (70-2), the reactor shown in FIG. 4 was subsequently used.

With the line 46 in a closed state, the mixture in the storage tank 406 was loaded into a stirring tank 409 that had been heated to 120° C. While stirring the stirring tank 409, 1.83 kg of hexamethylenediamine was supplied to the stirring tank 409 from a storage tank 407 through a line 45, at a rate of about 20 g/min. After supply of the hexamethylenediamine was complete, stirring was continued for approximately 10 hours and the reaction mixture was sampled. As a result of analyzing the reaction mixture by liquid chromatography, it was found to contain 1,6-hexamethylenedithiourea, with a yield of 95% with respect to hexamethylenediamine. A line 47 was opened, and the reaction mixture was transported to a storage tank 410 through the line 47.

Step (70-3): Production of N-Substituted Thiocarbamic Acid Ester

In step (70-3), the reactor shown in FIG. 4 was subsequently used.

A packed tower 411 with an inner diameter of 40 mm, packed with a filler (Heli-Pak No. 3), was heated to 240° C., the interior pressure was adjusted to 26 kPa, and the condenser was kept at 90° C. The reaction mixture obtained in step (70-2) was fed through a line 48 provided in the packed tower 411 at approximately 5 g/min. As the initial stage of the reaction was in a non-steady state, the sample was discarded. After a steady state was reached, the fed reaction mixture was about 43.3 kg. It was collected in a storage tank 416 through a line 51 provided at the lowermost section of the packed tower 411. The gas phase component from a line 49 provided at the uppermost section of the packed tower 411 was condensed at a condenser 413 kept at approximately 85° C., and the obtained liquid phase component was collected in a storage tank 414 through a gas-liquid separator 413. When the reaction mixture collected in the storage tank 416 was analyzed by liquid chromatography and $^1$H-NMR, the reaction mixture was found to be a composition containing N,N'-hexanediyl-di(thiocarbamic acid (4-(1,1,3,3-tetramethylbutyl)phenyl) ester). The yield of N,N'-hexanediyl-di(carbamic acid (4-(1,1,3,3-tetramethylbutyl)phenyl) ester) with respect to hexamethylenediamine was approximately 83%. When the component collected in the other storage tank 414 was analyzed by $^1$H-NMR and $^{13}$C-NMR, it was found to be a mixture of 4-(1,1,3,3-tetramethylbutyl)phenol, thiourea and thiocarbamic acid (4-(1,1,3,3-tetramethylbutyl)phenyl), with a 4-(1,1,3,3-tetramethylbutyl)phenol content of 1.57 kg (7.67 mol), a thiourea content of about 41.9 g (0.55 mol), and a thiocarbamic acid (4-(1,1,3,3-tetramethylbutyl)phenyl) content of 1.33 kg (5.33 mol).

The ammonia discharged from the gas-liquid separator 413 through a line 50 was collected in a Tedlar bag, and the gas was injected for gas chromatography using a gas-tight syringe for analysis of the gas component. As a result, the ammonia recovery per 100 minutes was 2.07 g (0.12 mol). Also, when the gas was analyzed by GC-MS, the carbonyl group content in the compound with a carbonyl group in the ammonia was found to be 0.032 mmol.

When step (70-1) to step (70-3) were continued, no blockage of the ammonia discharge line was observed even with an operation time exceeding 380 days.

Example 71

Step (71-1): Production of Compound with Ureido Group

Figure 5:
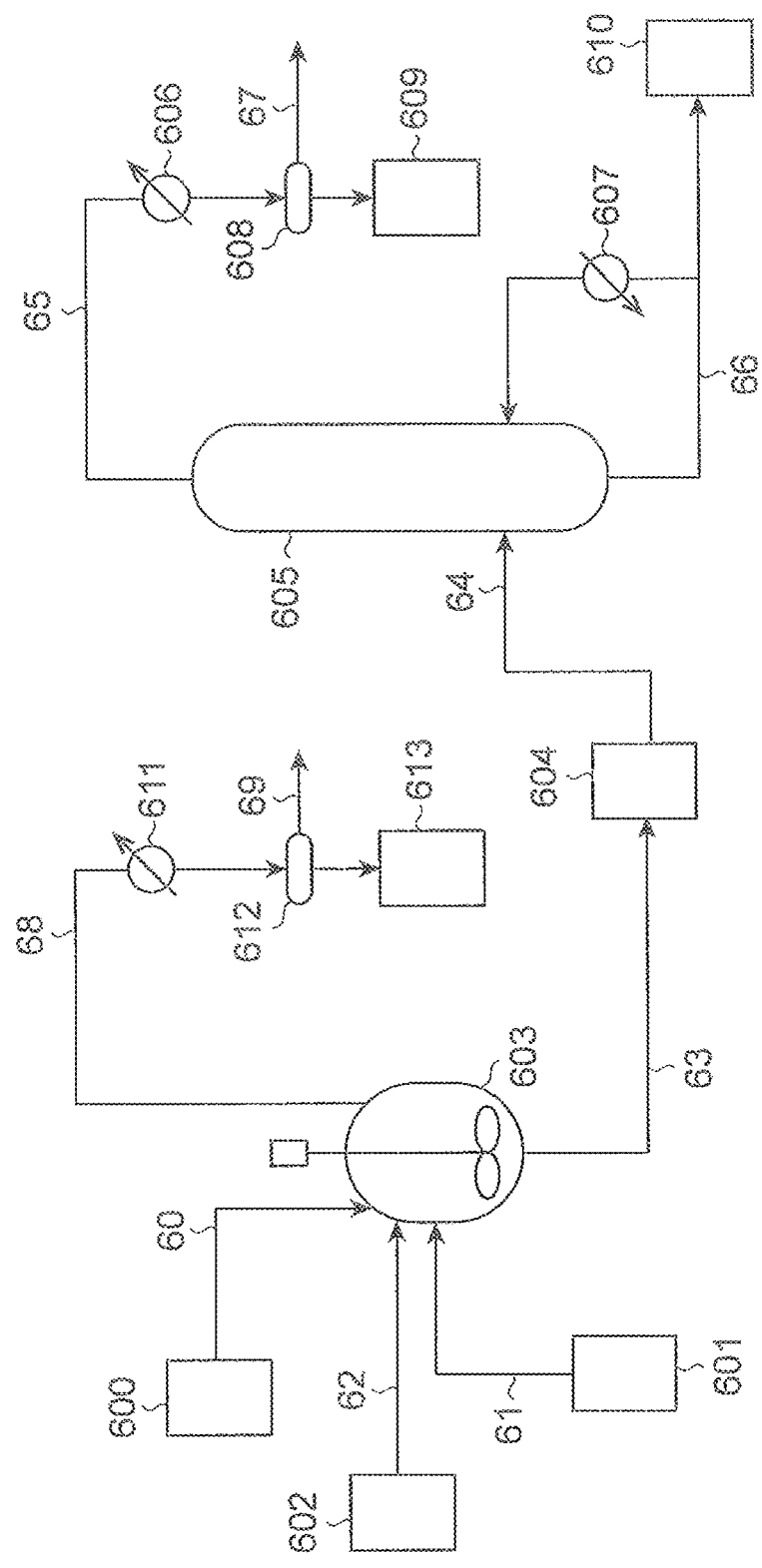
FIG. 5 is a conceptual drawing showing an example of an N-substituted O-substituted thiocarbamate production apparatus.

In step (71-1), the reactor shown in FIG. 5 was used.

With the line 63 in a closed state, 31.3 kg of 2,4-di-tert-amylphenol and 4.36 kg of thiourea were mixed in a storage tank 601 that had been heated to 120° C., and the liquid mixture was transported to a stirring tank 603 (internal volume: 80 L, baffle-equipped) that had been heated to 120° C. While stirring the stirring tank 603, 1.66 kg of hexamethylenediamine was supplied to the stirring tank 603 from a storage tank 602 through a line 62, at a rate of about 20 g/min. After supply of the hexamethylenediamine was complete, stirring was continued for approximately 10 hours. A line 63 was opened, and the reaction mixture was transported to a storage tank 604 through the line 63. As a result of analyzing the reaction mixture by liquid chromatography, it was found to contain 1,6-hexanedithiourea, with a yield of about 84% with respect to hexamethylenediamine.

Step (71-2): Production of N-Substituted Thiocarbamic Acid Ester

In step (71-2), the reactor shown in FIG. 5 was subsequently used.

A packed tower 605 with an inner diameter of 40 mm and a height of 4000 mm, packed with a filler (Heli-Pak No. 3), was heated to 240° C., and the interior pressure was adjusted to 26 kPa. The reaction mixture obtained in step (71-1) was fed through a line 64 provided in the packed tower 605 at approximately 3.5 g/min. As the initial stage of the reaction was in a non-steady state, the sample was discarded. After a steady state was reached, the fed reaction mixture was about 30.8 kg. It was collected in a storage tank 610 through a line 66 provided at the lowermost section of the packed tower 605. The gas phase component from a line 65 provided at the uppermost section of the packed tower 605 was condensed at a condenser 606 kept at approximately 60° C., and the obtained liquid phase component was collected in a storage tank 609 through a gas-liquid separator 608. When the obtained reaction mixture was analyzed by liquid chromatography and $^1$H-NMR, the reaction mixture was found to be a composition containing N,N'-hexanediyl-di(thiocarbamic acid (2,4-di-tert-amylphenyl) ester), with a N,N'-hexanediyl-di(thiocarbamic acid (2,4-di-tert-amylphenyl) ester) yield of approximately 74% with respect to hexamethylenediamine. When the component collected in the storage tank 609 was also subjected to $^1$H-NMR and $^{13}$C-NMR measurement, it was found to be a mixture of 2,4-di-tert-amylphenol, thiourea and (2,4-di-tert-amylphenyl) thiocarbamate, with a 2,4-di-tert-amylphenol content of about 4.23 kg (18.1 mol), a thiourea content of about 0.55 kg (7.2 mol) and a (2,4-di-tert-amylphenyl) thiocarbamate content of about 0.58 kg (2.1 mol). Also, gas containing ammonia was discharged from the gas-liquid separator 608 through a line 67. The gas was collected in a Tedlar bag, and the gas was injected for gas chromatography using a gas-tight syringe for analysis of the gas component. As a result, the ammonia recovery per 100 minutes was 4.56 g (0.268 mol). Also, when the gas was analyzed by GC-MS, the carbonyl group content in the compound with a carbonyl group in the ammonia was found to be 0.053 mmol.

When step (71-1) to step (71-2) were continued, no blockage of the ammonia discharge line was observed even with an operation time exceeding 380 days.

Comparative Example 6

Step (F-1): Production of N-Substituted Thiocarbamic Acid Ester

In step (F-1), a reactor such as shown in FIG. 2 was used.

A starting solution was prepared by mixing 1.21 kg of hexamethylenediamine, 42.9 kg of 4-(1,1,3,3-tetramethylbutyl)phenol and 2.94 kg of thiourea. The packed tower 202 was heated to 240° C., and the interior pressure was adjusted to 40 kPa. The reboiler temperature was 260° C. A liquid mixture having the same composition as the starting solution was introduced through a line 1 provided at the top end of the packed tower 202, and after stabilization of the operating conditions, the starting solution was introduced at approximately 1.6 g/min, and the reaction mixture was recovered in a storage tank 205 through a line 4 provided at the lowermost section of the packed tower 202. The gas phase component was collected from a line 2 provided at the uppermost section of the packed tower 202, and the component obtained by condensation at the condenser 203 that had been kept at approximately 190° C. was collected in the storage tank 204. When the component collected in the storage tank 204 more than 10 hours after the stabilization of the operating conditions was sampled and analyzed by $^1$H-NMR and $^{13}$C-NMR, it was found to be a mixture of 4-(1,1,3,3-tetramethylbutyl)phenol and thiourea, with a thiourea content of about 25.5 g (0.42 mol) and a 4-(1,1,3,3-tetramethylbutyl)phenol content of 83.1 g (0.40 mol). Ammonia-containing gas was discharged from a line 5 provided at the top of the storage tank 204. The gas was collected in a Tedlar bag, and the gas was injected for gas chromatography using a gas-tight syringe for analysis of the gas component. As a result, the ammonia recovery per 10 minutes was 0.24 g (14.4 mmol). Also, when the gas was analyzed by GC-MS, the amount of thiocarbonyl groups in the compound with a thiocarbonyl group, contained in the ammonia, was found to be 16.2 mmol. The reaction mixture obtained in the storage tank 205 contained N,N'-hexanediyl-di(thiocarbamic acid (4-(1,1,3,3-tetramethylbutyl)phenyl) ester), and the yield of N,N'-hexanediyl-di(thiocarbamic acid (4-(1,1,3,3-tetramethylbutyl)phenyl) ester) was found to be about 78% with respect to hexamethylenediamine. Upon continuing the reaction, and after more than 34 days following stabilization of the operating conditions, the line 5 was found to be blocked and N-substituted thiocarbamic acid ester production was no longer possible.

Comparative Example 7

Step (G-1): Production of N-Substituted Thiocarbamic Acid Ester

The same method was carried out as in step (F-1) of Comparative Example 6, except that the reboiler temperature was 255° C. When the component collected in the storage tank 204 more than 10 hours following stabilization of the operating conditions was sampled and analyzed by $^1$H-NMR and $^{13}$C-NMR, it was found to be a mixture of 4-(1,1,3,3-tetramethylbutyl)phenol and thiourea, with a thiourea content of about 25.5 g (0.42 mol) and a 4-(1,1,3,3-tetramethylbutyl)phenol content of 72.1 g (0.35 mol). Ammonia-containing gas was discharged from a line 5 provided at the top of the storage tank 104. The gas was collected in a Tedlar bag, and the gas was injected for gas chromatography using a gas-tight syringe for analysis of the gas component. As a result, the ammonia recovery per 10 minutes was 0.24 g (14.4 mmol). Also, when the gas was analyzed by GC-MS, the amount of thiocarbonyl groups in the compound with a thiocarbonyl group, contained in the ammonia, was found to be 12.1 mmol. The reaction mixture obtained in the storage tank 205 contained N,N'-hexanediyl-di(thiocarbamic acid (4-(1,1,3,3-tetramethylbutyl)phenyl) ester), and the yield of N,N'-hexanediyl-di(thiocarbamic acid (4-(1,1,3,3-tetramethylbutyl)phenyl) ester) was found to be about 78% with respect to hexamethylenediamine. Upon continuing the reaction, and after more than 70 days following stabilization of the operating conditions, the condenser 203 was found to be blocked and N-substituted thiocarbamic acid ester production was no longer possible.

Example 71 2-Isothiocyanatoethyl Methacrylate

Step (71-1)

After charging 1.8 g of 2-aminoethyl alcohol, 4.6 g of thiourea and 120 g of 2-ethylhexyl alcohol into a 500 mL internal volume flask, the interior was exchanged with a nitrogen atmosphere. A Dimroth condenser was mounted onto the flask and cooling water at approximately 5° C. was circulated through the cooler. Upon immersing the flask in an oil bath that had been preheated to 200° C. while stirring the contents of the flask, reflux was initiated. Heating was performed for 5 hours in this state.

Step (71-2): Production of Isothiocyanate

The reaction mixture of step (71-1) was subjected to vacuum distillation with a rotary evaporator to distill off the 2-ethylhexyl alcohol. The residual solution was placed in a glass tube equipped with a trap bulb, the interior was reduced in pressure to 10 kPa, and heating was performed with a glass tube oven that had been heated to 250° C. When the liquid collected at the trap bulb was analyzed by high-performance liquid chromatography, 2-hydroxyethyl isothiocyanate was found to be obtained at a yield of 40% with respect to 2-aminoethyl alcohol.

Example 72

Step (72-1) 2-Isothiocyanatoethyl Methacrylate Production Method

After charging 1.0 g of 2-hydroxyethanolethyl methacrylate and 100 g of tetrahydrofuran in a flask with an internal volume of 200 ml, the interior was exchanged with a nitrogen atmosphere. The flask was immersed in an ice bath and cooled while stirring, and then 1.3 g of methacrylic acid chloride and 1.2 g of triethylamine were added. Next, after stirring for 2 hours at room temperature, the contents of the flask were transferred to a separatory funnel and rinsed with aqueous sodium hydrogencarbonate, 1N hydrochloric acid and water, and after drying the organic layer over sodium sulfate, it was subjected to vacuum distillation with a rotary evaporator. When the concentrate was analyzed by high-performance liquid chromatography, 2-isothiocyanatoethyl methacrylate was found to be obtained at a yield of 97% with respect to 2-hydroxyethyl isothiocyanate.

Example 73

Step (73-1): Production of N-Substituted O-Substituted Thiocarbamate

After charging 2.2 g of tris(2-aminoethyl)amine, 6.9 g of thiourea and 160 g of 2-butoxyethanol in a 500 mL internal volume flask, the interior was exchanged with a nitrogen atmosphere. A Dimroth condenser was mounted onto the flask and cooling water at approximately 5° C. was circulated through the cooler. Upon immersing the flask in an oil bath that had been preheated to 200° C. while stirring the contents of the flask, reflux was initiated. Heating was performed for 8 hours in this state. When the reaction mixture was analyzed by high-performance liquid chromatography, tris[O-(2-butoxyethyl)-N-ethylthiocarbamic acid] amine was found to be obtained at a yield of 70% with respect to tris(2-aminoethyl)amine.

Step (73-2): Production of Tris(2-Isothiocyanatoethyl) Amine

The reaction mixture of step (73-1) was subjected to vacuum distillation with a rotary evaporator to distill off the 2-ethyl alcohol. The residual solution was placed in a glass tube equipped with a trap bulb, the interior was reduced in pressure to 10 kPa, and heating was performed with a glass tube oven that had been heated to 250° C. When the solution collected in the trap bulb was analyzed by high-performance liquid chromatography, tris(2-isothiocyanatoethyl)amine was found to be obtained at a yield of 40% with respect to tris(2-aminoethyl)amine.

INDUSTRIAL APPLICABILITY

According to the invention it is possible to provide an isothiocyanate production method that utilizes easily handleable compounds and can be easily accomplished without by-production of poisonous compounds.

EXPLANATION OF SYMBOLS

101: Stirring tank, 102, 108: distillation columns, 103, 109: condensers, 104, 106, 110, 112: storage tanks, 105, 111: reboilers, 107: thin-film evaporator, 10, 11, 12, 13, 14, 15, 16, 17, 18, 19, 20, 21, 22, 23: lines, 201, 204, 205: storage tanks, 202: packed tower, 203: condenser, 206: reboiler, 1, 2, 3, 4, 5: lines, 301, 303, 307, 309: storage tanks, 302: thin-film distillation apparatus, 304: distillation column, 306: gas-liquid separator, 305: condenser, 308: reboiler, 30, 31, 32, 34, 35, 36: lines, 401, 406, 407, 408, 410, 414, 416: storage tanks, 402, 411: packed towers, 403, 412: condensers, 404, 413: gas-liquid separators, 405, 415: reboilers, 409: mixing vessel, 40, 41, 42, 43, 44, 45, 46, 47, 48, 49, 50, 51: lines, 600, 601, 602, 604, 609, 610, 613: storage tanks, 603: mixing vessel, 605: distillation column, 606, 611: condensers, 607: reboiler, 608, 612: gas-liquid separators, 60, 61, 62, 63, 64, 65, 66, 67, 68, 69: lines.

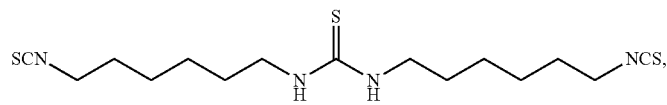

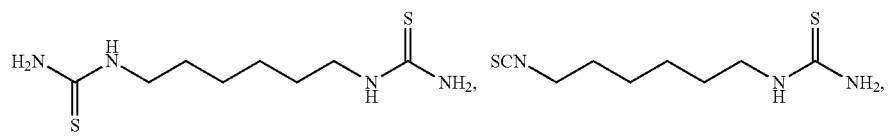

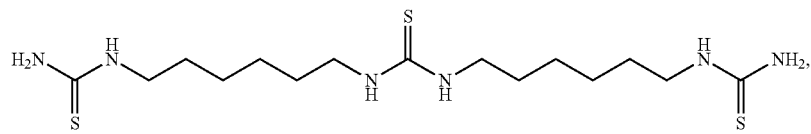

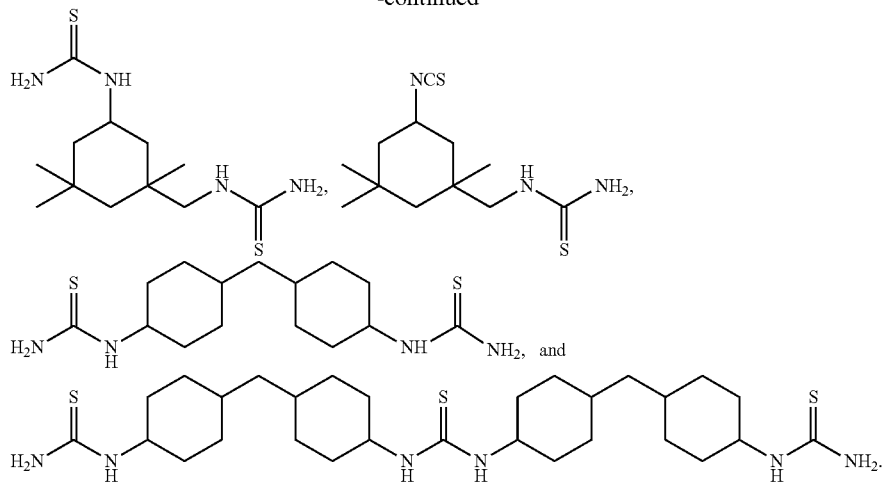

The invention claimed is:

1. An isothiocyanate composition containing an isothiocyanate at 97 wt % or more based on a total mass of the isothiocyanate composition and a compound having at least one type of functional group selected from the group consisting of groups represented by the following formula (1) and formula (2)

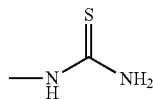

(1)

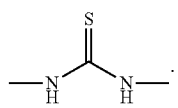

(2)

2. The isothiocyanate composition according to claim 1, wherein a total amount of the group represented by formula (1) and formula (2) is at least 0.1 mol ppm and no greater than $1.0 \times 10^4$ mol ppm.

3. The isothiocyanate composition according to claim 1, wherein a total amount of the group represented by formula (1) and formula (2) is at least 0.3 mol ppm and no greater than $5.0 \times 10^3$ mol ppm.

4. The isothiocyanate composition according to claim 1, wherein a total amount of the group represented by formula (1) and formula (2) is at least 0.5 mol ppm and no greater than $3.0 \times 10^3$ mol ppm.

5. The isothiocyanate composition according to claim 1, wherein, when a compound with a thiocarbamate group is present in the isothiocyanate composition, an amount of thiocarbamate group is at least 0.1 mol ppm and no greater than $1.0 \times 10^4$ mol ppm with respect to the total amount of isothiocyanate groups in the composition.

6. The isothiocyanate composition according to claim 1, wherein the isothiocyanate is a compound having none of the groups represented by formulae (1) and (2).

7. The isothiocyanate composition according to claim 1, wherein the isothiocyanate is a compound represented by the following formula (9):

(9)

wherein R¹ is selected from the group consisting of straight-chain hydrocarbon groups, unsubstituted alicyclic hydrocarbon-derived groups, alkyl-substituted cyclohexane-derived groups, dialkyl-substituted cyclohexane-derived, trialkyl-substituted cyclohexane-derived groups, monoalkyl-substituted benzenes, dialkyl-substituted benzenes, and aromatic hydrocarbon-derived groups, and n is an integer of 1 to 10.

8. The isothiocyanate composition according to claim 7, wherein in formula (9), the straight-chain hydrocarbon group is selected from the group consisting of methylene, dimethylene, trimethylene, tetramethylene, pentamethylene, hexamethylene and octamethylene.

9. The isothiocyanate composition according to claim 7, wherein in formula (9), the unsubstituted alicyclic hydrocarbon-derived group is selected from the group consisting of cyclopentane, cyclohexane, cycloheptane, cyclooctane and bis(cyclohexyl)alkanes.

10. The isothiocyanate composition according to claim 7, wherein the alkyl-substituted cyclohexane-derived group is selected from the group consisting of methylcyclopentane, ethylcyclopentane, methylcyclohexane and its isomers, ethylcyclohexane and its isomers, propylcyclohexane and its isomers, butylcyclohexane and its isomers, pentylcyclohexane and its isomers and hexylcyclohexane and its isomers.

11. The isothiocyanate composition according to claim 7, wherein the dialkyl-substituted cyclohexane-derived group is selected from the group consisting of dimethylcyclohexane and its isomers, diethylcyclohexane and its isomers, and dibutylcyclohexane and its isomers.

12. The isothiocyanate composition according to claim 7, wherein the trialkyl-substituted cyclohexane-derived group is selected from the group consisting of 1,5,5-trimethylcyclohexane, 1,5,5-triethylcyclohexane, 1,5,5-tripropylcyclohexane and its isomers, and 1,5,5-tributylcyclohexane and its isomers.

13. The isothiocyanate composition according to claim 7, wherein the monoalkyl-substituted benzene is selected from the group consisting of toluene, ethylbenzene and propylbenzene.

14. The isothiocyanate composition according to claim 7, wherein the dialkyl-substituted benzene is selected from the group consisting of xylene, diethylbenzene and dipropylbenzene.

15. The isothiocyanate composition according to claim 7, wherein the aromatic hydrocarbon-derived group is selected from the group consisting of diphenylalkanes and benzene.

16. The isothiocyanate composition according to claim 1, wherein the compound is a compound represented by following formula (18):

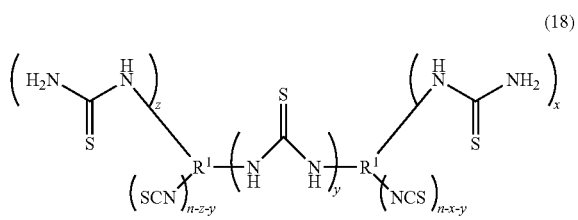

wherein R¹ is selected from the group consisting of straight-chain hydrocarbon groups, unsubstituted alicyclic hydrocarbon-derived groups, alkyl-substituted cyclohexane-derived groups, dialkyl-substituted cyclohexane-derived, trialkyl-substituted cyclohexane-derived groups, monoalkyl-substituted benzenes, dialkyl-substituted benzenes, and aromatic hydrocarbon-derived groups, n is an integer of 1 to 10, x, y, and z each independently represent an integer of 0 to n, and n-z-y and n-x-y are both an integer of 0 or greater.

17. The isothiocyanate composition according to claim 16, wherein the compound represented by formula (18) is a compound represented by the following formula (19):

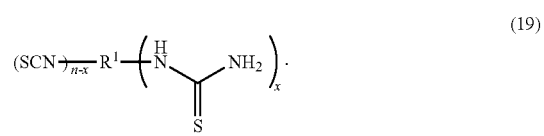

18. The isothiocyanate composition according to claim 1, wherein the compound is selected from the group consisting of: